United States Patent
Hays et al.

(10) Patent No.: US 7,518,736 B2
(45) Date of Patent: *Apr. 14, 2009

(54) OPTICAL AIR DATA SYSTEM

(75) Inventors: Paul Byron Hays, Ann Arbor, MI (US);
Jane Camile Pavlich, Ann Arbor, MI (US); Greg Alan Ritter, Hamburg, MI (US)

(73) Assignee: Michigan Aerospace Corporation, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/927,196

(22) Filed: Oct. 29, 2007

(65) Prior Publication Data

US 2008/0180690 A1    Jul. 31, 2008

Related U.S. Application Data

(63) Continuation of application No. 11/460,603, filed on Jul. 27, 2006, now Pat. No. 7,495,774, which is a continuation-in-part of application No. 10/366,910, filed on Feb. 14, 2003, now Pat. No. 7,106,447.

(60) Provisional application No. 60/360,818, filed on Mar. 1, 2002, provisional application No. 60/596,531, filed on Oct. 3, 2005.

(51) Int. Cl.
G01B 9/02 (2006.01)
G01P 3/36 (2006.01)

(52) U.S. Cl. .................... 356/519; 356/28.5

(58) Field of Classification Search ........... 356/28.5, 356/450, 484, 480, 519
See application file for complete search history.

(56) References Cited

U.S. PATENT DOCUMENTS

| 3,389,256 A | 6/1968 | Astheimer |
| 3,984,685 A | 10/1976 | Fletcher et al. |
| 4,167,329 A | 9/1979 | Jelalian et al. |
| 4,195,931 A | 4/1980 | Hara |
| 4,270,864 A | 6/1981 | Barrett et al. |
| 4,483,614 A | 11/1984 | Rogers |
| 4,558,950 A | 12/1985 | Ulrich et al. |
| 4,585,341 A | 4/1986 | Woodfield |

(Continued)

OTHER PUBLICATIONS

O'Brien et al., U.S. Appl. No. 60/400,462, filed on Aug. 2, 2002.

(Continued)

*Primary Examiner*—Patrick J Connolly
(74) *Attorney, Agent, or Firm*—Raggio & Dinnin, P.C.

(57) ABSTRACT

At least one second beam of light from a first beam of light generated by a laser is directed into an atmosphere. Light therefrom scattered by molecules or aerosols in the atmosphere is collected by at least one telescope as at least one light signal, which together with a reference beam from the first beam of light are simultaneously processed by an interferometer, and resulting fringe patterns are imaged onto a detector adapted to output a resulting at least one signal responsive thereto. In various aspects: a data processor gates the signal to provide a range-responsive measurement; the light signal is multiplexed; a circle-to-line interferometer optic transforms an at least partially circular fringe pattern to a substantially linear fringe pattern; or a CCD detector provides for recording a range-resolved image by successively transferring charges from one adjacent row of photosites to another.

24 Claims, 36 Drawing Sheets

U.S. PATENT DOCUMENTS

| | | | |
|---|---|---|---|
| 4,676,586 A | | 6/1987 | Jones et al. |
| 4,724,326 A | * | 2/1988 | Poultney et al. .......... 250/458.1 |
| 4,818,101 A | | 4/1989 | Soreide et al. |
| 4,850,709 A | | 7/1989 | Ban et al. |
| 4,893,003 A | | 1/1990 | Hays |
| 4,937,447 A | | 6/1990 | Barrett et al. |
| 4,983,033 A | | 1/1991 | Suzuki |
| 4,988,190 A | * | 1/1991 | Miles ......................... 356/28 |
| 5,000,566 A | | 3/1991 | Kuppenheimer, Jr. et al. |
| 5,029,999 A | | 7/1991 | Kremer et al. |
| 5,047,653 A | | 9/1991 | Garcia et al. |
| 5,055,692 A | | 10/1991 | Abbiss et al. |
| 5,088,815 A | * | 2/1992 | Garnier et al. ............ 356/28.5 |
| 5,111,055 A | * | 5/1992 | Fima ....................... 250/461.1 |
| 5,116,133 A | | 5/1992 | Sweeney |
| 5,161,890 A | * | 11/1992 | Fima .......................... 374/123 |
| 5,214,484 A | | 5/1993 | de Mollerat du Jeu et al. |
| 5,216,477 A | | 6/1993 | Korb |
| 5,257,274 A | | 10/1993 | Barrett et al. |
| 5,267,010 A | | 11/1993 | Kremer et al. |
| 5,272,513 A | | 12/1993 | Vahala et al. |
| 5,285,070 A | | 2/1994 | Barrett et al. |
| 5,285,256 A | | 2/1994 | Nelson et al. |
| 5,325,175 A | | 6/1994 | Mocker et al. |
| 5,394,238 A | * | 2/1995 | Mocker et al. .............. 356/342 |
| 5,504,620 A | | 4/1996 | Maul |
| 5,584,117 A | | 12/1996 | Lee et al. |
| 5,610,705 A | | 3/1997 | Brosnan et al. |
| 5,621,523 A | | 4/1997 | Oobayashi et al. |
| 5,629,521 A | | 5/1997 | Lee et al. |
| 5,666,195 A | | 9/1997 | Shultz et al. |
| 5,667,304 A | * | 9/1997 | Gelbwachs ................. 374/137 |
| 5,708,495 A | | 1/1998 | Pitz et al. |
| 5,982,478 A | | 11/1999 | Ainsworth et al. |
| 6,034,760 A | | 3/2000 | Rees |
| 6,141,086 A | | 10/2000 | Vahala et al. |
| 6,163,380 A | | 12/2000 | Hays |
| 6,215,802 B1 | | 4/2001 | Lunt |
| 6,297,878 B1 | | 10/2001 | Miller |
| 6,313,908 B1 | | 11/2001 | McGill et al. |
| 6,320,651 B1 | | 11/2001 | Manhart et al. |
| 6,424,408 B1 | | 7/2002 | Ooga |
| 6,437,855 B1 | | 8/2002 | Wilson et al. |
| 6,522,397 B2 | | 2/2003 | Barricau et al. |
| 6,608,669 B2 | | 8/2003 | Holton |
| 6,634,600 B2 | | 10/2003 | Krawczyk et al. |
| 6,735,395 B1 | | 5/2004 | Bai |
| 6,894,768 B2 | | 5/2005 | Caldwell et al. |
| 7,106,447 B2 | * | 9/2006 | Hays .......................... 356/450 |
| 2003/0076568 A1 | | 4/2003 | Wu et al. |
| 2003/0151732 A1 | | 8/2003 | Rogers et al. |
| 2003/0219252 A1 | * | 11/2003 | Hays .......................... 398/118 |
| 2004/0239913 A1 | | 12/2004 | Kobayashi et al. |
| 2005/0109940 A1 | | 5/2005 | Carr |
| 2006/0262324 A1 | * | 11/2006 | Hays et al. ................. 356/519 |
| 2007/0171397 A1 | | 7/2007 | Halldorsson et al. |
| 2008/0117419 A1 | * | 5/2008 | Hays et al. ................. 356/342 |
| 2008/0117433 A1 | * | 5/2008 | Hays et al. ................. 356/519 |
| 2008/0180690 A1 | * | 7/2008 | Hays et al. ................. 356/519 |
| 2008/0180691 A1 | * | 7/2008 | Hays et al. ................. 356/519 |

OTHER PUBLICATIONS

Abreu, Vincent J., "Wind measurements from an oribital platform using a lidar system with incoherent detection: an analysis," Applied Optics, vol. 18, No. 17, Sep. 1, 1979, pp. 2992-2997.

Abreu, V. J., "Lidar from orbit," Optical Engineering, vol. 19, No. 4, Jul./Aug. 1980, pp. 489-493.

Hays, P. B., Killeen, T. L., Kennedy, B. C., "The Fabry-Pérot interferometer on Dynamics Explorer," Space Sci. Instrum. 5, 395-416, 1981.

Rees, D., T.J. Fuller-Rowell, A. Lyons, T.L. Killeen and P.B. Hays, "Stable and rugged etalon for the Dynamics Explorer Fabry-Perot interferometer 1: Design and construction," Appl. Opt., 21, 3896-3902, 1982.

Kileen, Timothy L., and P.B. Hays, "Doppler line profile analysis for a multichannel Fabry-Perot interferometer," Applied Optics, vol. 23, No. 4, Fegruary 15, 1984, pp. 612-620.

Abreu, V.J., J.E. Barnes, and P.B. Hays, Observations of winds with an incoherent lidar detector, Appl. Opt., 31, 4509-4514, 1992.

Hays, P.B., and HRDI Science Team: V.J. Abreu, M.D. Burrage, D.A. Gell, H.J. Grassl, A.R. Marshall, Y.T. Morton, D.A. Ortland, W.R. Skinner, D.L. Wu, and J.-H. Yee, "Remote sensing of mesospheric winds with the High Resolution Doppler Imager," Planet. Space Sci., 40, #12, 1599-1606, 1992.

Rye, Barry J., and R. Michael Hardesty, "Discrete Spectral Peak Estimation in Incoherent Backscatter Heterodyne Lidar. I: Spectral Accumulation and the Cramer-Rao Lower Bound," IEEE Transaction on Geoscience and Remote Sensing, vol. 31, No. 1, Jan. 1993, pp. 16-27.

Burrage, M.D., W.R. Skinner, A.R. Marshall, P.B. Hays, R.S. Lieberman, S.J. Franke, D.A. Gell, D.A. Ortland, F.J. Schmidlin, R.A. Vincent, and D.L. Wu, "Validation of winds from the High Resolution Doppler Imager on UARS," Optical Spectroscopic Techniques and Instrumentation for Atmospheric and Space Research, Jinxue Wang, Paul Hays, Editors, Proc. SPIE 2266, pp. 294-306, 1994.

Skinner, W.R., and P.B. Hays, "Incoherent Doppler lidar for measurement of atmospheric winds," Optical Spectroscopic Techniques and Instrumentation for Atmospheric and Space Research, Jinxue Wang, Paul Hays, Editors, Proc. SPIE 2266, pp. 383-394, 1994.

Wang, J., J.Wu, and P.B. Hays, "University of Michigan ground-based circle-to-line Fabry-Perot interferometer and its applications in mesosphere and lower thermosphere dynamics studies," in Optical Spectroscopic Techniques and Instrumentation for Atmospheric and Space Research, Jinxue Wang, Paul Hays, Editors, Proc. SPIE 2266, pp. 133-142, 1994.

Wu, J., J. Wang, and P.B. Hays, "Performance of a Circle-to-Line Optical System for a Fabry-Perot Interferometer: A Laboratory Study", Appl. Opt. 33, No. 34, 7823-7828, Dec. 1994.

Grassl, H.J., W. R. Skinner, P. B. Hays, M. D. Burrage, D. A. Gell, A. R. Marshall, D. A. Ortland, and V. J. Abreu, "Atmospheric wind measurements with the High Resolution Doppler Imager (HRDI)," J. Spacecraft & Rockets 32, No. 1, 169-176, Jan.-Feb. 1995.

Skinner, W.R., P.B. Hays, H. J. Grassl, D.A. Gell, M.D. Burrage, A.R. Marshall, and J. Kafkalidis, "The High Resolution Doppler Imager: Instrument performance in orbit since late 1991," Optical Spectroscopic Techniques and Instrumentation for Atmospheric and Space Research II, Paul B. Hays, Jinxue Wang, Editors, Proc. SPIE 2830, 202-214, 1996.

Barnes, John E. and David J. Hofman, "Lidar measurements of stratospheric aerosol over Mauna Loa Observatory," Geophysical Research Letters, vol. 24, No. 15, Aug. 1, 1997.

McGill, Matthew J., Wilbert R. Skinner, and Todd D. Irgang, "Analysis techniques for the recovery of winds and backscatter coefficients from a multiple-channel incoherent Doppler lidar," Applied Optics, vol. 36, No. 6, Feb. 20, 1997, pp. 1253-1268.

McGill, Matthew J., Wilbert R. Skinner, and Todd D. Irgang, "Validation of wind profiles measured with incoherent Doppler lidar," Applied Optics, vol. 36, No. 9, Mar. 20, 1997, pp. 1928-1939.

Souprayen, Claude, Anne Tgarnier, Algert Hertzong, Alain Hauchecorne,a nd Jacques Porteneuve, "Rayleigh-Mie Doppler wind lidar for atmospheric measurements. I. Instrument setup, validation, and first climatological results," Applied Optics, vol. 38, No. 12, Apr. 20, 1999, pp. 2410-2421.

McGill, Matthew J., William D. Hart, Jack A. McKay, and James D. Spinhirne, "Modeling the performand of direct-detection Doppler lidar system including cloud and solar background variability," Applied Optics, Vo. 38, No. 30, Oct. 20, 1999, pp. 6388-6397.

Miles, R.B., Lempert, W.R., Forkey, J.N., "Laser Rayleigh scattering," Meas. Sci. Technol. 12, R33-R51, 2001.

Dehring, D. T., C. A. Nardell, J. C. Pavlich, P. B. Hays, and I. G. Dors, "Performance and comparison of 532nm and 355nm GroundWinds lidars," Lidar Remote Sensing for Industry and Environment Monitoring III, Hangzhou, China, SPIE Proceedings, 4893: 337-47, Oct. 2002.

Nardell, Carl A., Hays, Paul B., Jane C. Pavlich, Michael Dehring, and Greg Sypitkowski, "GroundWinds New Hampshire and the LIDARFest 2000 Campaign," Invited Paper, Lidar Remote Sensing for Industry and Environment Monitoring II, San Diego, SPIE Proceedings, 4484: 36-50, 2002.

Irgang, T.D., P.B. Hays, and W.R. Skinner, "Two-channel direct-detection Doppler lidar employing a charged-coupled device as a detector," Appl. Opt., 41, 1145-1155, 2002.

Liu, Zhi-Shen, Dong Wu, Jin-Tao Liu, Kai-Lin Zhang, Wei-Biao Chen, Xiao-Quan Song, Johnathan W. Hair, and Chiao-Yao She, "Low-altitude atmospheric wind measurement from the combined Mie and Rayleight backscattering by Doppler lidar with an iodine filter," Applied Optics, Vo. 42, No. 33, Nov. 20, 2002, pp. 7079-7086.

Abreu, V.J., P.B. Hays, and W.R. Skinner, "The High Resolution Doppler Imager," Optics & Photonics News, 2, #10, 28-30, 1991.

Skinner, W.R., P.B. Hays, H.J. Grassl, D.A. Gell, M.D. Burrage, A.R. Marshall, and D.A. Ortland, "The High Resolution Doppler Imager on the Upper Atmosphere Research Satellite," Optical Spectroscopic Techniques and Instrumentation for Atmospheric and Space Research, Jinxue Wang, Paul Hays, Editors, Proc. SPIE 2266, pp. 281-293, 1994.

Marshall, A.R., D.A. Gell, J.-H. Yee, D.A. Ortland, M.D. Burrage, W.R. Skinner, and P.B. Hays, "Stellar alignment of the High Resolution Doppler Imager," J. Spacecraft & Rockets 32, #6, 1039-1043. 1995.

Skinner, W.R., P.B. Hays, M.D. Burrage, D.A. Gell, A.R. Marshall, and H.J. Grassl, "The High Resolution Doppler Imager: Instrument performance in orbit since late 1991," SPIE: Optical Science, Engineering, and Instrumentation, Denver '96 Symposium, Denver, CO, Aug. 1996.

Yoe, J.G., Rama Varma Raja, M.K., Hardesty, R.M., Brewer, W.A., Moore, B., Ryan, J., Hays, P.B., Nardell, C.A., Gentry, B., Day, M., and Rancourt, K., "GroundWinds 2000 field campaign: Demonstration of new Doppler lidar technology and wind lidar data intercomparison," Lidar Remote Sensing for Industry and Environment Monitoring III, Hangzhou, China, SPIE Proceedings, 4893:327-336, 2003.

Tchoryk, P., C. Watkins, S. Lindemann, P. Hays, and Nardell, C.A., "Molecular Optical Air Data System (MOADS)," Laser Radar Technology and Applications VI, SPIE Aerosense Conference, Orlando, FL, SPIE 4377-28, Apr. 16-20, 2001.

Imaki, Maqsaharu, Dongsong Sun, and Takao Kobayashi, "Direct-detection Doppler lidar for two-dimensional wind field measurements of the troposphere," in Lidar Remotes Sensing for Industry and Environment Monitoring III, Upendra N. Singh, Toshikasu Itabe, Zhishen Liu, Editors, Proceedings of SPIE, vol. 4893, 2003, pp. 303-310.

Shibata, Yasukuni, Chikao Nagasawa, Makoto Abo, and Tomohiro Nagai, "Wind measurement accuracy with incoherent Doppler lidar using an iodine vapor filter," in Lidar Remotes Sensing for Industry and Environment Monitoring III, Upendra N. Singh, Toshikasu Itabe, Zhishen Liu, Editors, Proceedings of SPIE, vol. 4893, 2003, pp. 529-536.

Office Action in U.S. Appl. No. 11/460,603, mailed on Aug. 27, 2008, including list of references cited by Examiner, search information and Examiner's search strategy & list of references cited by applicant and considered by examiner, 19 pp.

Office Action in U.S. Appl. No. 11/460,603, mailed on Aug. 26, 2008, including list of references cited by Examiner, search information and Examiner's search strategy, 10 pp.

Press, W.H., Teukolsky, S.A., Vetterling, W.T. and Flannery, B.P., Numerical Recipes in C, The Art of Scientific Computing, Second Edition, Cambridge University Press, 1992, pp. 681-685.

Dehring, Michael T., Ivan G. Dors, Carl A. Nardell, Jane C. Pavlich, and Paul B. Hays, "Recent Measurement Achievements of the GroundWinds Direct Detection Doppler Wind Lidars," Presented at the CLRC in Bar Harbor Jun. 2003.

Dehring, Michael T., Carl A. Nardell, and Paul B. Hays, "Space LIDAR Simulations Derived from the GroundWinds New Hampshire and Hawaii Instruments," Lidar Remote Sensing for Environmental Monitoring IV, SPIE Proceedings, 5154:84-92, San Diego, CA, Aug. 2003.

Dehring, M. T., Carl A. Nardell, Paul B. Hays, Jane C. Pavlich, Berrien Moore III, and Jinxue Wang, "Instrument specifications and performance prediction for 2005 High Altitude (30km) Balloon Demonstration of GroundWinds Fringe Imaging Doppler LIDAR," Laser Radar Technology for Remote Sensing, SPIE Proceedings 5240:165-173, Barcelona, Spain, Sep. 2003.

Wand, J., M. Dehring, C. Nardell, P. Hays, D. Dykeman, and B. Moore III , "Direct Detection Doppler Winds Lidar: Ground-based Operation to Space," Lidar Remote Sensing for Environmental Monitoring IV, SPIE Proceedings. 5151:93-104, San Diego, CA, Aug. 2003.

Watkins, C.B., Richey, C.J., Tchoryk, P., Ritter, G., Hays, P.B., Nardell, C.A., Willis, T., and Urzi, B., "Molecular Optical Air Data System (MOADS) Flight Experiment," Laser Radar Technology and Applications VIII, SPIE Aerosense Conference, Orlando, Florida, SPIE Proceedings, 5086: 236-245, Apr. 2003.

Barnes, John E., Sebastian Bronner, Robert Beck, and N.C. Parikh, "Boundary layer scattering measurements with a charge-coupled device camera lidar," Applied Optics, Vo. 42, No. 15, May 20, 2003, pp. 2647-2652.

Nardell, C., J. Wertz, M. Dehring, and P. Tchoryk, "Low-Cost Mission Architecture for Global Tropospheric Wind Measurements," Spacecraft Platforms and Infrastructure, SPIE Proceedings, 5419:47-56, Orlando, FL, Apr. 2004.

Watkins, Christopher B., Charles J. Richey, Peter Tchoryk, Jr., Greg A. Ritter, Michael Dehring, Paul B. Hays, Carl A. Nardell, and Russell Urzi, "Molecular Optical Air Data System (MOADS) Prototype II," Laser Radar Technology and Applications IX, Orlando, FL, SPIE Proceedings, 5412:10-20, Apr. 13-15, 2004.

Durand, Y., A. Culoma, R. Maynart, D. Morancais, and F. Fabre, "Pre-Development of a Direct Detection Doppler Wind Lidar for ADM/AEOLUS Mission," in Sensors, Systems, and Next-Generation Satellites VII, edited by Roland Maynart, Steven P. Neeck, Haruhisa Shimoda, Joan B. Little, and Michelle L. Alen, Proceedings of SPIE, vol. 5234, 2004, pp. 354-363.

Dehring, Michael T., James M. Ryan, Paul B. Hays, Berrien Moore III, and Jinxue Wang, "GroundWinds Balloon Fringe Imaging Doppler LIDAR Mission Concept and Instrument Performance," Lidar Remote Sensing for Industry and Environmental Monitoring V, SPIE Proceedings, 5653:210-219, Honolulu, Hawaii, Nov. 2004.

Hays, P. B., Michael, T. Dehring, Lennard A. Fisk, Peter Tchoryk, Jr., Ivan Dors, James Ryan, Jinxue Wang, Michael Hardesty, Bruce Gentry, Floyd Hovis, "Space-based Doppler Winds LIDAR: A Vital National Need," National Research Council (NRC) Decadal Study Request for Information, May 2005.

Office Action in U.S. Appl. No. 11/927,155, mailed on Oct. 2, 2008, including list of references cited by Examiner, search information and Examiner's search strategy, 15 pp.

Office Action in U.S. Appl. No. 11/927,243, mailed on Oct. 2, 2008, including list of references cited by Examiner, search information and Examiner's search strategy, 14 pp.

* cited by examiner

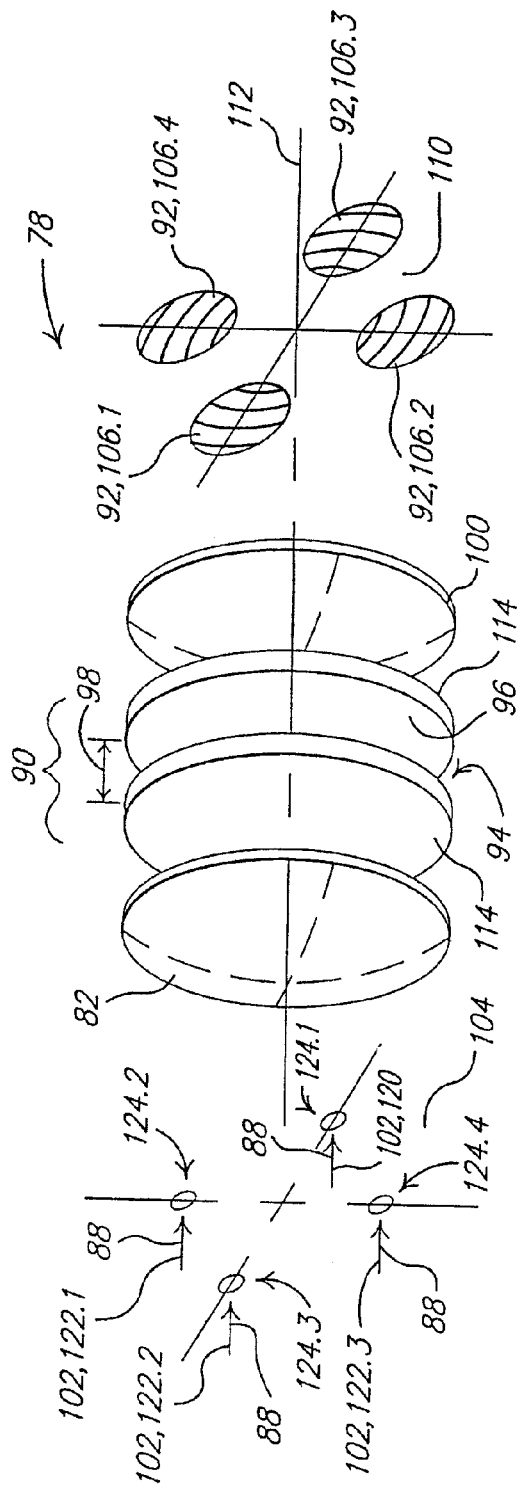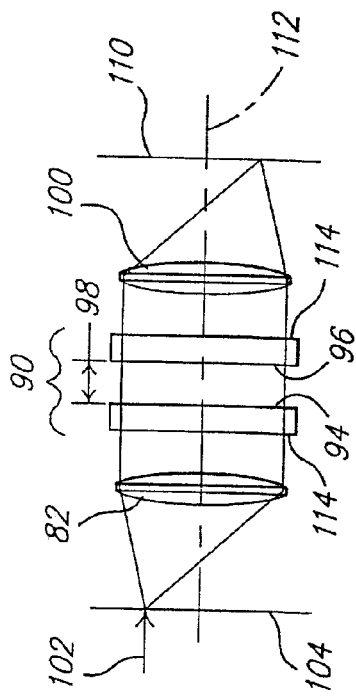

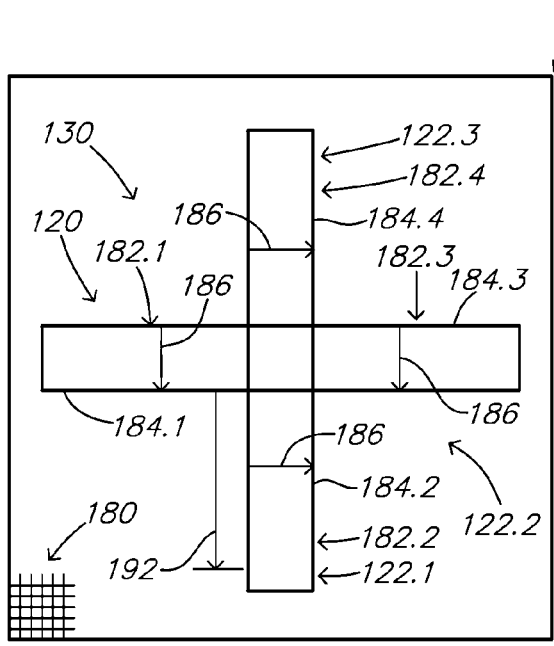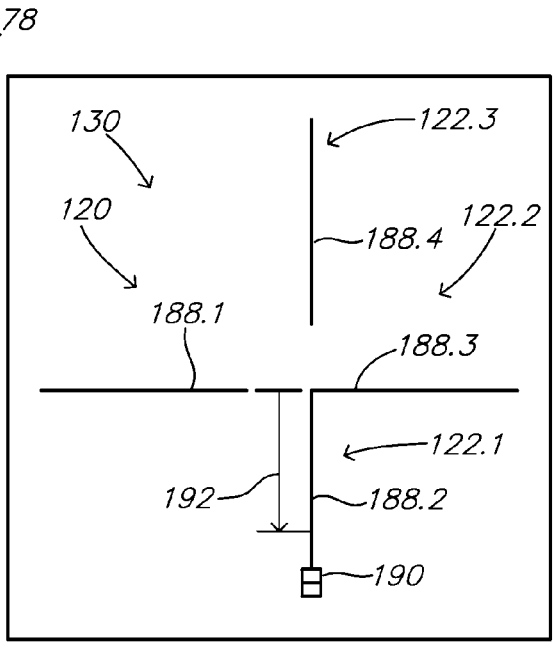
*Fig. 15a*  *Fig. 15b*
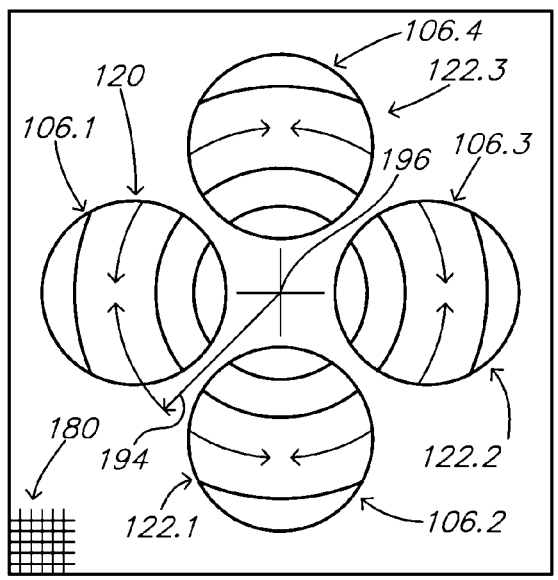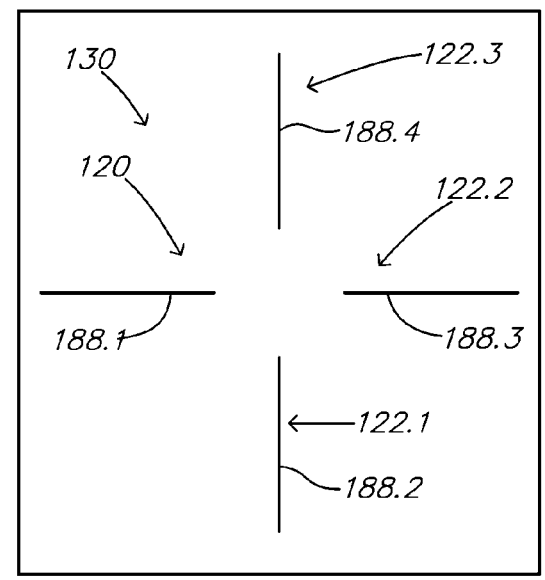
*Fig. 16a*  *Fig. 16b*

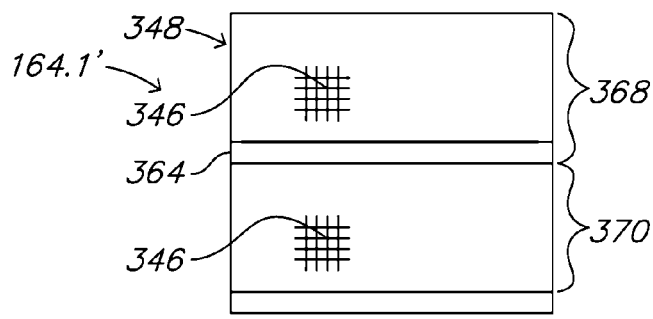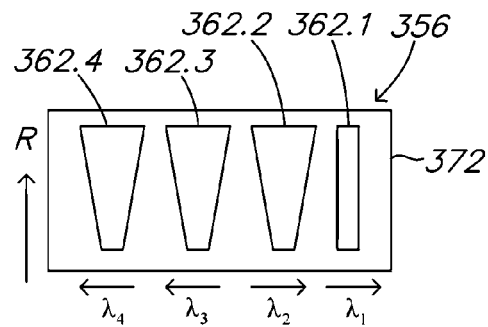
*Fig. 43a*  *Fig. 43e*
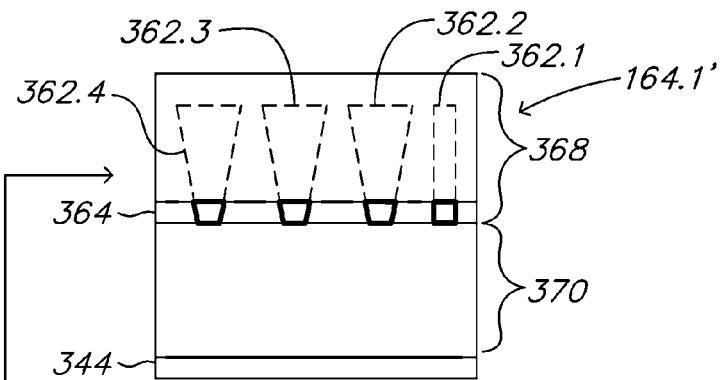
*Fig. 43b*
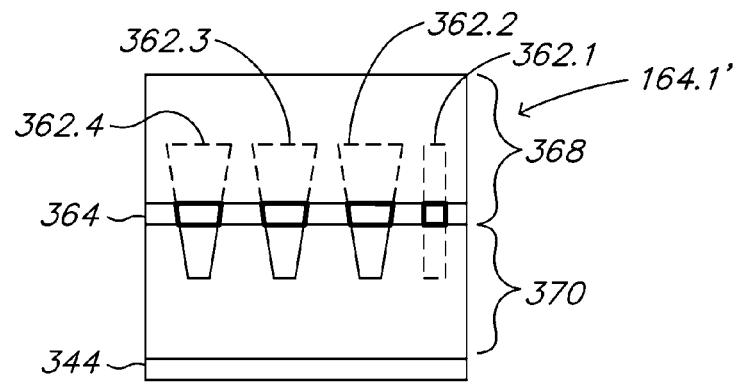
*Fig. 43c*
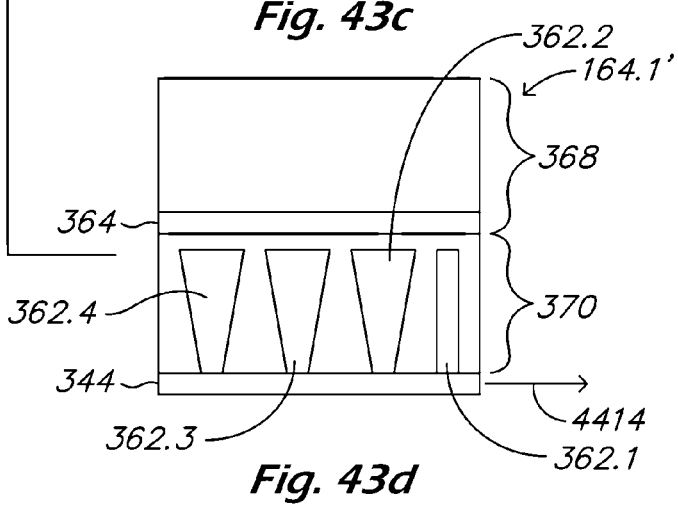
*Fig. 43d*

OPTICAL AIR DATA SYSTEM

CROSS-REFERENCE TO RELATED APPLICATIONS

The instant application is a continuation of U.S. application Ser. No. 11/460,603, filed on Jul. 27, 2006, which is a continuation-in-part of U.S. application Ser. No. 10/366,910, filed on Feb. 14, 2003, now U.S. Pat. No. 7,106,447, which issued on Sep. 12, 2006, and which claims a benefit of priority from U.S. Provisional Application Ser. No. 60/360,818, filed on Mar. 1, 2002. U.S. application Ser. No. 11/460,603 also claims a benefit of priority from U.S. Provisional Application Ser. No. 60/596,531, filed on Oct. 3, 2005. The entire content of each of the above-identified applications is incorporated herein by reference.

STATEMENT REGARDING FEDERALLY SPONSORED RESEARCH OR DEVELOPMENT

This invention was made with Government support under Contract No. F33615-92-D-3602 awarded by the Flight Dynamics Directorate, Wright Laboratory, Air Force Materiel Command (ASC), United States Air Force, Wright-Patterson AFB OHIO 45433-6553. The Government has certain rights in this invention.

BRIEF DESCRIPTION OF THE DRAWINGS

FIG. 5a illustrates an isometric view of a Fabry-Pérot interferometer;

FIG. 5b illustrates a side view of the Fabry-Pérot interferometer illustrated in FIG. 5a for one associated fiber-optic input and a corresponding output.

FIG. 14 illustrates a fragmentary end view of a concave conical reflector on a face of the first pyramidal shaped optic element illustrated in FIGS. 11 and 12, wherein the direction of the end view is substantially parallel to the face of the first pyramidal shaped optic element;

FIGS. 15a and 15b illustrate a cross-binning process operating on a cross-pattern from a quad-CLIO element;

FIGS. 16a and 16b illustrate a circular process operating on a fringe pattern from a Fabry-Pérot interferometer;

FIG. 18b illustrates an alternate decision block of the first embodiment of a circular binning process illustrated in FIG. 18a;

FIG. 43a illustrates a plan view of a CCD detector in an initial state;

FIG. 43b illustrates a plan view of the CCD detector at the beginning stage of an image recording cycle;

FIG. 43c illustrates a plan view of the CCD detector at an intermediate stage of the image recording cycle;

FIG. 43d illustrates a plan view of the CCD detector at a final stage of the image recording cycle;

FIG. 43e illustrates an image transferred from the CCD detector;

DESCRIPTION OF EMBODIMENT(S)

Figure 1:
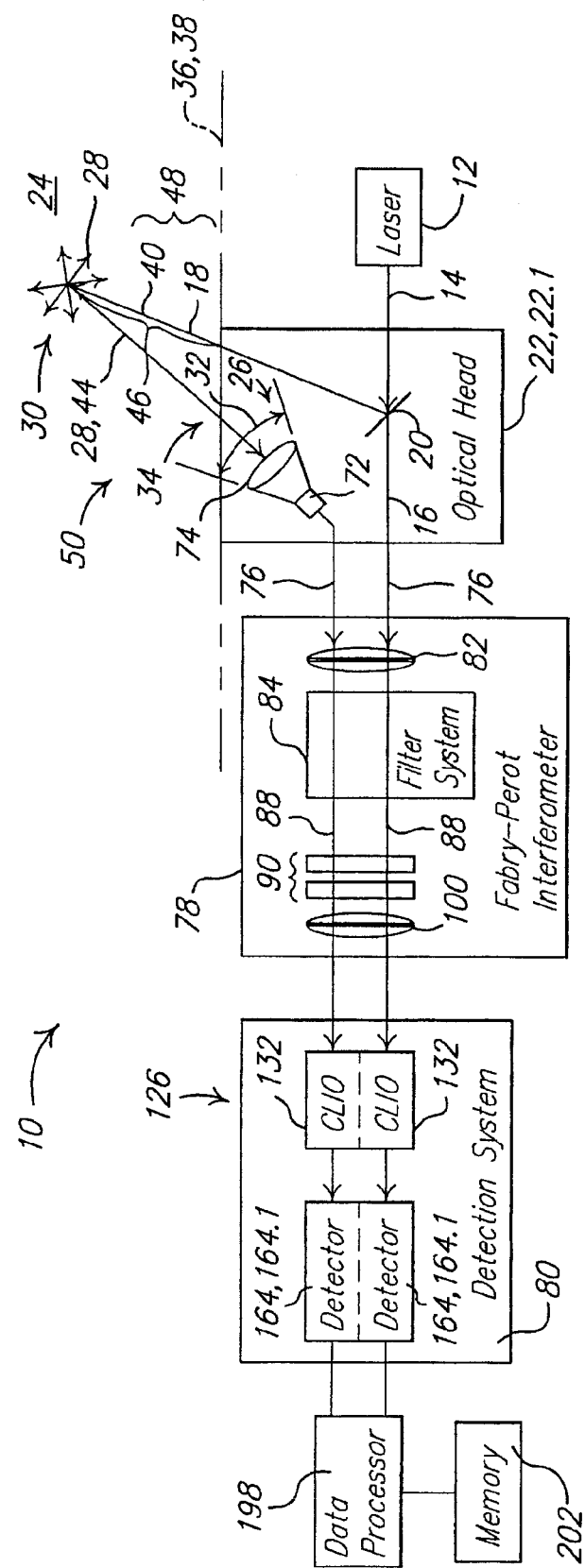
FIG. 1 illustrates a schematic block diagram of a molecular optical air data system.

Referring to FIG. 1, an optical air data system 10 comprises a laser 12 that generates a first laser beam 14 which is split into a reference beam 16 and one or more second laser beams 18 by a beam splitter optic 20 in an optical head 22. The optical head 22 provides for directing the one or more second laser beams 18 into an atmosphere 24 within sight thereof, and further incorporates a corresponding one or more telescopes 26, each associated with one of the one or more second laser beams 18, wherein each of the telescopes 26 provides for receiving light 28 that is backscattered by the atmosphere 24 from a corresponding interaction region 30 therein defined by the intersection of the associated second laser beam 18 with an associated field of view 32 of the corresponding telescope 26.

For example, in one embodiment, the first 14 and second 18 laser beams comprise ultraviolet (UV) laser light at a wavelength of about 266 nm that is emitted in three directions from surface-mounted apertures 34, for example, flush with a surface 36 of an aircraft 38, and the associated one or more telescopes 26 provide for detecting the return from scattering of the one or more second laser beams 18 by atmospheric molecules and aerosols. A wavelength of about 266 nm, being invisible to the human eye and substantially absorbed by the atmosphere, is beneficial for its stealth, eye safety and molecular scattering properties. There is very little natural background light due to absorption of most natural 266 nm light by ozone and molecular oxygen. Ultraviolet light at about 266 nm is readily absorbed by glass and plastic, such as used in aircraft wind screens, which provides for improved eye safety. The particular operating wavelength of the optical air data system 10 is not limiting, and it should be understood that any optical wavelength that interacts with that which is being sensed in the associated interaction region 30 may be used.

Figures 2A, 2B:
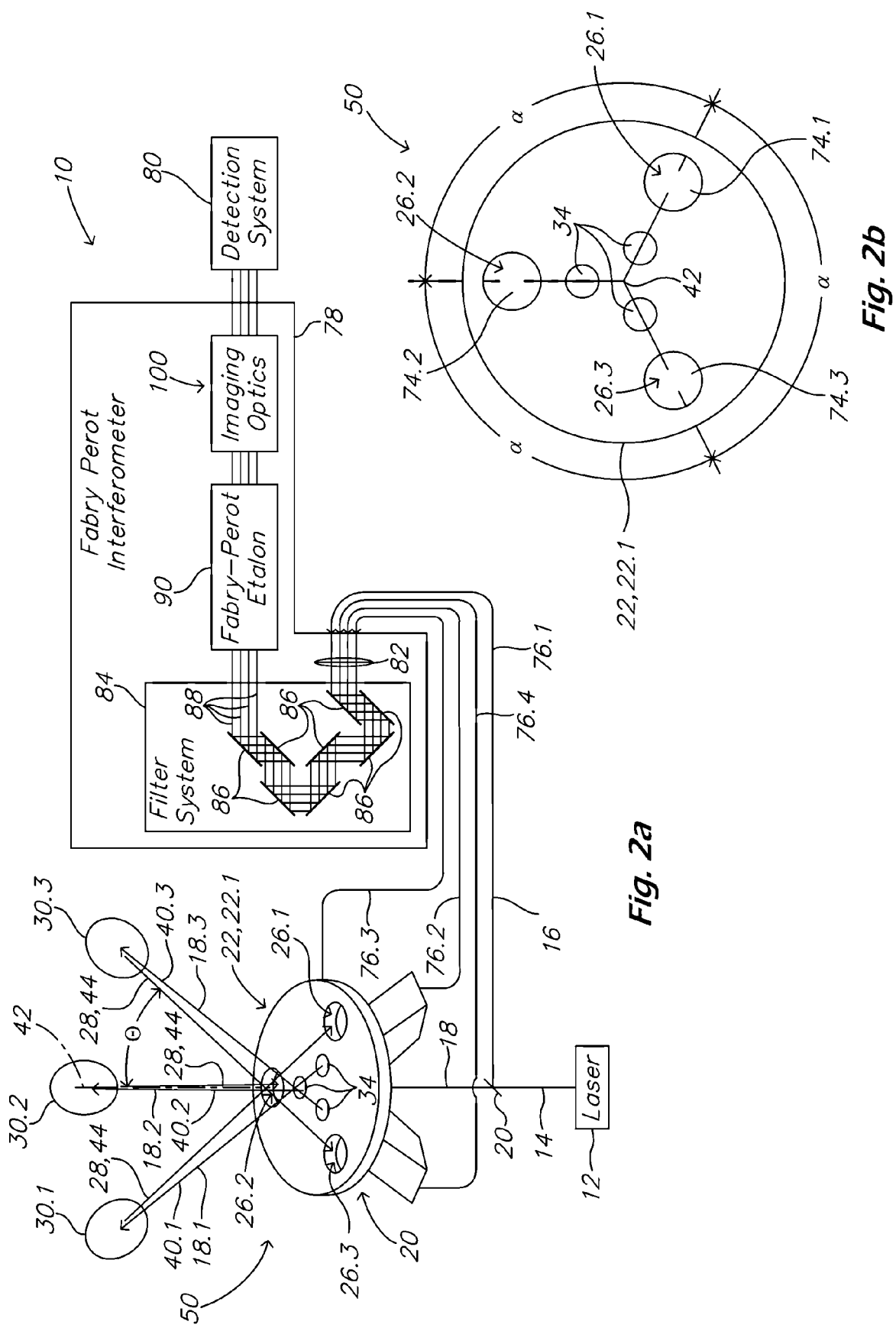
FIG. 2a illustrates several opto-mechanical elements of an optical air data system.
FIG. 2b illustrates a geometry of an embodiment of an optical head of an optical air data system.

Referring to FIGS. 2a and 2b, the optical head 22 provides for directing the outgoing one or more second laser beams 18, as well as collecting the backscattered signal, i.e. light 28, utilizing the corresponding associated separate telescopes 26. The optical head 22 can be custom-configured. For example, as illustrated in FIGS. 2a and 2b, proximate to the center of the optical head 22, the first laser beam 14 is divided using a beam splitter optic 20 into three separate second laser beams 18.1, 18.2 and 18.3, and then directed along three associated lines of sight 40: 40.1, 40.2 and 40.3, each spaced 120 degrees from each other and 30 degrees from a central axis 42. Light signals 44 are then collected by each telescope 26 of an array of three telescopes 26 built into the optical head 22. Plural channels oriented in different directions provide for calculating a wind or airspeed vector from the associated light signals 44, in addition to scalar properties of the atmosphere 24 in the associated interaction regions 30 along the associated lines of sight 40.

Each second laser beam 18 and its associated telescope 26 define a channel, and neither the number of channels, nor the geometry of the channels in relation to each other, is limiting. For example, although the embodiment illustrated in FIGS. 2a and 2b incorporates three channels, spaced 120 degrees apart from each other, other angles may be used to calculate a wind or airspeed vector. In addition, although three channels are necessary to calculate a wind or airspeed vector in 3-D space, the system may have extra redundant channels, dual channels to measure wind or airspeed in a particular plane, or single channels to measure the speed or properties of the atmosphere 24 along a specific line of sight of the associated telescope 26.

The optical air data system 10 is a laser remote sensing instrument that senses within the volume of the interaction region 30. The range 46 to the interaction region 30, e.g. the distance thereof from the surface 36 of the aircraft 38, is defined by the geometry of the associated second laser beam 18 and the corresponding telescope 26 as embodied in the optical head 22. The range 46 within the interaction region 30 can optionally be further resolved with associated temporal range gating, or range-resolved imaging, of the associated light signals 44 if desired or necessary for a particular application.

The optical air data system 10 is responsive substantially only to scattering from the interaction region 30 where the field of view 32 of the detecting telescope 26 and the second laser beam 18 overlap, and the geometry of the optical head 22 can be adapted to locate the interaction region 30 at substantially any distance, e.g. near or far, from the optical head 22 provided there is sufficient backscattered light 28 to be subsequently processed. For example, with the optical head 22 adapted to locate the interaction region 30 relatively far from the surface 36 of an aircraft 38, e.g. so as to be substantially not influenced by the turbulent region surrounding the aircraft 38, there would be substantially no signal from the associated near-field region 48 relatively proximate to the surface 36 of the aircraft 38 that would otherwise be affected, e.g. adversely, by the turbulent air stream therein.

Referring to FIGS. 1, 2a, 2b and 3, in accordance with a first aspect, each channel of the optical head 22.1 is adapted as a biaxial system 50 wherein, for a given channel, the associated second laser beam 18 and telescope 26 do not share a common axis. For example, at the optical head 22.1, the respective axes 52, 54 of the second laser beam 18 and telescope 26 are separated by an offset distance 56, and the axes 52, 54 are oriented at a relative angle 58 and directed so that the second laser beam 18 intersects the field of view 32 of the telescope 26 so as to define the associated interaction region 30. The length 60 of the interaction region 30 is defined between an entrance 62 where the second laser beam 18 enters the field of view 32 of the telescope 26, and an exit 64 where the second laser beam 18 exits the field of view 32 of the telescope 26, wherein the interaction region 30 is bounded by the second laser beam 18 between the associated entrance 62 and exit 64.

Figure 4:
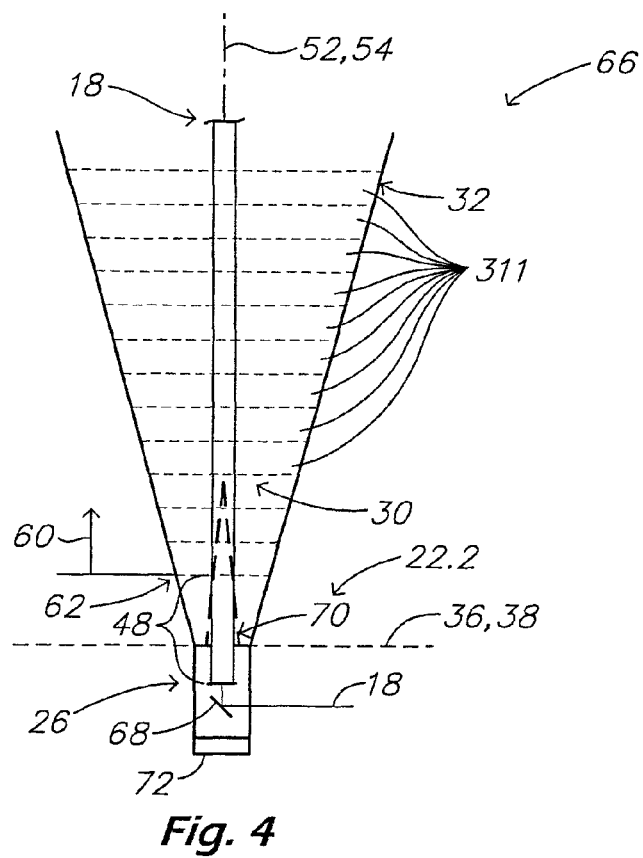
FIG. 4 illustrates an optical head of a coaxial system.

Referring to FIG. 4, in accordance with a second aspect, the optical head 22.2 is adapted as a coaxial system 66 wherein, for a given channel, the associated second laser beam 18 and telescope 26 substantially share a common axis 52, 54. For example, a mirror 68 located within a portion, e.g. a central portion, of the field of view 32 of the telescope 26. The second laser beam 18 is reflected off the mirror 68, and the mirror 68 is oriented so as to substantially align the axis 52 of the second laser beam 18 reflected from the mirror 68, with the axis 54 of the telescope 26. The mirror 68 partially obstructs the field of view 32 of the telescope 26, which provides for a near-field region 48 in the shadow 70 of the mirror 68 within which the second laser beam 18 is not visible to the telescope 26 and therefore outside the interaction region 30, thereby providing for substantially preventing any signal return from a prospective turbulent region proximate to the surface 36 of the aircraft 38 for an optical air data system 10 operatively associated therewith. The interaction region 30 extends from an entrance 62 where the size of second laser beam 18 exceeds the size of the shadow 70 in the near-field region 48, and therebeyond the interaction region 30 remains within the field of view 32 of the telescope 26. The interaction region 30 can then be tuned by adjusting the size of the central obstruction, the field of view 32 of the telescope 26, the divergence angle of the second laser beam 18, and by translating a final light-collecting element 72 of the telescope 26 along the axis 54 thereof so as to effectively change the field of view 32 of the telescope 26 and the focal plane for the final light-collecting element 72.

Each telescope 26 comprises a lens system 74, and the light signal 44 collected thereby is collected by the final light-collecting element 72 thereof into a fiber optic 76 that directs the returned photons to associated portions of a Fabry-Pérot interferometer 78 and an associated detection system 80 for processing thereby. The reference beam 16 from the laser 12 and beam splitter optic 20 is directed to a separate portion of the Fabry-Pérot interferometer 78 and an associated detection system 80 for simultaneous processing thereby.

The reference beam 16 and the light signal 44 from the lens system 74 are each collimated by a collimating lens 82 of the Fabry-Pérot interferometer 78 and then filtered by a filter system 84 which, for example, as illustrated in FIG. 2a, incorporates eight bandpass filter mirrors 86 having associated filter pass bands centered about the operating frequency of the laser 12—e.g. about 266 nm for the above-described embodiment—which provides for filtering out associated background light. The filter system 84 exhibits high out-of-band rejection, as well as low in-band attenuation, and the bandwidth of the filter system 84 is sufficiently narrow so as to substantially filter or remove components of solar radiation or stray light in the collected light signals 44, yet sufficiently broad so as to be substantially larger than the bandwidth of the thermally-broadened spectrum in combination with the largest expected associated Doppler shift. For example, in one embodiment, the filter system 84 is adapted so as to provide for maximum filtering of light frequencies that are outside the frequency band of interest, e.g. greater than about 2 nanometers above or below the nominal center frequency of the first laser beam 14.

Figure 7A:
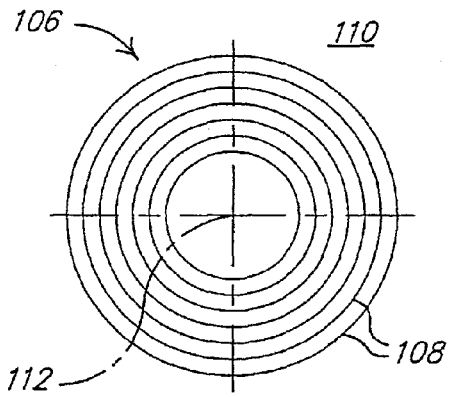
FIG. 7a illustrates fringes from a fully-illuminated Fabry-Pérot etalon.

Referring to FIGS. 1, 2a, 5a, 5b, 7a and 7b the light signals 88 from the filter system 84 are input to a Fabry-Pérot etalon 90 of the Fabry-Pérot interferometer 78, which provides for generating a fringe pattern 92 responsive to the optical frequency of the associated light signals 88, which optical frequency can exhibit a Doppler shift responsive to a relative velocity of the atmosphere 24 within the interaction region 30 from which the associated light 28 is backscattered. The Fabry-Pérot etalon 90 of the Fabry-Pérot interferometer 78 comprises first 94 and second 96 partially-reflective surfaces which are parallel to one another and separated by a fixed gap 98, and located between the collimating lens 82 and associated imaging optics 100. Light 102 at a focal plane 104 of the collimating lens 82 is substantially collimated thereby, and the angles at which the light 102 is passed through the Fabry-Pérot etalon 90 is dependent upon the optical frequency of the light 102, which, referring to FIG. 7a, becomes imaged as a circular fringe pattern 106—also known as Haidinger fringes—comprising a plurality of concentric circular fringes 108 in the focal plane 110 of the imaging optics 100. Referring to FIG. 7a, for a fully-illuminated Fabry-Pérot etalon 90, the resulting circular fringe pattern 106 is in the form of closed concentric circles centered about the optic axis 112 of the imaging optics 100.

For example, in the embodiment illustrated in FIGS. 1, 5a and 5b, the Fabry-Pérot etalon 90 comprises a pair of planar optical windows 114—for example, constructed of either optical glass or fused quartz—aligned parallel to and facing one another and spaced apart from one another by a gap 98, wherein, for example, the first 94 and second 96 partially-reflective surfaces are on separate facing surfaces of the planar optical windows 114, e.g. partially-silvered surfaces or other partially-reflective surfaces. Alternatively, the first 94 and second 96 partially-reflective surfaces could be on the outside opposing faces of the planar optical windows 114, or one of the first 94 and second 96 partially-reflective surfaces could be on a inner facing surface of one of the planar optical windows 114, and the other of the first 94 and second 96 partially-reflective surfaces could be on a outer facing surface of the other of the planar optical windows 114. In one embodiment, the gap 98 is substantially fixed, whereas in other embodiments, the gap 98 is moveable, e.g. adjustable, so as to provide for a tunable Fabry-Pérot etalon 90.

Figure 6:
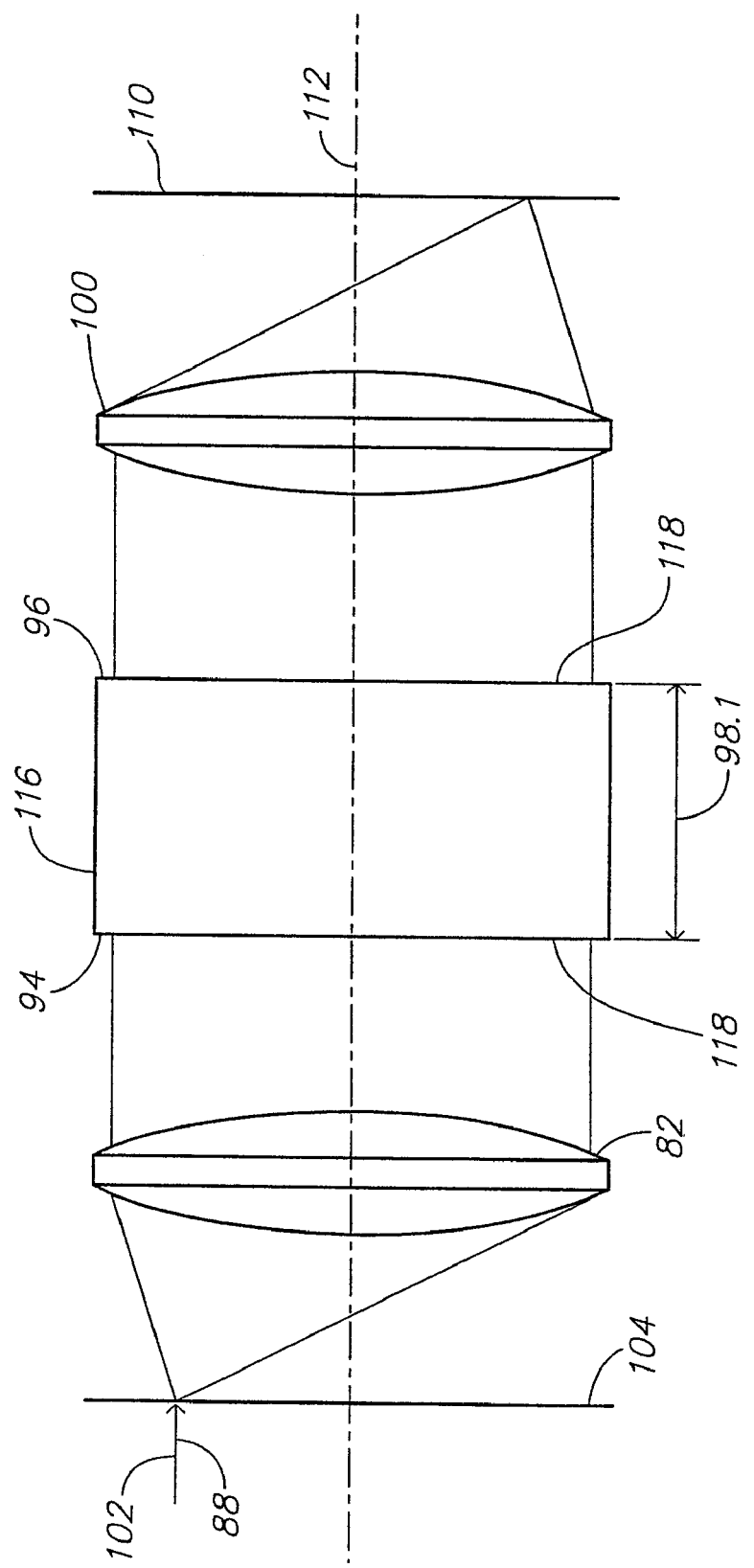
FIG. 6 illustrates a solid Fabry-Pérot etalon.

Referring to FIG. 6, alternatively, the Fabry-Pérot etalon 90 could comprise a solid optical element 116—for example, constructed of either optical glass or fused quartz—with planar parallel faces 118 comprising first 94 and second 96 partially-reflective surfaces separated by a gap 98.1 constituting the length of the solid optical element 116.

Figure 7B:
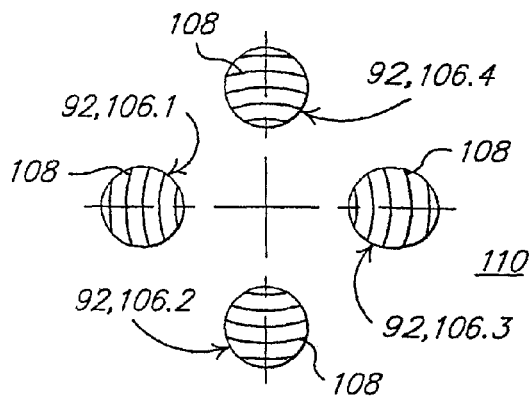
FIG. 7b illustrates fringes from a Fabry-Pérot etalon illuminated with four fiber input channels.

Referring to FIGS. 5a and 5b, the optical air data system 10 provides for an efficient use of the Fabry-Pérot etalon 90 by simultaneously processing a plurality of different channels of light 102 with a single, common Fabry-Pérot etalon 90. In one embodiment, a single Fabry-Pérot etalon 90 is used with four channels of light 102, i.e. a reference channel 120 from the reference beam 16, and three signal channels 122.1, 122.2 and 122.3 from the associated three lens systems 74.1, 74.2 and 74.3 associated with each of three telescopes 26.1, 26.2 and 26.3 having respectively three different lines of sight 40.1, 40.2 and 40.3. Referring also to FIG. 2a, respective fiber optics 76.1, 76.2, 76.3 and 76.4 receive light from the reference beam 16 and from each of the lens systems 74.1, 74.2 and 74.3, respectively, and illuminate corresponding portions of the Fabry-Pérot etalon 90 from respective off-axis locations 124.1, 124.2, 124.3 and 124.4 in the focal plane 104 of the collimating lens 82, producing associated images of partial circular fringe patterns 106.1, 106.2, 106.3 and 106.4, for example, as illustrated in FIGS. 5a and 7b.

The off-axis illumination of the Fabry-Pérot etalon 90 provides for increasing the geometric etendue of the optical air data system 10 than would result otherwise, wherein geometric etendue G characterizes the ability of an optical system to accept light. Geometric etendue G is defined as a product of the area A of the emitting source and the solid angle Ω into which the light therefrom propagates, i.e. (G=A*Ω). Geometric etendue G is a constant of the optical system, and is determined by the least optimized portion thereof. For a fixed divergence and aperture size of the associated fiber optic 76, for a given value of geometric etendue G, the area A of the emitting source (i.e. that of the fiber optic 76)—and the associated diameter of the optical system—may be reduced by increasing the solid angle Ω, i.e. the divergence of the associated optical system, so as to provide for reducing the size of the associated optical system without sacrificing performance. Alternatively, for a given area A and associated diameter of the optical system, the geometric etendue G of the optical system may be increased by increasing the solid angle Ω. For a Fabry-Pérot interferometer 78, increasing the angular divergence, i.e. solid angle Ω, of the associated optical system provides for a greater fraction and/or number of circular fringes 108. The optical air data system 10 simultaneously processes a reference channel 120 and one or more signal channels 122.1, 122.2 and 122.3 using a common Fabry-Pérot etalon 90, each channel 120, 122.1, 122.2 and 122.3 occupying a separate portion of the Fabry-Pérot etalon 90, the collection of channels 120, 122.1, 122.2 and 122.3 thereby necessitating a larger-diameter Fabry-Pérot etalon 90 than would be required otherwise if only a single channel 120, 122.1, 122.2 or 122.3 were to be processed thereby. Accordingly associated respective off-axis locations 124.1, 124.2, 124.3 and 124.4 of the respective fiber optics 76.1, 76.2, 76.3 and 76.4 provides for both simultaneously accommodating the plurality of fiber optics 76.1, 76.2, 76.3 and 76.4 input to the common Fabry-Pérot etalon 90, and provides for increasing the associated angular divergence through the optical system which provides for either relatively increasing the geometric etendue G and associated light gathering capability of the of the associated optical system for a given-sized optical system, or for relatively decreasing the size (i.e. diameter) of the optical system for a given geometric etendue G thereof.

Signals from the signal channel 122.1, 122.2 or 122.3 for each of the associated interaction regions 30 are substantially simultaneously processed together with a signal from the reference channel 120 so as to provide for calibrating, and maintaining the calibration of, the optical air data system 10, and so as to provide for determining the associated air data products such as the speed, temperature and density of the atmosphere 24. This provides for an inherent self-calibration of the associated measurements or quantities derived therefrom. If wavelength drift of the first laser beam 14 is not otherwise accounted for in the data, then errors can arise when making a measurement of the Doppler shift and resulting wavelength shift of the signal channels 122.1, 122.2 and 122.3. The optical air data system 10 provides for automatically compensating for wavelength drift of the first laser beam 14 from the data because each measurement from a signal channel 122.1, 122.2 or 122.3 is corrected using a corresponding measurement from the reference channel 120 associated with the reference beam 16.

Figure 8:
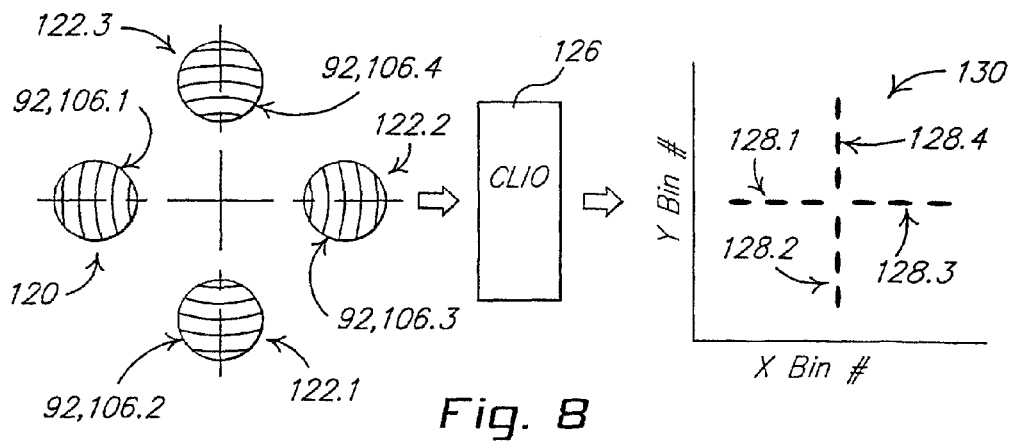
FIG. 8 illustrates four channels of fringes being collapsed by a quad circle-to-line interferometer optic (quad-CLIO) to four lines in the shape of a cross-pattern on an opto-electric detector.

Referring to FIG. 8, in one embodiment, a quad circle-to-line interferometer optic 126 (quad-CLIO 126) is used to transform the four channels 120, 122.1, 122.2 and 122.3 of circular fringe patterns 106.1, 106.2, 106.3 and 106.4 into four associated linear fringe patterns 128.1, 128.2, 128.3 and 128.4, forming a cross pattern 130. The quad-CLIO 126 comprises four circle-to-line interferometer optic 132 (CLIO 132) elements, each associated with a different one of the four channels 120, 122.1, 122.2 and 122.3 of circular fringe patterns 106.1, 106.2, 106.3 and 106.4.

Figure 9:
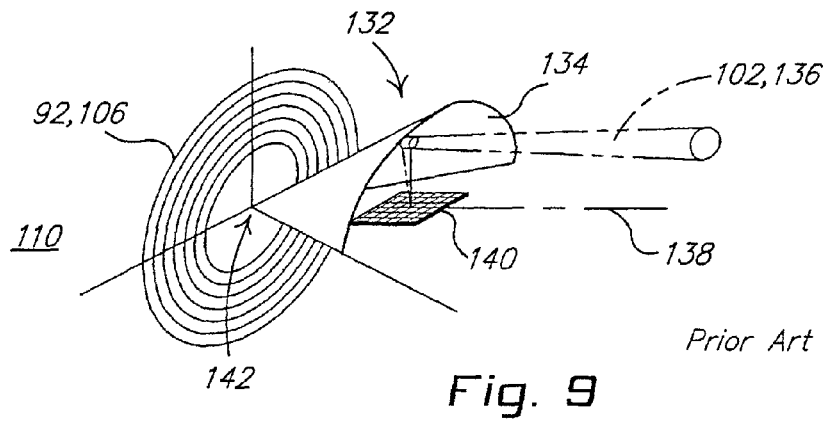
FIG. 9 illustrates a prior art circle-to-line interferometer optic (CLIO)
Figure 10:
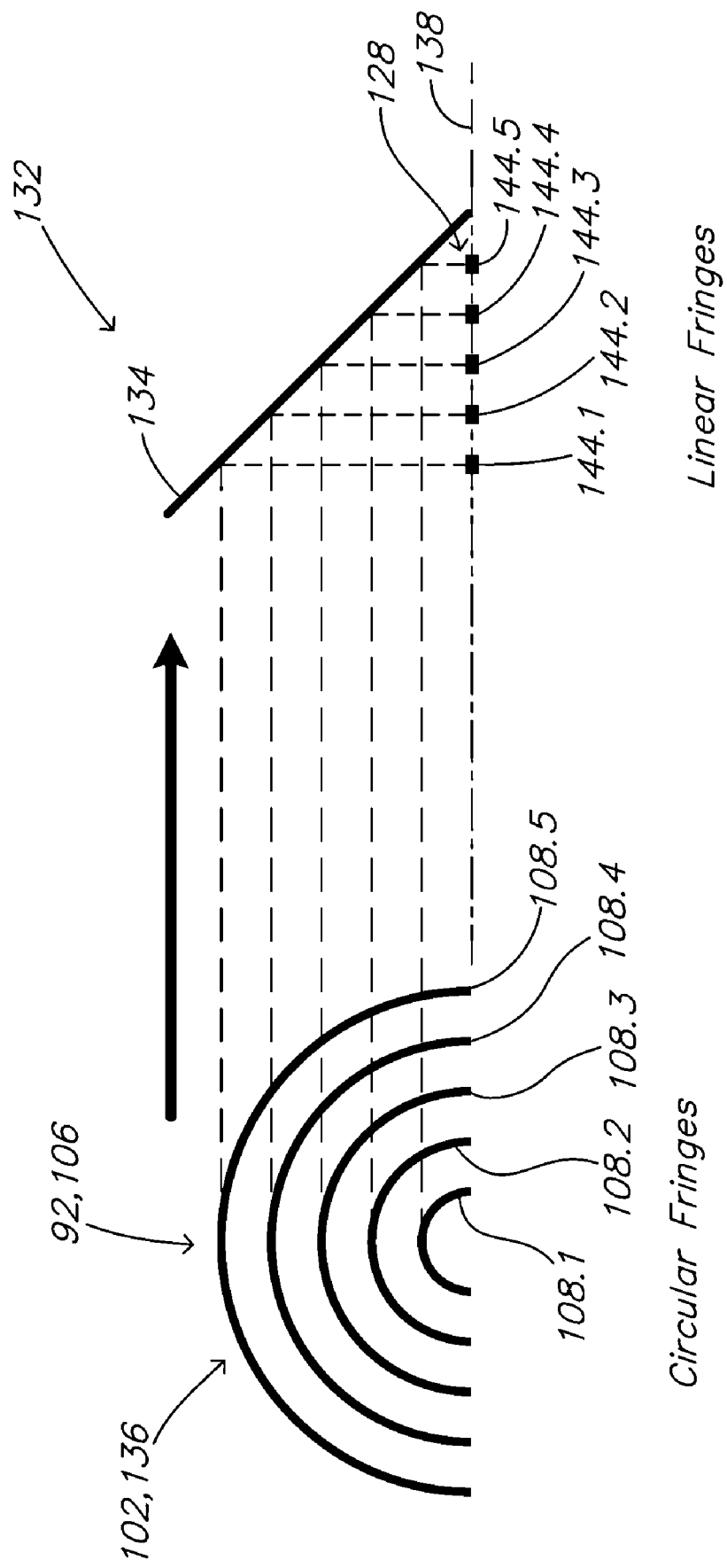
FIG. 10 illustrates the operation of a circle-to-line interferometer optic (CLIO)
Figure 11:
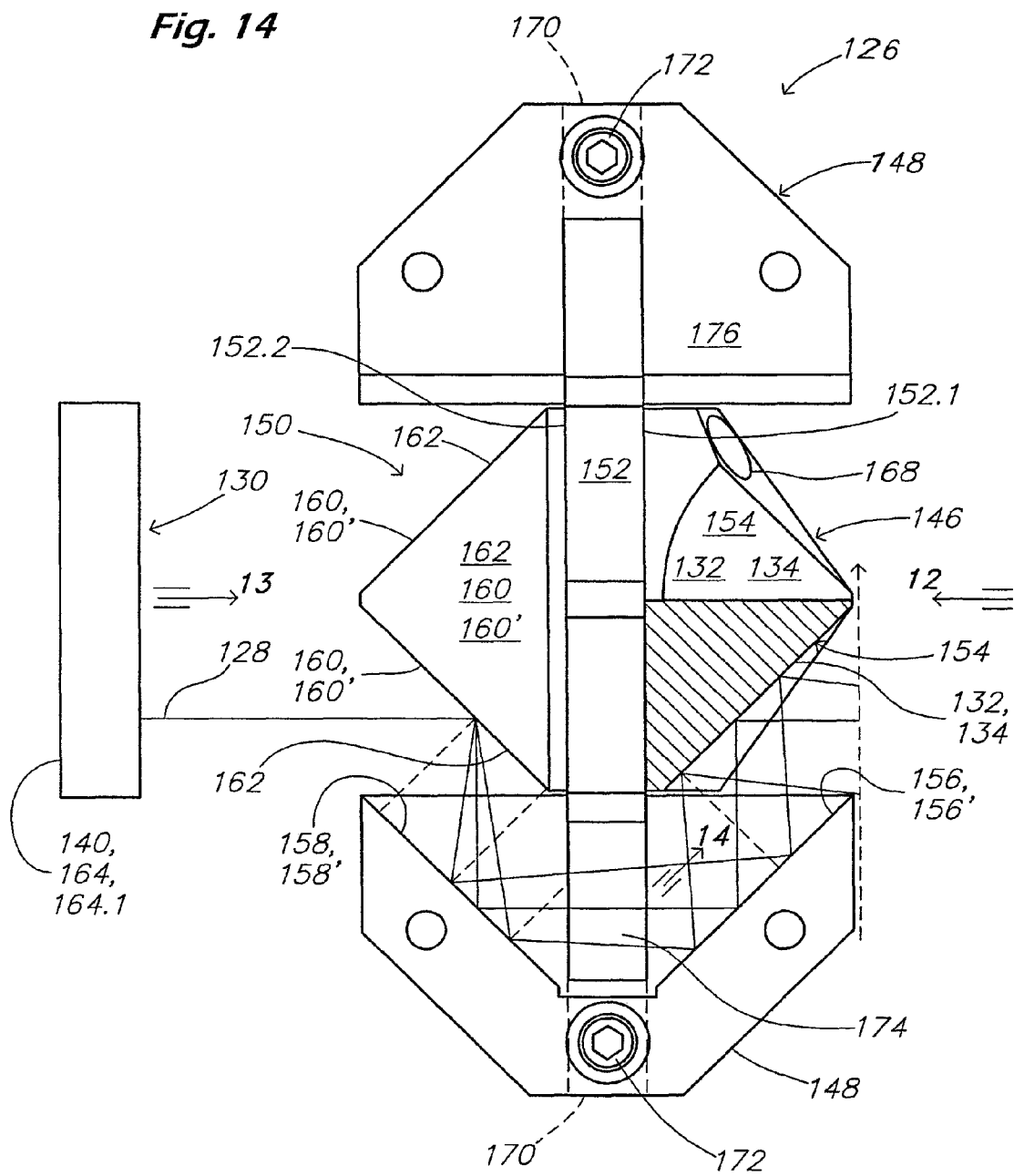
FIG. 11 illustrates a side view of a quad-CLIO element and an associated detector.
Figure 12:
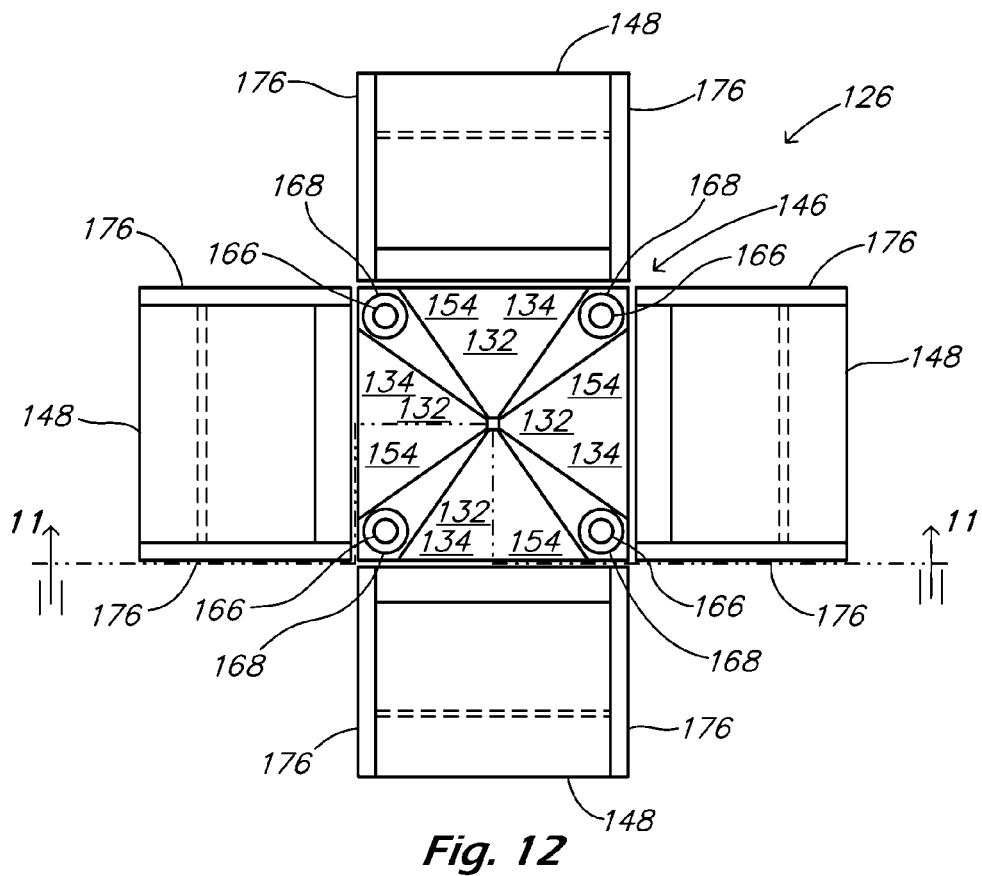
FIG. 12 illustrates a plan view of the quad-CLIO element illustrated in FIG. 11, viewed from the side of an associated first pyramidal shaped optic element.
Figure 13:
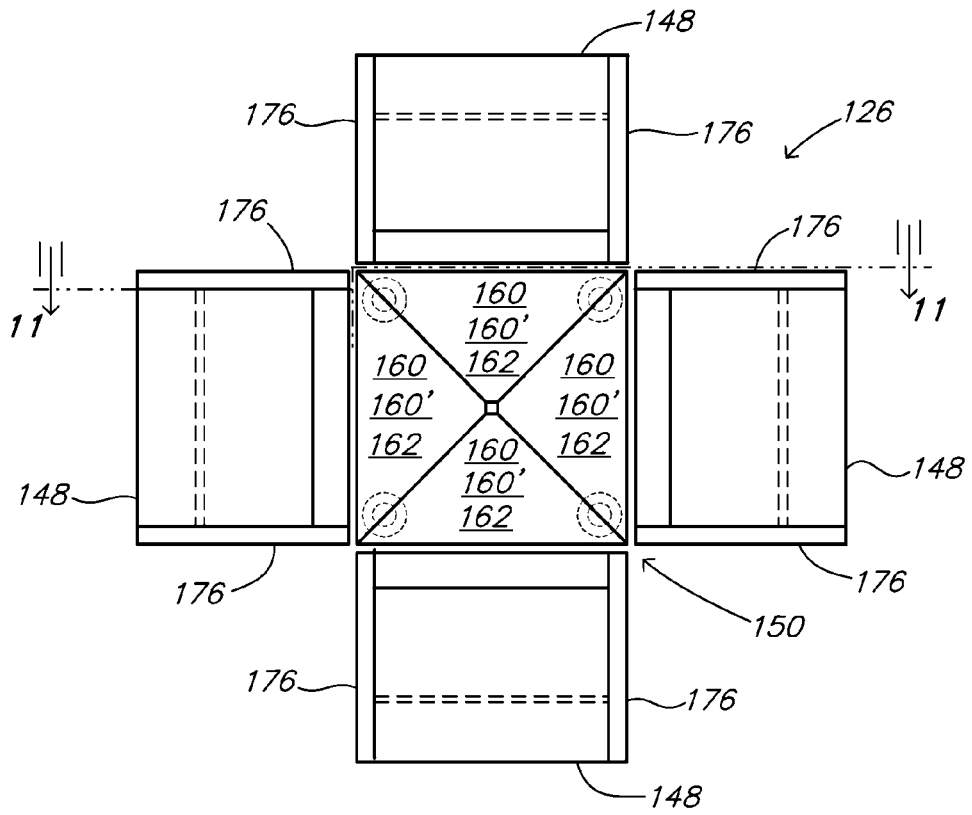
FIG. 13 illustrates a plan view of the quad-CLIO element illustrated in FIG. 11, viewed from the side of an associated second pyramidal shaped optic element.

Referring to FIG. 9, a circle-to-line interferometer optic 132 (CLIO 132), described in U.S. Pat. No. 4,893,003, the entire content of which is incorporated herein by reference, comprises a concave conical reflector 134, the surface of which is a conical segment constituting a section of the underlying conical surface. Electromagnetic energy 136 from the Fabry-Pérot interferometer 78—constituting the circular fringe pattern 106 to be transformed—is propagated substantially parallel to the conical axis 138 of the underlying conical surface, and is reflected and focused by the concave conical reflector 134 substantially onto a linear detector 140 substantially along or proximate to the conical axis 138. In one embodiment, the apex 142 of the underlying conical surface is situated where the conical axis 138 intersects the focal plane 110 of the circular fringe pattern 106. Referring to FIG. 10, the CLIO 132 transforms each circular fringe 108, e.g. 108.1, 108.2, 108.3, 108.4 and 108.5, into a corresponding spot 144, e.g. 144.1, 144.2, 144.3, 144.4 and 144.5 of an associated linear fringe pattern 128, thereby concentrating the associated electromagnetic energy 136 so as to improve the associated signal to noise ratio of the associated detection process by the associated linear detector 140. Accordingly, each CLIO 132 provides for transforming a circular fringe pattern 106 into a corresponding linear fringe pattern 128 substantially along the associated conical axis 138 so as to provide for using a linear detector 140 array—for example, a charge-coupled device (CCD), e.g. as used in spectroscopic analysis—to detect the light of the linear fringe pattern 128.

Referring to FIGS. 11-14, for example, in one embodiment, the quad-CLIO 126, comprises a first pyramidal shaped optic element 146 which cooperates with a plurality of corner reflector optic elements 148, which in turn cooperate with a second pyramidal shaped optic element 150, all of which are operatively coupled to an associated base plate 152. Each side face 154 of the first pyramidal shaped optic element 146 incorporates an associated concave conical reflector 134 adapted to receive an associated circular fringe pattern 106.1, 106.2, 106.3 and 106.4 from the Fabry-Pérot interferometer 78, wherein different concave conical reflectors 134 are adapted to receive different respective circular fringe patterns 106.1, 106.2, 106.3 and 106.4. A light signal 88 of the circular fringe pattern 106.1, 106.2, 106.3, 106.4 is reflected from the corresponding concave conical reflector 134 onto a first reflective surface 156 of a corresponding corner reflector optic element 148, and then reflected therefrom onto a second reflective surface 158 of the corresponding corner reflector optic element 148, and then reflected therefrom onto a third reflective surface 160 on a side face 162 of the second pyramidal shaped optic element 150, and finally reflected therefrom onto an associated detector 164, for example, an associated array of linear detectors 140. For example, in one embodiment, the first 156, second 158 and third 160 reflective surfaces comprise corresponding planar reflective surfaces 156', 158' and 160'. The first 146 and second 150 pyramidal shaped optic elements are secured to and aligned with one another on opposite faces 152.1, 152.2 of the base plate 152, for example, with fasteners 166, e.g. machine screws, extending through associated counterbores 168 in the first pyramidal shaped optic element 146, through the base plate 152, and into the second pyramidal shaped optic element 150. The corner reflector optic elements 148 are fastened to tongue portions 170 of the base plate 152 with associated fasteners 172, which provide for a rotational adjustment of the corner reflector optic elements 148. The base plate 152 is adapted with a plurality of openings 174 so as to provide for optical communication between the first 156 and second 158 reflective surfaces. Each corner reflector optic element 148 incorporates a pair of side plates 176 which provide for shielding stray light and for improved structural integrity. In another embodiment, one or more corner reflector optic elements 148 could be replaced with separate elements for each of the associated first 156 and second 158 reflective surfaces. The first 146 and second 150 pyramidal shaped optic elements and the corner reflector optic elements 148 can be constructed from a variety of materials—including, but not limited to, aluminum, stainless steel, copper-nickel alloy, glass or fused quartz—that can be adapted to incorporate associated reflective surfaces or coatings.

Accordingly, the quad-CLIO 126 comprises a tele-kaleidoscope having a predetermined arrangement of mirrors adapted to provide for compressing the azimuthal angular extent of the partial circular fringe patterns 106.1, 106.2, 106.3 and 106.4 into associated linear fringe patterns 128.1, 128.2, 128.3 and 128.4 forming a cross pattern 130. The circular fringe patterns 106.1, 106.2, 106.3 and 106.4 generated by the Fabry-Pérot interferometer 78 are transformed by the quad-CLIO 126 into a linear cross pattern 130 which is then imaged onto a detector 164. For example, the detector 164 may comprise one or more charge-coupled devices (CCD), i.e. a CCD detector 164.1, a set of linear arrays, one or more photomultiplier tubes, a plurality of avalanche photo diodes, or any other multi-element detection device that converts photons to electrons. For example, a CCD detector 164.1 can be adapted to be low-light sensitive, and can provide for provide a low noise image readout. A quad-CLIO 126, although not essential, can provide for enhancing the associated signal to noise ratio, and by providing for detection using readily-available linear-based detectors such as a linear array or CCD, can provide for improving the overall efficiency and simplicity of the signal detection process.

Referring to FIGS. 15a and 15b, the detector 164 generates an image signal 178 of the cross pattern 130 transformed by the quad-CLIO 126, wherein the image signal 178 comprises an array of pixels 180. The efficiency of the detection process can be increased by binning the image signal 178 during the associated detection process, wherein the plurality pixel values of a plurality of adjacent pixels 180 are replaced with a single sum of the plurality of pixel values. For example, for a Cartesian array of pixels 180, generally the binning process can operate in either of the associated Cartesian directions, or in both directions. For example, binning is a standard process for use with CCD devices wherein pixel charges are summed together on chip, so as to provide for reducing the relative amount of read-noise associated with the analog-to-digital conversion (A/D) process that occurs when pixel charges are read off of the CCD detector 164.1, for example, by summing a plurality of rows of pixels 180 together so as to limit the number of rows or columns undergoing an A/D conversion.

Referring to FIGS. 15a and 15b, in accordance with a first embodiment, an optical air data system 10 incorporates a quad-CLIO 126 and a custom-binning pattern is utilized to efficiently detect the associated cross pattern 130, using a cross-binning process that provides for multi-axis binning within selected sub-regions of interest on the CCD detector 164.1. For the cross-binning algorithm, respective regions of interest 182.1, 182.2, 182.3 and 182.4 are defined for each respective channel 120, 122.1, 122.2 and 122.3 comprising one leg 184.1, 184.2, 184.3, 184.4 of the associated cross pattern 130. Photo-electric generated charges collected on the CCD detector 164.1 within each region of interest 182.1, 182.2, 182.3, 182.4 are binned, i.e. summed, by the CCD detector 164.1 for each channel 120, 122.1, 122.2 and 122.3 along the width 186 of the corresponding leg 184.1, 184.2, 184.3, 184.4 of the associated cross pattern 130, so as to compress the array of pixels 180 associated with each leg 184.1, 184.2, 184.3, 184.4 of the associated cross pattern 130 into a corresponding line of binned pixels 188.1, 188.2, 188.3, 188.4 of the same length as the corresponding leg 184.1, 184.2, 184.3, 184.4, but only one binned pixel 190 wide, with the value of each binned pixel 190 equal to the sum of the values of the corresponding pixels 180 across the corresponding leg 184.1, 184.2, 184.3, 184.4 at a position 192 along the leg 184.1, 184.2, 184.3, 184.4 corresponding to the position 192 of the corresponding binned pixel 190 along the corresponding line of binned pixels 188.1, 188.2, 188.3, 188.4, thereby providing for reducing the overall read noise associated with reading the lines of binned pixels 188.1, 188.2, 188.3, 188.4 relative to that associated with reading a greater number of pixels 180 in the original legs 184.1, 184.2, 184.3, 184.4 of the associated cross pattern 130, because of the reduction in the number of pixels being read and the greater value of each binned pixel 190 relative to that of the corresponding pixels 180 of the original image signal 178.

Referring to FIGS. 16a and 16b, in accordance with a second embodiment, the optical air data system 10 is adapted so as to provide for directly processing the associated circular fringe patterns 106.1, 106.2, 106.3 and 106.4 from the Fabry-Pérot interferometer 78 without utilizing an associated quad-CLIO 126, whereby the circular fringe patterns 106.1, 106.2, 106.3 and 106.4 are imaged directly upon the associated CCD detector 164.1, and a circular binning algorithm then sums all pixels 180 at a particular radius 194 from the common center 196 of the circular fringe patterns 106.1, 106.2, 106.3 and 106.4. For example, the circular binning algorithm could be implemented by a data processor 198—for example, in software therein—operatively coupled to the associated CCD detector 164.1, or to an associated plurality of CCD detectors 164.1, each adapted to detect one or more of the associated circular fringe patterns 106.1, 106.2, 106.3 and 106.4. After identifying the center 196 of the circular fringe patterns 106.1, 106.2, 106.3 and 106.4, the circular binning algorithm sums up the CCD charges (i.e. pixel values) for each pixel 180 at a particular radius from the center 196, for a particular circular fringe pattern 106.1, 106.2, 106.3, 106.4, for each of the circular fringe patterns 106.1, 106.2, 106.3 and 106.4, so as to provide a respective associated line of binned pixels 188.1, 188.2, 188.3, 188.4 for each of the respective circular fringe patterns 106.1, 106.2, 106.3 and 106.4. Compared with the first embodiment operative with a quad-CLIO 126 and an associated cross-binning process operative within the CCD detectors 164.1, wherein the charges for pixels 180 to be binned are summed before readout of the resulting corresponding binned pixel 190, the circular binning process of the second embodiment provides for reading the pixels 180 before binning, whereby each pixel 180 is read from the CCD detector 164.1 and converted by an A/D conversion process, which results in a greater amount of overall read noise than would occur with the first embodiment, although the overall noise level can be kept to within acceptable levels by using a relatively low-noise CCD detector 164.1. The ratio of signal to read noise can be enhanced by increasing the exposure time of the CCD detector 164.1 between read cycles, although at the cost of reduced dynamic frequency response of the associated resulting air data products.

Figure 17:
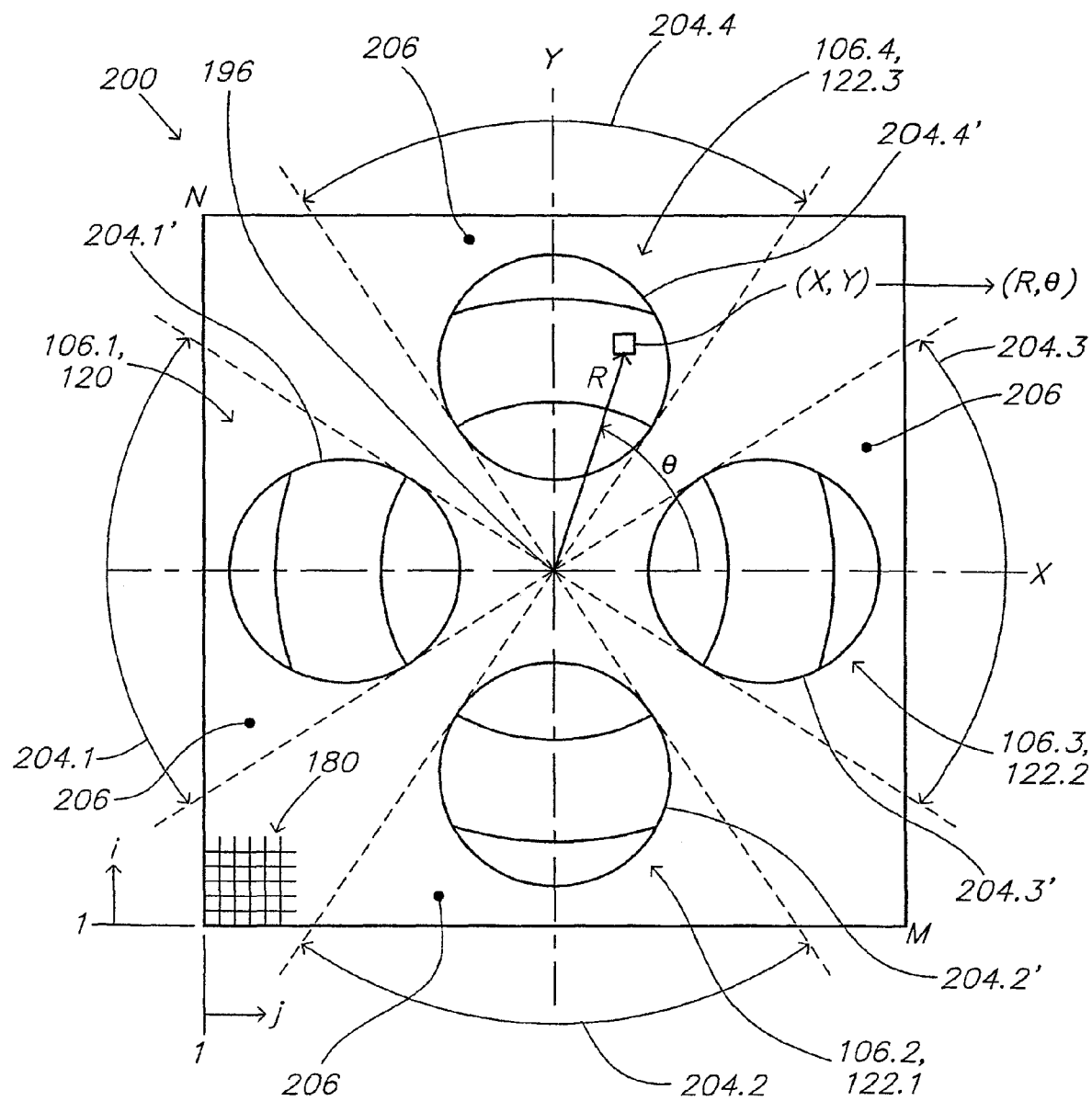
FIG. 17 illustrates an image of a set of circular fringe patterns and regions of interest associated with a circular binning process.

Referring to FIG. 17, an image 200 of a set of circular fringe patterns 106.1, 106.2, 106.3 and 106.4 comprises an array of N rows by M columns of pixels 180, each of which is captured by an associated detector 164 and stored in a memory 202 of the associated data processor 198 of the optical air data system 10. The image 200 comprises four regions of interest (ROI) 204.1, 204.2, 204.3 and 204.4, each comprising a segment 206 containing an associated circular fringe pattern 106.1, 106.2, 106.3 and 106.4, and centered about the common center 196 of the circular fringe patterns 106.1, 106.2, 106.3 and 106.4, wherein the center 196 of the circular fringe patterns 106.1, 106.2, 106.3 and 106.4 is determined upon initial calibration or subsequent recalibration of the associated optical air data system 10, and is assumed to be stationary during the operation thereof. For example, the center 196 may be determined by recording a substantial number, e.g. thousands, of circular fringe patterns 106.1, 106.2, 106.3 and 106.4 and determining the location of the center 196—by either iteration starting with an initial guess, or least squares or correlation with the coordinates of the center 196 as unknowns to be determined—that provides for a best fit of the recorded circular fringe patterns 106.1, 106.2, 106.3 and 106.4 with a corresponding circular model thereof centered at the center 196 of the circular fringe patterns 106.1, 106.2, 106.3 and 106.4.

Figure 18A:
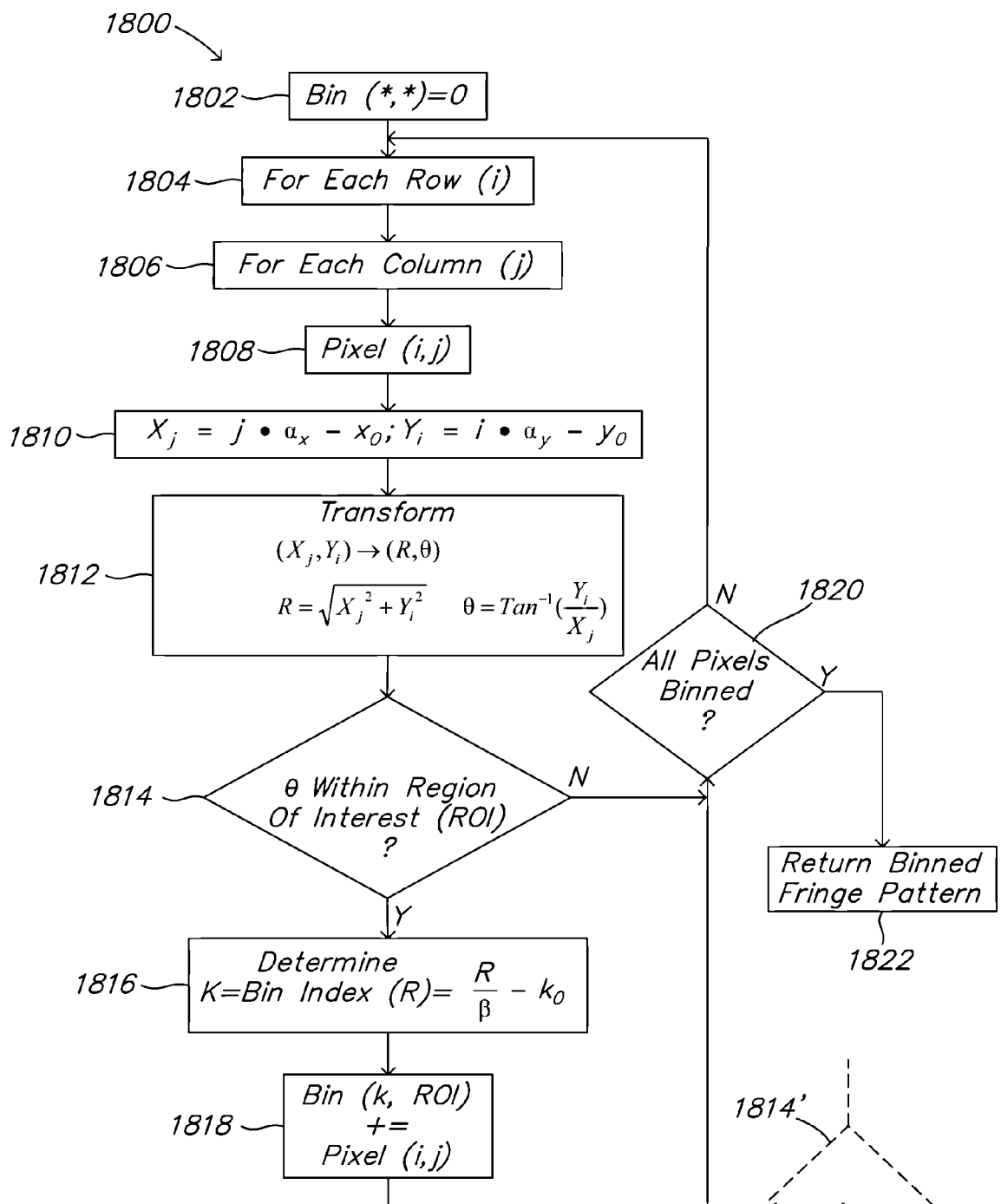
FIG. 18a illustrates a flow chart of a first embodiment of a circular binning process.

Referring to FIG. 18a, in accordance with a first embodiment of a circular binning process 1800, in step (1802) a K×NROI bin array BIN(*,*) is defined with storage for NROI vectors of K elements each to hold the circumferentially-binned values for each of the NROI=4 circular fringe patterns 106.1, 106.2, 106.3 and 106.4, and each value thereof is initialized to zero. Then, in steps (1804) and (1806), for each row i of the N rows, and for each column j of the M columns, of the pixels 180 in the image 200, the value Pixel(i,j) of the pixel 180 is read from the image 200 in step (1808), and in step (1810), the corresponding X and Y locations thereof are calculated respectively as follows:

$$x_j = j \cdot \alpha_X - x_0$$
$$y_i = i \cdot \alpha_Y - y_0 \quad (1)$$

wherein $\alpha_X$ and $\alpha_Y$ are the distances per pixel in the X and Y directions, respectively, and $x_0$ and $y_0$ are the coordinates of the center 196 relative to Pixel(1,1) at the lower left corner of the image 200. Then, in step (1812), the Cartesian coordinates $(x_j,y_i)$ from step (1810) are transformed to cylindrical coordinates $(R,\theta)$, as follows:

$$R = \sqrt{x_j^2 + y_i^2} \quad (2)$$
$$\theta = \mathrm{Tan}^{-1}\left(\frac{y_i}{x_j}\right)$$

Then, in step (1814), if the angle $\theta$ is within a region of interest (ROI) 204.1, 204.2, 204.3 and 204.4, the associated region of interest ROI is identified, and in step (1816), the radial bin index k is given by:

$$k = \frac{R}{\beta} - k_0 \quad (3)$$

where $\beta$ is the distance per pixel in the radial direction, and $k_0$ is the number of pixels 180 between the center 196 and the closest portion of the circular fringe pattern 106.1, 106.2, 106.3 and 106.4 closest thereto. Then, in step (1818), the associated value Pixel(i,j) of the associated pixel 180 is added to the bin element BIN(k,ROI) of the bin array BIN(,) as follows:

$$\mathrm{BIN}(k,\mathrm{ROI}) = \mathrm{BIN}(k,\mathrm{ROI}) + \mathrm{Pixel}(i,j) \quad (4)$$

Then, or otherwise from step (1814), in step (1820), if all of the pixels 180 have been circumferentially binned, then, in step (1822), the circumferentially-binned values for each of the circular fringe patterns 106.1, 106.2, 106.3 and 106.4 are returned in the associated bin array BIN(*,NROI). Otherwise, the process repeats with steps (1804) and (1806) for each of the rows and columns of pixels 180 until all of the circular fringe patterns 106.1, 106.2, 106.3 and 106.4 are binned.

Figure 18B:
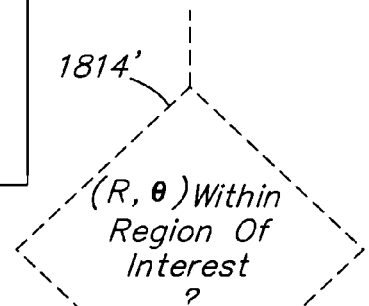

Referring to FIGS. 17 and 18b, alternatively, regions of interest (ROI) 204.1', 204.2', 204.3' and 204.4' may be defined by the corresponding respective circular boundaries of the respective circular fringe patterns 106.1, 106.2, 106.3 and 106.4, in which case, step (1814) of the circular binning process 1800 would be replaced by step (1814'), whereby the test as to whether a particular pixel 180 was in a particular regions of interest (ROI) 204.1', 204.2', 204.3' and 204.4' would depend upon both cylindrical coordinates $(R,\theta)$ of the particular pixel 180.

Figure 19:
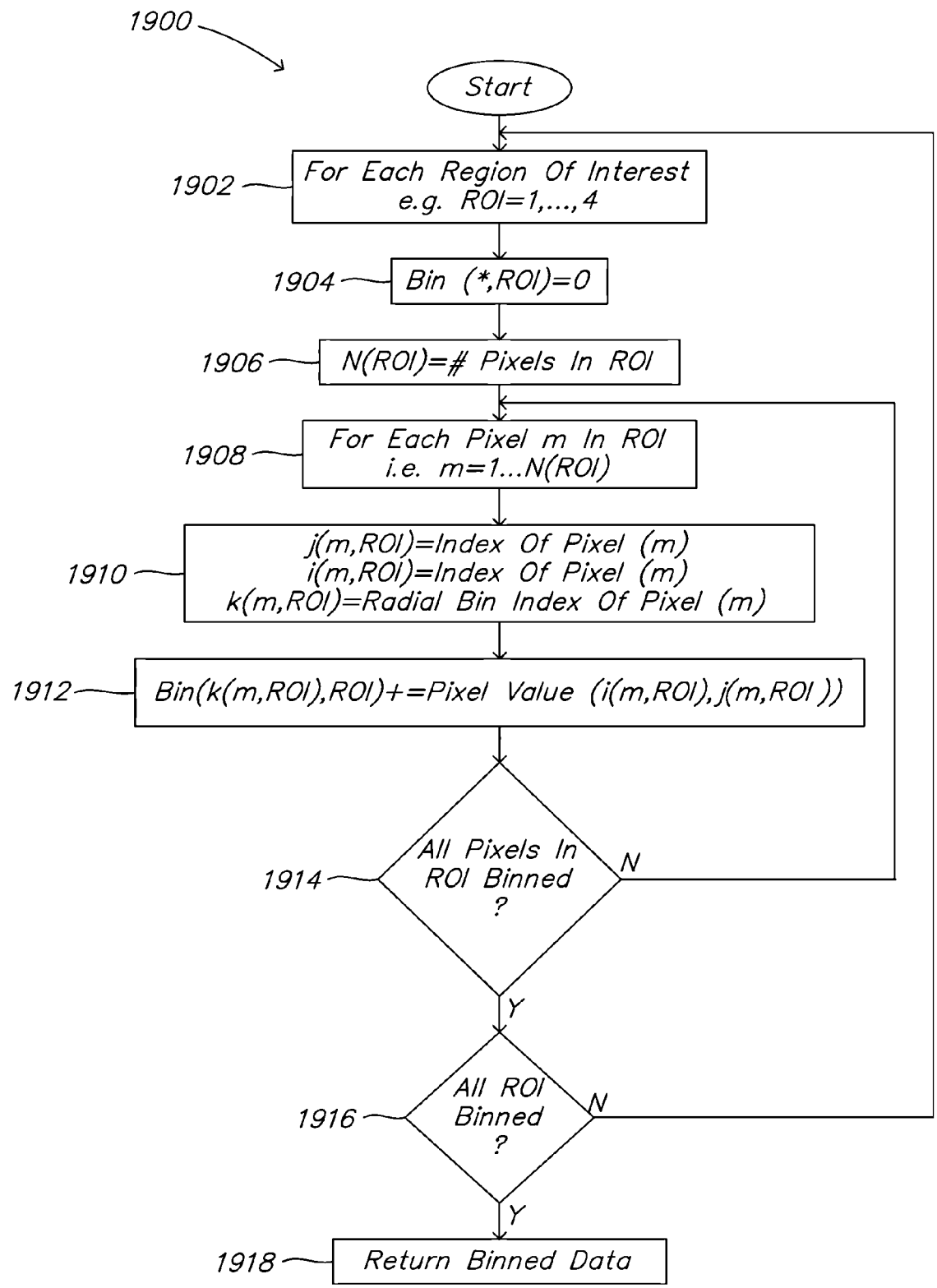
FIG. 19 illustrates a flow chart of a second embodiment of a circular binning process.

Referring to FIG. 19, in accordance with a second embodiment of a circular binning process 1900, rather than processing every pixel 180 of the image 200, only those pixels 180 in predefined regions of interest (ROI) 204.1', 204.2', 204.3' and 204.4' are processed, wherein, for example, the regions of interest (ROI) 204.1', 204.2', 204.3' and 204.4' are defined by the corresponding respective circular boundaries of the respective circular fringe patterns 106.1, 106.2, 106.3 and 106.4. Beginning with step (1902), for each regions of interest (ROI) 204.1', 204.2', 204.3', 204.4', in step (1904) the associated bin elements BIN(*,ROI) are initialized to zero. Then, in step (1906), the number of pixels 180 in the particular region of interest (ROI) 204.1', 204.2', 204.3', 204.4' is given by the predetermined value of N(ROI). Then in step (1908), for pixel m of the N(ROI) pixels 180 in the particular region of interest (ROI) 204.1', 204.2', 204.3', 204.4', the corresponding column j and row i indexes for the particular pixel 180, corresponding to the associated X and Y locations thereof, are given in step (1910) by predetermined values from predetermined index arrays j(m,ROI) and i(m,ROI) respectively, and the corresponding element k of the associated bin array BIN(*,ROI) into which the particular pixel 180 is to be binned is given by the predetermined index array k(m,ROI). Accordingly, in step (1912), the $m^{th}$ pixel 180 is binned into the $k^{th}$ element of the bin array BIN(*,ROI) as follows:

$$\text{BIN}(k(m,\text{ROI}),\text{ROI}) = \text{BIN}(k(m,\text{ROI}),\text{ROI}) + \text{Pixel}(i(m,\text{ROI}),j(m,\text{ROI})) \quad (5)$$

Then, in step (1914), if all of the pixels m in the particular region of interest ROI have not been binned, then the process continues with step (1908). Otherwise, in step (1916), if all of the regions of interest (ROI) 204.1', 204.2', 204.3' and 204.4' have not been binned, then the process continues with step (1902). Otherwise, in step (1918), the circumferentially-binned values for each of the circular fringe patterns 106.1, 106.2, 106.3 and 106.4 are returned in the associated bin array BIN(*,NROI).

Figure 20:
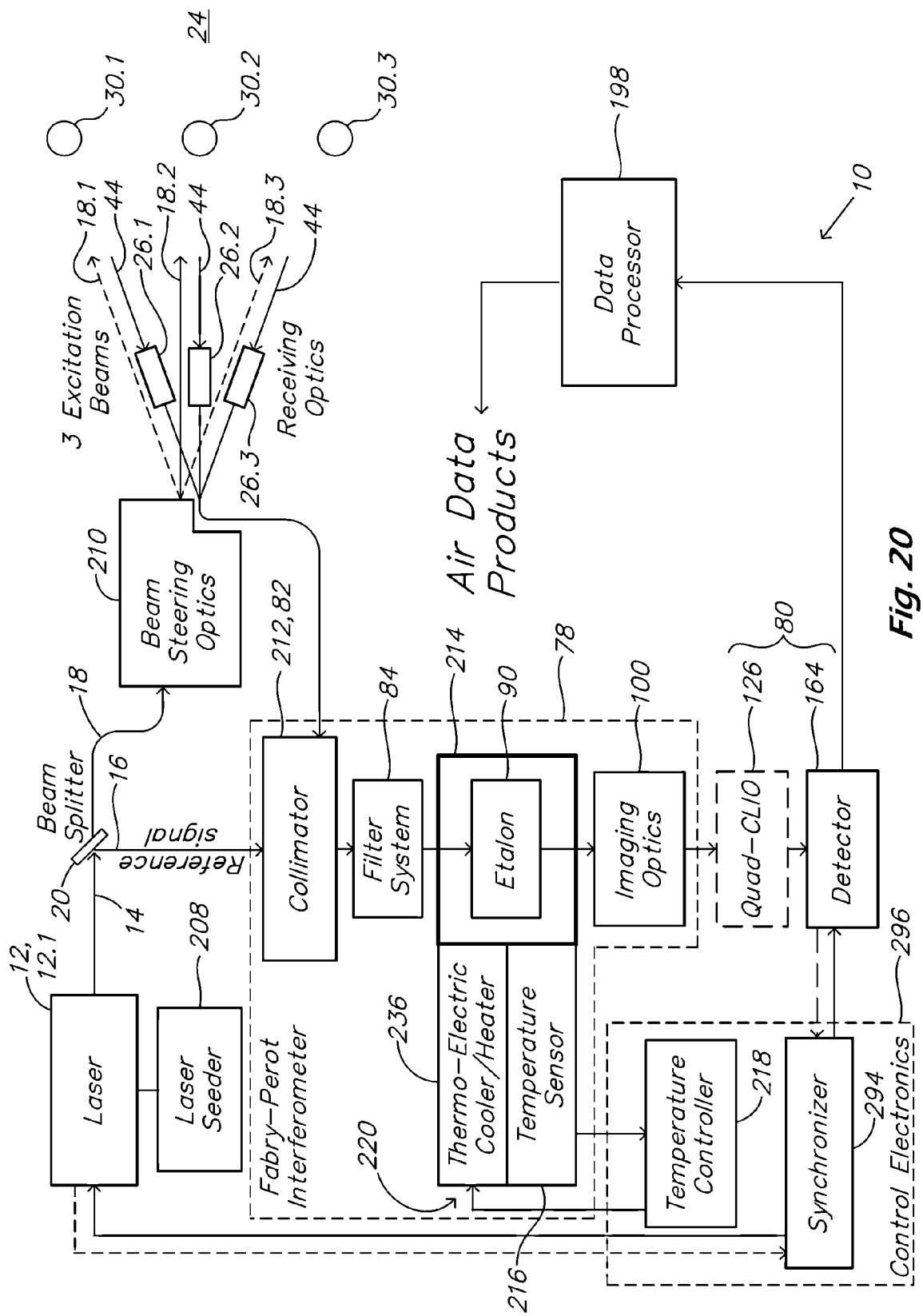
FIG. 20 illustrates a block diagram of various optical air data system embodiments.
Figure 21:
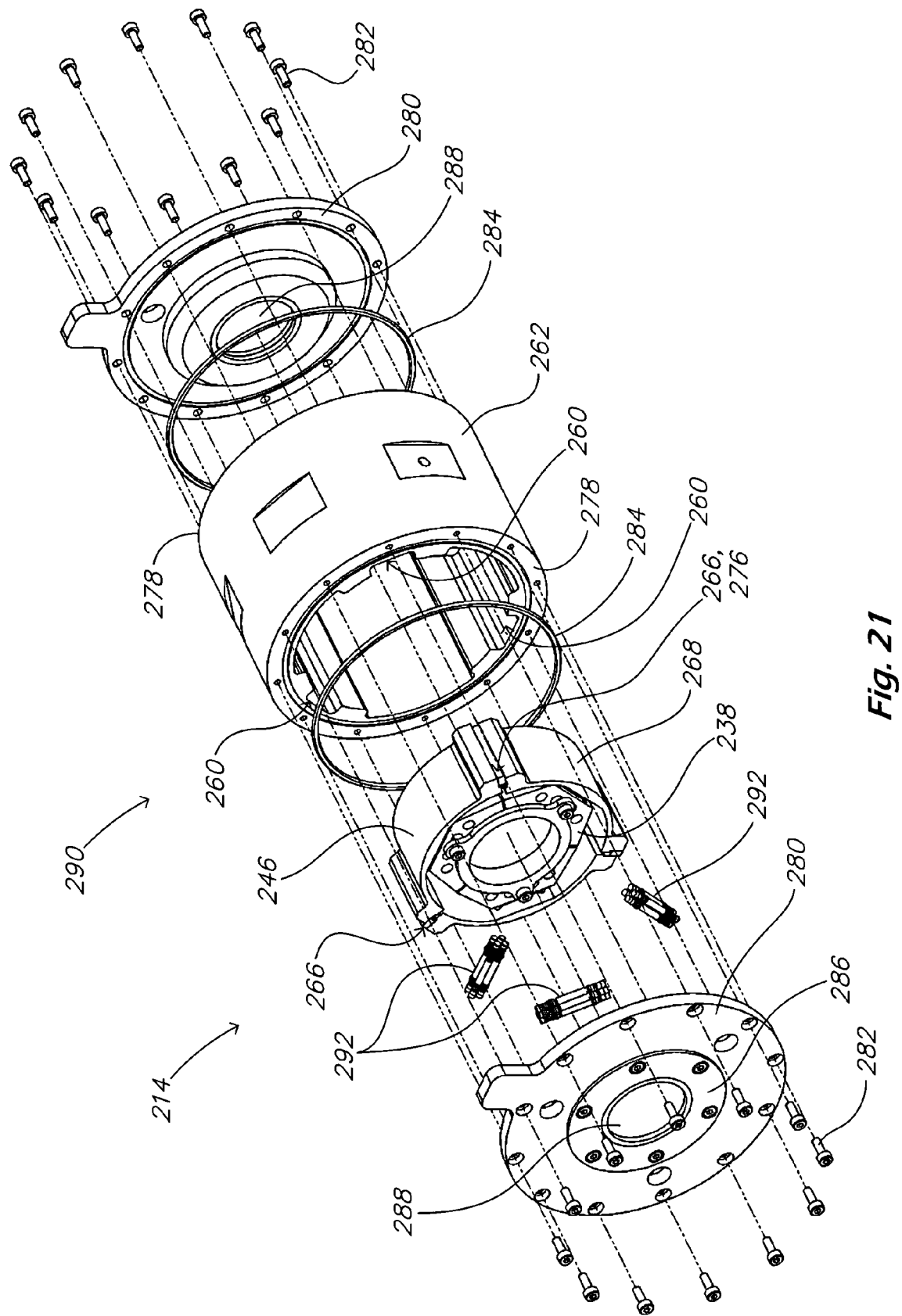
FIG. 21 illustrates an exploded view of a thermal chamber assembly enclosing a Fabry-Pérot etalon.
Figure 22:
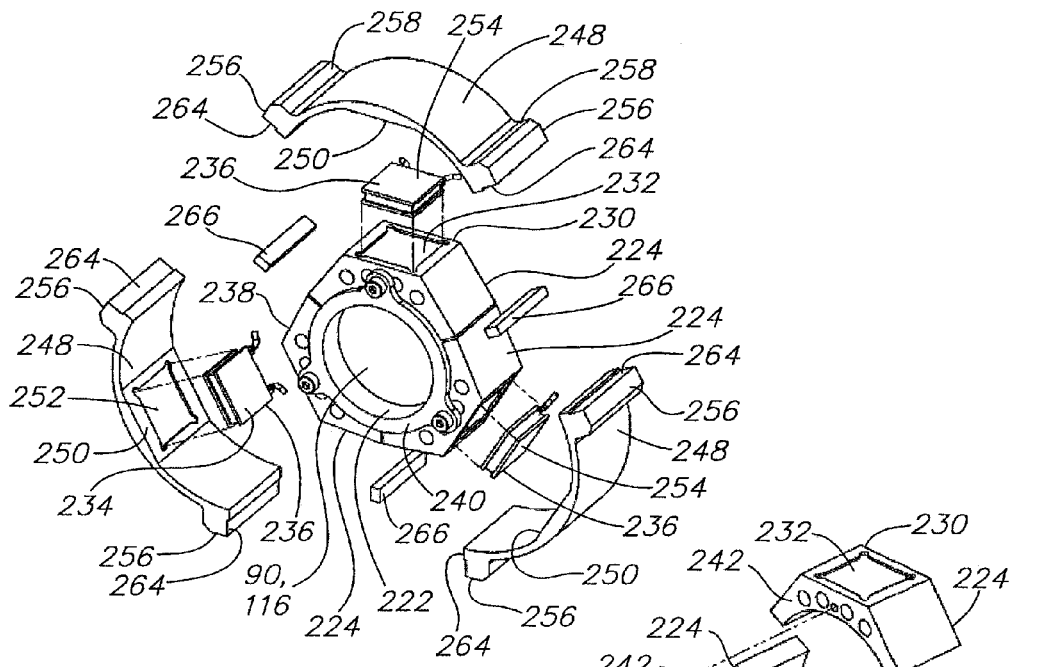
FIG. 22 illustrates a first exploded view of a core assembly incorporated in the thermal chamber assembly illustrated in FIG. 21.
Figure 23:
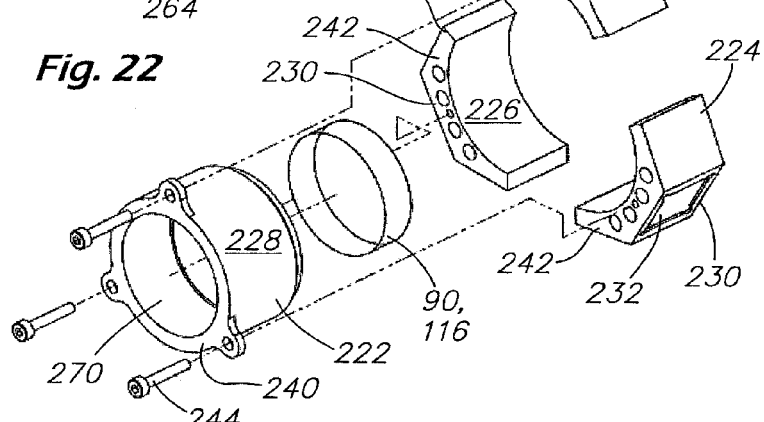
FIG. 23 illustrates a second exploded view of the core assembly incorporated in the thermal chamber assembly illustrated in FIG. 21.
Figure 24:
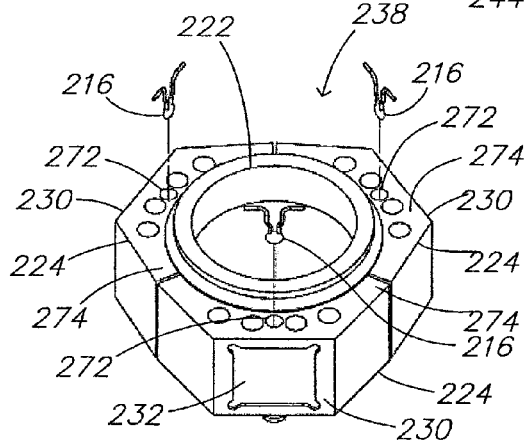
FIG. 24 illustrates a third exploded view of the core assembly incorporated in the thermal chamber assembly illustrated in FIG. 21.
Figure 25:
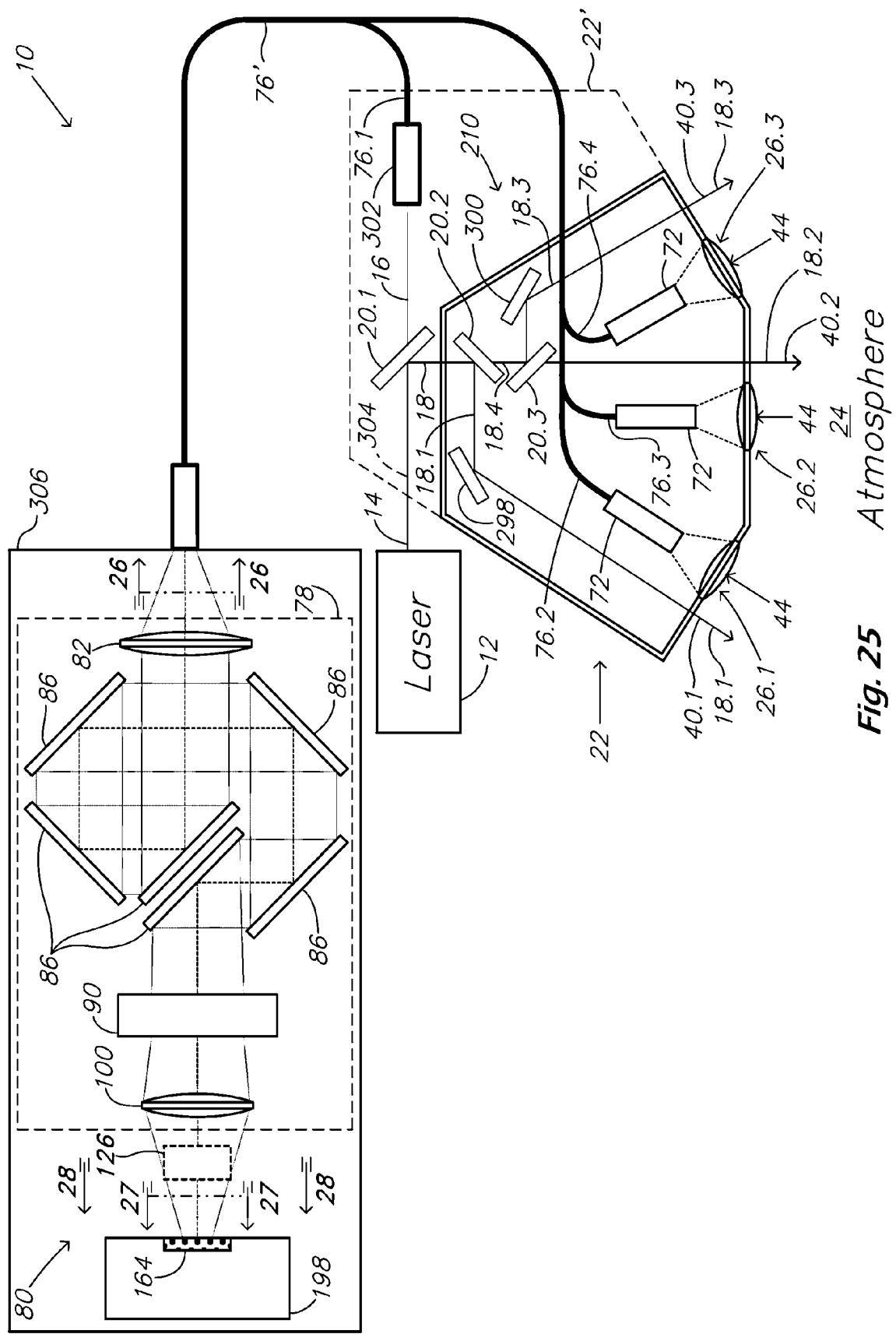
FIG. 25 illustrates a physical layout of various optical air data system embodiments.

Referring to FIG. 20, in accordance with other embodiments, the optical air data system 10 comprises a laser 12 that generates a first laser beam 14 which is divided into a reference beam 16 and a second laser beam 18 by a beam splitter optic 20. For example, in one embodiment, the laser 12 comprises a Nd:YAG laser 12.1, which operates in a pulsed mode, and which is operatively associated with a laser seeder 208, for example, a laser diode that provides for seeding the cavity of the pulsed Nd:YAG laser 12.1 with photons via an associated light coupling system, wherein the photons are injected from the laser seeder 208 into the cavity of the Nd:YAG laser 12.1 prior to the build-up of the laser pulse associated of the first laser beam 14, causing the frequency thereof to substantially match that of the laser seeder 208, so as to provide for substantially single-frequency operation. For example, in one embodiment, the laser seeder 208 is adapted in cooperation with the Nd:YAG laser 12.1 so that the bandwidth of the first laser beam 14 is as narrow or narrower than the bandwidth of the associated Fabry-Pérot interferometer 78. The bandwidth of the Fabry-Pérot interferometer 78 is related to the finesse thereof. Beam steering optics 210, for example, incorporating beam splitting mirrors, prisms, a combination thereof, or some other type of beam splitter, divide the second laser beam 18 into a plurality of second laser beams 18.1, 18.2 and 18.3, each directed in a different direction into the atmosphere 24. Corresponding associated respective telescopes 26.1, 26.2 and 26.3 each aimed so as to define an associated respective interaction region 30.1, 30.2, 30.3 of the respective second laser beams 18.1, 18.2 and 18.3 projected into the atmosphere 24, collect the associated backscattered light signals 44 from each of the respective interaction regions 30.1, 30.2, 30.3. The light signals 44 collected from each of the telescopes 26.1, 26.2 and 26.3, and the reference beam 16 each illuminate, and are simultaneously processed by, a separate portion of a Fabry-Pérot interferometer 78, wherein the light signals 44 and reference beam 16 passing through the Fabry-Pérot interferometer 78 are arranged with respect to one another in "cloverleaf" pattern. The light signals 44 and reference beam 16 are each first collimated by a collimator 212, e.g. a collimating lens 82, then filtered by a filter system 84 as described hereinabove, and then processed by an associated Fabry-Pérot etalon 90, the output of which is imaged by associated imaging optics 100 as associated circular fringe patterns 106.1, 106.2, 106.3 and 106.4 either directly onto a detector 164, or into a quad-CLIO 126 which transforms the circular fringe pattern 106.1, 106.2, 106.3 and 106.4 into a cross pattern 130 which is then imaged onto the detector 164. The associated optical components are adapted for the frequency and power levels of operation. For example, for an optical air data system 10 incorporating a Nd:YAG laser 12.1 operating at 355 nanometers, the optical elements would incorporate UV-grade fused silica substrates and standard anti-reflection coatings tuned for 355 nanometers.

The geometry of the circular fringe patterns 106.1, 106.2, 106.3 and 106.4 from the Fabry-Pérot etalon 90 is responsive to the operative gap 98, 98.1 thereof, which would vary with temperature if the associated material or materials controlling the length of the gap 98, 98.1 were to exhibit a non-zero coefficient of thermal expansion. Although the reference beam 16 simultaneously processed by the Fabry-Pérot etalon 90 provides for compensating for thermal drift affecting all portions of the Fabry-Pérot etalon 90 equally, it is beneficial if the temperature of the Fabry-Pérot etalon 90 can be controlled or maintained at a constant level so as to prevent a thermal expansion or contraction thereof during the operation thereof. Accordingly, in accordance with one aspect of the optical air data system 10, the Fabry-Pérot etalon 90 is thermally stabilized by enclosure in a thermally-controlled enclosure 214 so as to prevent thermally-induced drift of the circular fringe pattern 106.

In accordance with one aspect, the thermally-controlled enclosure 214 is passive, for example, with the Fabry-Pérot etalon 90 enclosed, i.e. thermally insulated or isolated, using a material or materials with a very low thermal conductance to increase the thermal time constant and to prevent any substantial thermal shock from reaching the Fabry-Pérot etalon 90. In accordance with another embodiment, or in combination therewith, the thermally-controlled enclosure 214 is constructed from a combination of materials adapted so that there is negligible net coefficient of thermal expansion in the portions of the structure surrounding the Fabry-Pérot etalon 90 that affect the length of the gap 98, 98.1.

Referring to FIGS. 21-24, in accordance with another aspect, a temperature of the thermally-controlled enclosure 214 is actively controlled responsive to at least one associated temperature sensor 216 using a temperature controller 218 incorporating a feedback control system 220 to control a heater, chiller or a combination heater and chiller—depending upon the temperature of the thermally-controlled enclosure 214 in relation to that of its environment. For example, referring to FIGS. 22 and 23, the Fabry-Pérot etalon 90 comprises a solid optical element 116—for example, constructed from high purity UV-grade fused silica—enclosed within a etalon mount 222 comprising a cylindrical sleeve constructed from a material with a coefficient of thermal expansion that closely matches that of the solid optical element 116 so as to provide for preventing or substantially eliminating unwanted thermally-induced radial stress in the solid optical element 116. The etalon mount 222 in turn is surrounded by a plurality, e.g. three, heat sink segments 224, each having a relatively high thermal conductance—for example, constructed of copper—each comprising an inner cylindrical face 226 that abuts an outside surface 228 of the etalon mount 222, and an outer face 230 incorporating a recess 232 adapted to receive and abut a first surface 234 of a thermo-electric heat pump 236, for example, what is known as a thermoelectric cooler (TEC). Upon assembly, the heat sink segments 224 collectively constitute an inner enclosure 238 that extends around and surrounds the etalon mount 222, the latter of which incorporates a flange 240 that abuts a set of first faces 242 on one side of the heat sink segments 224, and is fastened thereto with a plurality of fasteners 244, e.g. cap screws. The inner enclosure 238 is surrounded by an outer enclosure 246 comprising a plurality, e.g. three, heat-conducting outer ring segments 248, e.g.

constructed on aluminum, each of which incorporates an inside face 250 with an associated recess 252 that is adapted to receive and abut a second surface 254 of the thermoelectric heat pump 236. Each of the outer ring segments 248 incorporate associated flanges 256 at both ends, one side 258 of which are adapted to cooperate with internal grooves 260 in an outer shell 262 of the thermally-controlled enclosure 214, the other side 264 of which are adapted to cooperate with an outer ring retainer wedge 266 that operates between corresponding sides 264 of adjacent flanges 256 of adjacent outer ring segments 248 when the outer ring segments 248 are assembled to form the outer enclosure 246 surrounding the inner enclosure 238.

The inner 238 and outer 246 enclosures are assembled together to form a core assembly 268, as follows. The solid optical element 116 Fabry-Pérot etalon 90 is bonded inside a bore 270 of the etalon mount 222 with a thermal epoxy which provides for thermal conduction therebetween, wherein the inside diameter of the bore 270 is adapted so as to provide for a non-interfering fit with the solid optical element 116. The flange 240 of the etalon mount 222 is attached with fasteners 244 to the first faces 242 of the three heat sink segments 224 assembled around the outside surface 228 of the etalon mount 222. Three thermo-electric heat pumps 236 are sandwiched between respective recesses 232, 252 in a corresponding outer face 230 of each heat sink segment 224 and a corresponding inside face 250 of each outer ring segment 248, so that the first 234 and second 254 surfaces of the thermoelectric heat pumps 236 abut and are in thermal communication with the corresponding associated heat sink segment 224 and outer ring segment 248 respectively. The core assembly 268 further comprises a plurality, e.g. three, temperature sensors 216, e.g. thermistors, resistive temperature devices, or thermocouples—each of which is inserted in a corresponding hole 272 in a second face 274 of each heat sink segment 224, so as to provide for monitoring the temperature thereof, and so as to provide in cooperation with the associated temperature controller 218 and the associated thermo-electric heat pump 236, for controlling the temperature thereof.

The core assembly 268 is inserted in the outer shell 262 so that the flanges 240 of the outer ring segments 248 mate with the corresponding internal grooves 260 of the outer shell 262, and the outer ring retainer wedges 266 are inserted in the gaps 276 between the facing sides 264 of the flanges 240 so as to wedge the opposing sides 258 of the flanges 240 against associated internal grooves 260 of the outer shell 262, thereby providing for retaining the core assembly 268 within the outer shell 262, and providing for thermal communication therebetween. The ends 278 of the outer shell 262 are closed with associated end cap assemblies 280 secured thereto with associated fasteners 282 and sealed therewith associated seals 284, e.g. gaskets or o-rings. The end cap assemblies 280 incorporate associated window assemblies 286 fastened thereto and incorporating optical windows 288, e.g. constructed from UV-grade fused silica substrates with standard anti-reflection coatings, which provide for transmission of the associated light signals 88. The resulting assembly constitutes a thermally-stabilized etalon assembly 290 incorporating a thermally-controlled enclosure 214. The thermally-stabilized etalon assembly 290 further comprises a plurality of electrical connectors 292 therein which provide for connecting the thermo-electric heat pumps 236 and the temperature sensors 216 with the associated temperature controller 218. The temperature controller 218 uses the temperature sensors 216 to monitor the temperature of the core assembly 268, and controls the heating or cooling thereof relative to the environment using the associated thermo-electric heat pumps 236 so as to maintain the temperature of the core assembly 268 at a specified set-point. The outer enclosure 246 in thermal communication with the outer shell 262 provides for either supplying heat to or rejecting heat from the inner enclosure 238 responsive to the thermal effort of the thermo-electric heat pumps 236 as needed to maintain a particular set-point temperature. For example, in one embodiment, the set-point temperature is adapted so as to minimize the energy needed to maintain that temperature, while also maintaining a sufficient offset so as to operate the thermo-electric heat pumps 236 most efficiently. For example, for a thermo-electric heat pump 236 that operates most efficiently when heating, the set-point temperature might be 5 to 10 degrees Celsius above the nominal environmental temperature, e.g. 5 to 10 degrees Celsius above room temperature.

In one embodiment, the firing of the Nd:YAG laser 12.1 is, for example, controlled with an associated Q-switch, which may be synchronized with the acquisition of associated images 200 from the detector 164 using a synchronizer 294, thereby precluding the need for an electronic shutter that would otherwise provide for gating light signals 88 to the detector, although, alternatively, an electronic shutter could also be used or could be used without a synchronizer 294, for example, so as to preclude subsequent imaging during the process of reading image data from a CCD detector 164.1. The synchronizer 294, if used, could be incorporated in a control electronics assembly 296, e.g. which could also incorporate the associated temperature controller 218 and/or the associated data processor 198. The synchronizer 294 could be adapted to either generate a master timing signal for controlling both the laser 12 and the detector 164, or could be adapted to relay a timing pulse generated by either one of the laser 12 and detector 164 to the other of the detector 164 and laser 12.

Referring to FIGS. 25-28, in accordance with several other embodiments, the optical air data system 10 comprises a laser 12 that generates a first laser beam 14 which is divided into a reference beam 16 and a second laser beam 18 by a first beam splitter 20.1. The second laser beam 18 is directed into an optical head 22 incorporating associated beam steering optics 210 which divide the second laser beam 18 into a plurality of second laser beams 18.1, 18.2 and 18.3, each directed in a different direction, e.g. line of sight 40.1, 40.2, 40.3, into the atmosphere 24. For example, the beam steering optics 210 comprise second 20.2 and third 20.3 beam splitters, wherein the second beam splitter 20.2 reflects the first portion 18.1, e.g. about one third, of the second laser beam 18, and transmits a fourth portion 18.4, e.g. about two thirds, thereof, and the third beam splitter 20.3 transmits the second portion 18.2, e.g. about one half, of the fourth portion 18.4 of the second laser beam 18, and reflects the remaining third portion 18.3 of the second laser beam 18. The first portion 18.1 of the second laser beam 18 reflected from the second beam splitter 20.2 is directed along a first line of sight 40.1 by a first mirror 298, e.g. a front-surface mirror, the second portion 18.2 of the second laser beam 18 is transmitted through the third beam splitter 20.3 along a second line of sight 40.2, and the third portion 18.3 of the second laser beam 18 reflected from the third beam splitter 20.3 is directed along a third line of sight 40.3 by a second mirror 300, e.g. a front-surface mirror. For example, the associated front-surface first 298 and second 300 mirrors may each incorporate dielectric or metallic coatings (e.g. silver), or may comprise a long-wave-pass dichroic beam splitter. The optical head 22 further incorporates a plurality of respective telescopes 26.1, 26.2 and 26.3 each associated with a different of the respective second laser beams 18.1, 18.2 and 18.3 directed along or in cooperation with respective lines of sight 40.1, 40.2 and 40.3, each aimed at an associated respective interaction region 30.1, 30.2, 30.3 of the respective second laser beams 18.1, 18.2 and 18.3 projected into the atmosphere 24, and each adapted to collect the associated backscattered light signals 44 from each of the respective interaction regions 30.1, 30.2, 30.3.

Each telescope 26 comprises a lens system 74, and the light signal 44 collected thereby is collected by the final light-collecting element 72 thereof into a corresponding fiber optic 76.2, 76.3, 76.4 that directs the returned photons to associated portions of a Fabry-Pérot interferometer 78 and an associated detection system 80 for processing thereby. The reference beam 16 from the laser 12 and beam splitter optic 20 is separately collected by a separate light-collecting element 302 into a fiber optic 76.1 directed to a separate portion of the Fabry-Pérot interferometer 78 and an associated detection system 80 for simultaneous processing thereby. For example, the final light-collecting elements 72 of the telescopes 26.1, 26.2 and 26.3, and the light-collecting element 302 for collecting the reference beam 16, may comprise either a GRIN lens or an aspheric lens. In one embodiment, the associated fibers of the four fiber optics 76.1, 76.2, 76.3 and 76.4 are bundled together in a fiber-optic bundle 76' which operatively couples the laser 12 and optical head 22 to the Fabry-Pérot interferometer 78. The use of fiber optics 76.1, 76.2, 76.3 and 76.4 and/or a fiber-optic bundle 76' provides for simplifying the alignment of the Fabry-Pérot interferometer 78 with the telescopes 26.1, 26.2 and 26.3 and with the reference beam 16 from the laser 12. Furthermore a separate fiber optic 304 may be used to operatively couple the laser 12 to the optical head 22, either directly from the output of the laser 12 to the optical head 22—the latter of which could be adapted in an alternate embodiment of an optical head 22' to incorporate the first beam splitter 20.1,—or from the first beam splitter 20.1 to the optical head 22, or both, so as to provide for flexibility in packaging the optical head 22 in relation to the laser 12, which can be particularly beneficial for aircraft installations for which the optical head 22 is installed proximate to the surface 36 of the aircraft 38, so as to provide for mounting the laser 12 in a more benign and stable environment within the aircraft 38. A fiber optic 304 interconnecting the laser 12 with the optical head 22 also provides for precise alignment of the associated first laser beam 14 with the optical head 22, and simplifies associated installation and maintenance of the associated components thereof.

The associated fiber optics 76.1, 76.2, 76.3, 76.4 and 304 can be adapted as necessary to incorporate non-solarizing fibers so as to mitigate against degradation from relatively high-energy UV laser light which might otherwise solarize the associated fibers and thereby degrade associated fiber-optic transmission. Furthermore, the fiber optic 304 from the laser 12 to the optical head 22 may comprise a bundle of associated fibers, each adapted to transmit a portion of the total light to be transmitted to the optical head 22, so as to reduce the energy density within each fiber of the bundle and thereby mitigate against the degradation thereof. For example, a beam expander may be used to enlarge the first laser beam 14 so as to distribute the associated energy thereof amongst the plurality of associated fibers.

Figure 26:
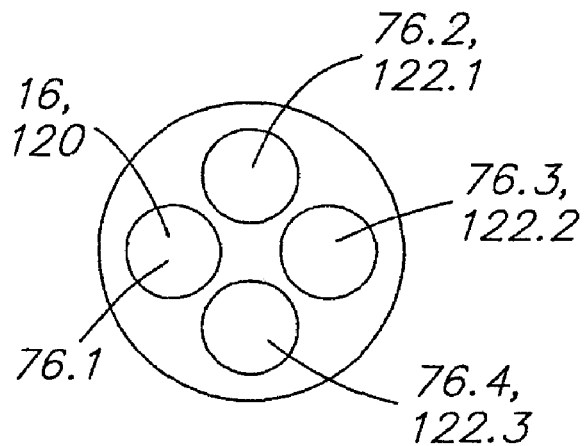
FIG. 26 illustrates an end view of a fiber-optic assembly connected to the input of the Fabry-Pérot interferometer illustrated in FIG. 25.
Figure 27:
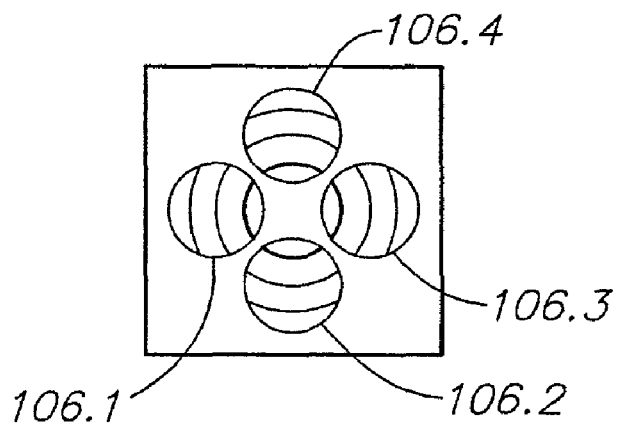
FIG. 27 illustrates a view of a set of circular fringe patterns imaged onto the detector of the optical air data system illustrated in FIG. 25 for an embodiment that does not incorporate a quad-CLIO.
Figure 28:
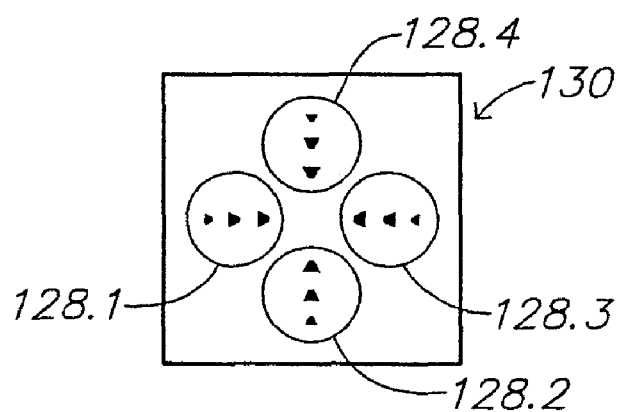
FIG. 28 illustrates a view of a set of substantially linear fringe patterns imaged onto the detector of the optical air data system illustrated in FIG. 25 for an embodiment that incorporates a quad-CLIO.

The light signals 44 collected by each of the telescopes 26.1, 26.2 and 26.3, and the reference beam 16, are transmitted to the Fabry-Pérot interferometer 78 by the associated fiber optics 76.1, 76.2, 76.3 and 76.4 and are each simultaneously processed by a separate portion of a Fabry-Pérot interferometer 78, wherein the light signals 44 and reference beam 16 passing through the Fabry-Pérot interferometer 78 are arranged with respect to one another in "cloverleaf" pattern, as illustrated in FIG. 26. The light signals 44 and reference beam 16 are each collimated by a collimating lens 82, then filtered by a filter system 84 as described hereinabove, and then processed by the associated Fabry-Pérot etalon 90, the output of which is imaged by associated imaging optics 100 as associated circular fringe patterns 106.1, 106.2, 106.3 and 106.4 either directly onto a detector 164 as illustrated in FIG. 27, or into a quad-CLIO 126 which, as illustrated in FIG. 28, transforms the circular fringe pattern 106.1, 106.2, 106.3 and 106.4 into a cross pattern 130 which is then imaged onto the detector 164. The image 200 from the detector 164 is then processed by a data processor 198 which provides for determining the associated air data products therefrom. The Fabry-Pérot interferometer 78 and the associated detection system 80 may be mounted within a common housing 306.

The optical air data system 10 provides for directly detecting laser energy scattered off of either molecules of the atmosphere, aerosols in the atmosphere, or a combination of the two, provides for directly measuring the associated velocity and direction, density, and temperature of the atmosphere, and provides for deriving an associated complete set of air data products. For example, relatively short wavelength laser energy is scattered by molecules of the atmosphere in accordance with Rayleigh scattering. Laser energy can also be scattered by aerosols in the atmosphere in accordance with Mie scattering. Rayleigh scattering generally refers to the scattering of light by either molecules or particles having a size less than about $\frac{1}{10}^{th}$ the wavelength of the light, whereas Mie scattering generally refers to scattering of light by particles greater than $\frac{1}{10}^{th}$ the wavelength of the light. Being responsive to Rayleigh scattering, the optical air data system 10 is therefore responsive to the properties—e.g. velocity, density and temperature—of those molecules in the atmosphere giving rise to the associated scattering of the light detected by the optical air data system 10. Accordingly, the optical air data system 10 provides for operation in clean air, i.e. in an atmosphere with no more than a negligible amount of aerosols, depending substantially only upon molecular backscatter.

The signals from the associated signal channels 122.1, 122.2 or 122.3 received from any one of the three interaction regions 30.1, 30.2, 30.3 are processed by the Fabry-Pérot interferometer 78 and acquired by the associated one or more detectors 164. The reference channel 120 is simultaneously processed by the same Fabry-Pérot interferometer 78, and used to provide for calibrating measurements from each of the interaction regions 30.1, 30.2, 30.3 associated with each of the fields of view 32 of each of the telescopes 26. The optical air data system 10 uses the Fabry-Pérot interferometer 78 to directly detect information from the scattered laser energy, wherein the reference 120 and signal 122.1, 122.2, 122.3 channels are each detected separately, and information from the reference channel 120 can then be used to calibrate the associated signal channels 122.1, 122.2, 122.3. The detection process is responsive to an incoherent Doppler shift of the laser light backscattered by molecules and aerosols in the atmosphere 24 responsive to Rayleigh and Mie scattering respectively.

The optical air data system 10 can take advantage of aerosols when present, but does not rely upon their presence. The signals from the reference channel 120 and the signal channels 122.1, 122.2 and 122.3 of the optical air data system 10 can be used to directly measure velocity, true airspeed, vertical speed, angle of attack, angle of sideslip, static density, static temperature, and aerosol to total scattering ratio (ASR). From these data products the following quantities can be directly calculated: calibrated airspeed, Mach number, static pressure, total pressure, dynamic pressure, pressure altitude, air density ratio, total temperature, angle of attack, pressure differential, and angle-of-sideslip pressure differential.

Figure 29:
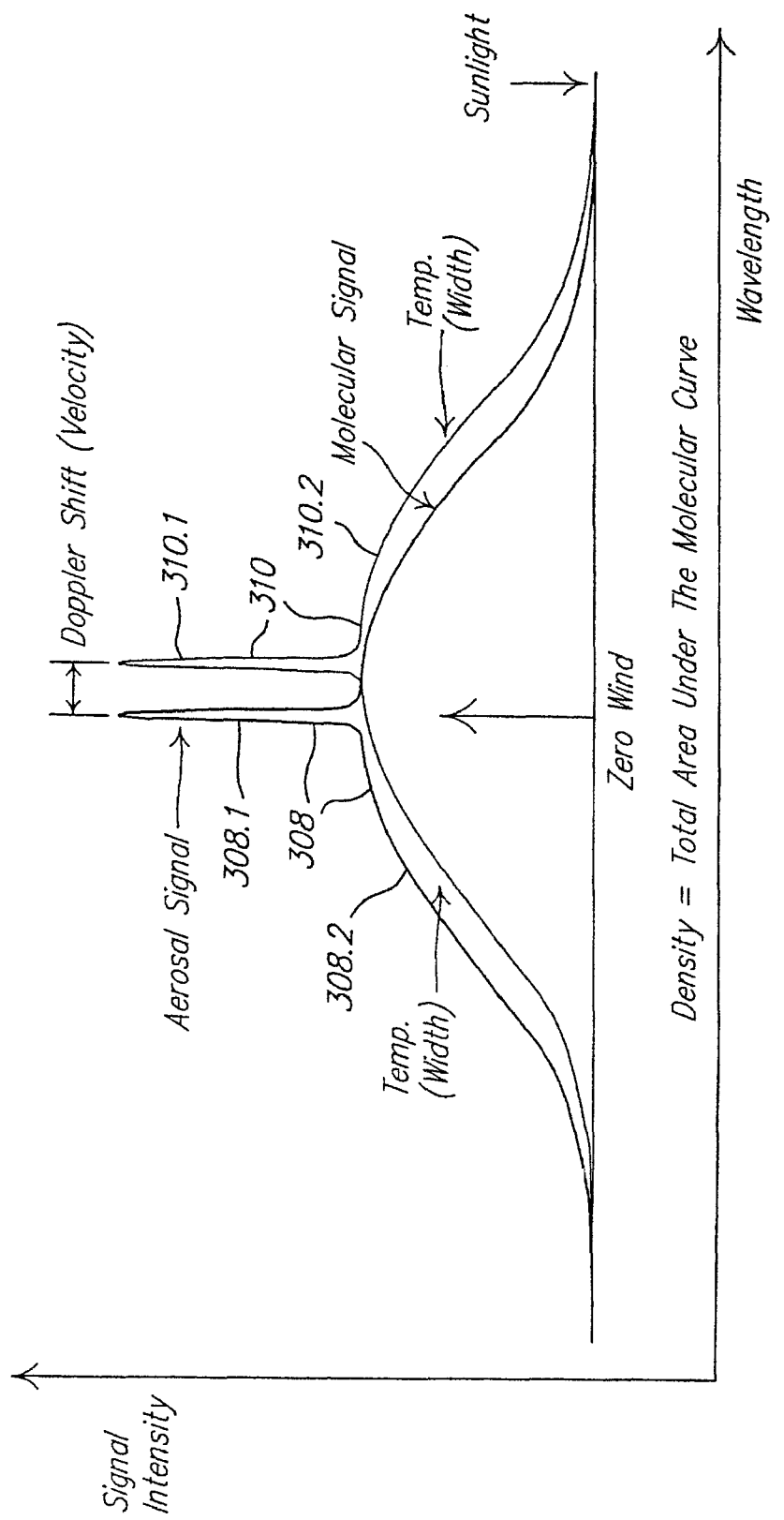
FIG. 29 illustrates fringes from the Fabry-Pérot etalon from two scattered signals associated with different velocities.

Wind velocity, density, and temperature are directly calculated using the fringe data from the Fabry-Pérot interferometer 78. The other air data products are derived from these three basic measurements, in view of the knowledge of the associated geometry of the optical head 22. Referring to FIG. 29, a first fringe 308 corresponds to a zero-wind, i.e. zero-velocity condition, and a second fringe 310 corresponds to a non-zero wind condition, wherein both the first 308 and second 310 fringes are illustrated as exhibiting both an aerosol signal component 308.1, 310.1 and a molecular signal component 308.2, 310.2 respectively. The reference channel 120 also provides for a zero wind condition, but does not contain either molecular or background components, and accordingly would exhibit only the aerosol signal component 308.1 illustrated in FIG. 29.

Figure 30:
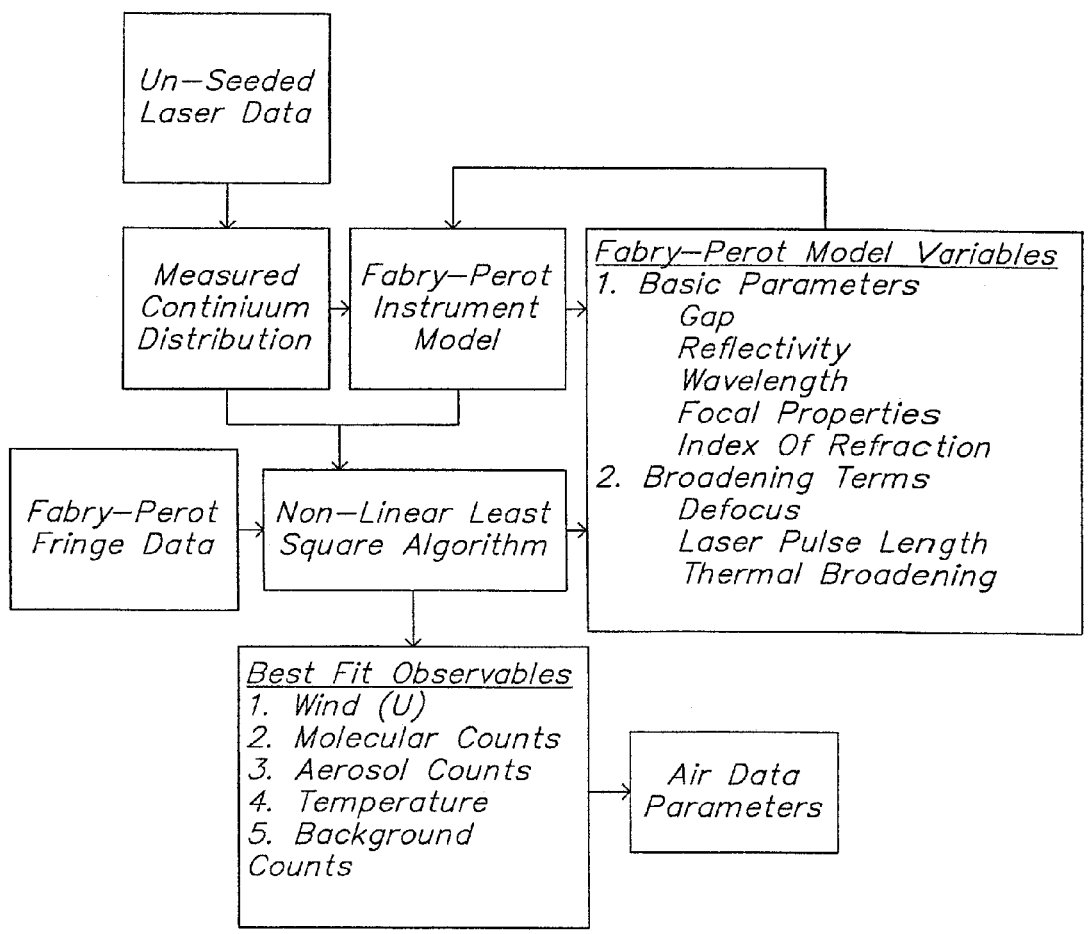
FIG. 30 illustrates a block diagram of an optical air data system data analysis process.

Referring to FIG. 30, the image 200 of the fringe pattern 92 generated by the optical air data system 10 is modeled use non-linear least square techniques. The distribution of the stray light and background radiation is provided by measurements of the fringe pattern 92 with the laser seeder 208 turned off so as to enable the Nd:YAG laser 12.1 to lase over a relatively wider range of wavelengths that provides for simulating background radiation. The fringe patterns 92 are otherwise measured with the laser seeder 208 turned on so as to provide for substantially single-frequency operation. The instrument functions and derivatives used in the algorithm are formed from analytic representations of the Fabry-Pérot interferometer 78 and include the necessary broadening functions to account for defects of the Fabry-Pérot etalon 90, e.g. the associated solid optical element 116, as well as temperature-dependent line shape broadening from molecular backscatter. Empirical data for the illumination pattern is also used so that the correct light distribution of the fringes is accurately represented in the models. In an optical air data system 10 with three signal channels 122.1, 122.2 and 122.3 for three corresponding fields of view 32, and a reference channel 120, a line-of-sight relative wind velocity U is determined for each signal channel 122.1, 122.2 and 122.3, which is calibrated using a corresponding measurement of the reference channel 120. As used herein, the term relative wind is intended to refer to the relative motion between the atmosphere—included molecules and aerosols—and the optical air data system 10. In addition to frequency—which, responsive to associated Doppler shift, provides for measuring associated velocity—the algorithm determines the contribution to the fringe pattern from molecular and aerosol backscatter, the background radiation, and the temperature of the atmosphere 24 for each particular associated line of sight 40.1, 40.2 and 40.3 along a direction of the corresponding associated field of view 32 of the associated telescope 26.1, 26.2 and 26.3. The molecular signal yields a measure of air density that can be related to pressure. The aerosol to total scattering ratio is also directly derived from the results.

Figure 31:
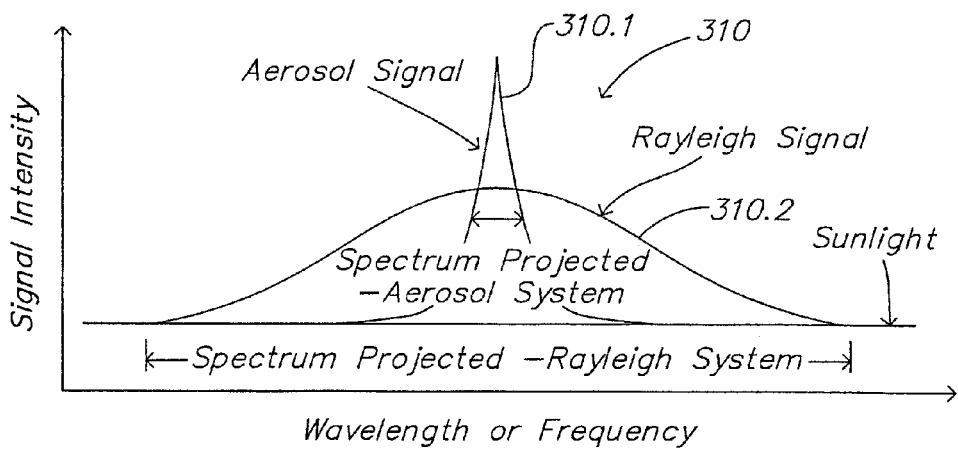
FIG. 31 illustrates a fringe associated with a signal channel processed by the Fabry-Pérot etalon, wherein the fringe comprises an aerosol (Mie), molecular (Rayleigh) and background signal components.

The spectral shape of the light signal 44 of a signal channel 122.1, 122.2 or 122.3 processed by the Fabry-Pérot etalon 90, for a single associated fringe to be modeled, has a qualitative form illustrated in FIG. 31, wherein the molecular scattered light, i.e. the molecular component 310.2, exhibits a broadened spectral shape, while the aerosol scattered light, i.e. the aerosol component 310.1, produces a sharp peak which is nearly identical to the shape of the transmitted laser light. Underlying these two components is a background signal from scattered sunlight, which at the scale of FIG. 31 forms a relatively flat continuum. By way of comparison, the corresponding spectral shape of the light of the reference channel 120 processed by the Fabry-Pérot etalon 90 is substantially the same as that of the aerosol component 310.1.

Figure 32:
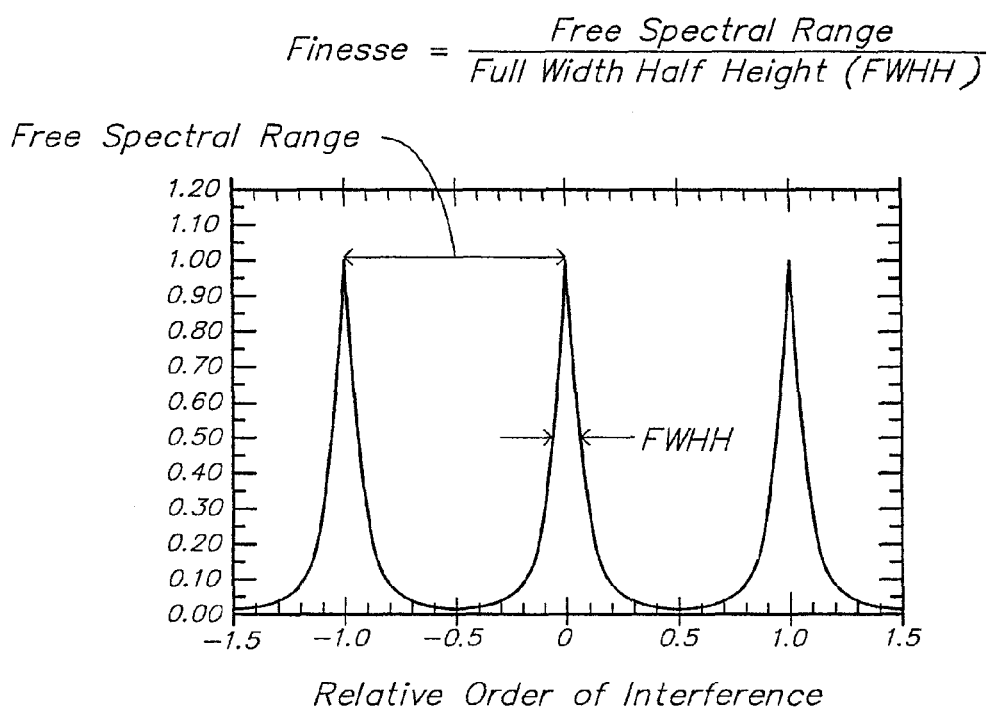
FIG. 32 illustrates a periodic transmission function of a Fabry-Pérot etalon.

The transmission, T, of a perfect Fabry-Pérot etalon 90 is given by the Airy function as follows, and as described in Hernandez, G., *Fabry-Perot interferometers*, Cambridge: Cambridge University Press, 1986, and Vaughan, J. M., *The Fabry-Perot Interferometer: History, Theory, Practice and Applications*, Bristol, England: A. Hilger, 1989, both of which documents are incorporated herein by reference:

$$T(M) = \frac{\left(1 - \frac{L}{1-R}\right)^2 (1-R)^2}{1 - 2R\cos 2\pi M + R^2} \tag{6}$$

where L is the loss per plate (absorption and scattering), R is the plate reflectivity, and M is the order of interference. Equation (6) describes a periodic transmission function, which is illustrated in FIG. 32. The separation between peaks is known as the free spectral range and depends inversely on the gap 98, 98.1 between the first 94 and second 96 partially-reflective surfaces, so that a relatively large spacing results in a relatively small free spectral range. The resolution of a Fabry-Pérot interferometer 78 is determined by the full width at half height (FWHH) of a fringe, which in turn determines the Rayleigh resolving power of the Fabry-Pérot interferometer 78. The finesse of the Fabry-Pérot interferometer 78 is a unitless quantity that is defined as the ratio of the Free Spectral Range(FSR) to the FWHH. Finesse defines the number of resolvable elements that can fit in between two resonance peaks, and represents the sensitivity of the Fabry-Pérot interferometer 78. In the absence of any defects, the finesse is related primarily to the reflectivity. For example, a reflectivity of 0.80 gives a finesse of 14, and a reflectivity of 0.90 gives a finesse of 30. In the presence of defects, both the finesse and the peak transmittance are reduced. Unless careful attention is given to defects when a Fabry-Pérot system is designed, the finesse and throughput can be substantially less than anticipated and can adversely bias the measured results. In order to incorporate defects into the instrument model Equation (6) can be written in the equivalent series form, as follows:

$$T(M) = \left(1 - \frac{L}{1-R}\right)^2 \left(\frac{1-R}{1+R}\right)\left(1 + 2\sum_{n=1}^{\infty} R^n \cos 2\pi n M\right) \tag{7}$$

Equation (7) is a useful form of the Airy function since it provides for relatively easy convolutions with broadening functions.

The order of interference M is given by:

$$M = 2\mu t \nu \cos\theta \tag{8}$$

where $\mu$ is the index of refraction of the material between the first 94 and second 96 partially-reflective surfaces, t is the effective gap 98, 98.1, $\nu$ is the wavenumber of light, and $\theta$ is the angle of incidence in the Fabry-Pérot etalon 90 which is responsive to the focal length of the imaging optics 100 and the size of the detector 164. Perturbations of t, $\nu$ and $\theta$ from a set of standard conditions and normal incidence, can be modeled as follows:

$$t = t_0 + \Delta t \quad (9)$$

$$v = v_0 + \Delta v \quad (10)$$

$$\cos\theta = 1 - \frac{\theta^2}{2} \quad (11)$$

The order of interference can then be written as follows:

$$M = 2\mu t_0 v_0 + 2\mu t_0 \Delta v + 2\mu v_0 \Delta t - 2\mu t_0 v_0 \frac{\theta^2}{2} \quad (12)$$

where only the first order terms have been retained, and can be further expressed as follows:

$$M = M_o + \Delta M \quad (13)$$
where $$M_0 = 2\mu t_0 v_0 \quad (14)$$
and $$\Delta M = 2\mu t_0 \Delta v + 2\mu v_0 \Delta t - 2\mu t_0 v_0 \frac{\theta^2}{2} \quad (15)$$

The quantity $\frac{1}{2}\mu t_0$ is the change in wavenumber required to change the order of interference by one, and is defined as the free spectral range, $\Delta v_{FSR}$, which results in:

$$\Delta M = \frac{\Delta v}{\Delta v_{FSR}} - \frac{v_0}{\Delta v_{FSR}} \frac{\theta^2}{2} + 2\mu v_0 \Delta t \quad (16)$$

Without loss of generality $M_0$ can be an integer and therefore $T(M)=T(\Delta M)$.

Real instruments have defects which influence the behavior thereof and can be accounted for by broadening functions in the models used to characterize the device. These broadening functions are well known and are represented by a set of probability functions which can be convolved with the basic Fabry-Pérot Airy function to give the general result:

$$T(\Delta v, \theta) = \quad (17)$$
$$\left(1 - \frac{L}{1-R}\right)^2 \left(\frac{1-R}{1+R}\right)\left[1 + 2\sum_{n=1}^{\infty} R^n D_n \cos 2\pi n\left(\frac{\Delta v}{\Delta v_{FSR}} - \frac{v_0}{\Delta v_{FSR}}\frac{\theta^2}{2}\right)\right]$$

wherein the broadening function $D_n$ filters the transmission T depending upon the magnitude of the defect or broadening process, and is calculated from the following product:

$$D_n = \prod_{q=1}^{N_q} d_n^q \quad (18)$$

wherein $d_n^q$ is the $n^{th}$ element of the convolution of the $q^{th}$ broadening function $G_q$—described hereinbelow—with the instrument model of Equation (7). The convolution integral is defined as follows:

$$d_n^q = \int_{-\infty}^{\infty} G_q(\delta') * T(M(n) - \delta') d\delta' \quad (19)$$

where $T(M(n)-\delta')$ is the Fabry-Pérot infinite series term.

A simplified notation can be used to provide for a more compact representation, wherein $$A_n = \left(1 - \frac{L}{1-R}\right)^2 \left(\frac{1-R}{1+R}\right) \text{ for } n = 0 \quad (20)$$
$$= 2\left(1 - \frac{L}{1-R}\right)^2 \left(\frac{1-R}{1+R}\right) R^n D_n \text{ for } n > 0$$

so that the Airy function can be written as follows:

$$T(\Delta v, \theta) = \sum_{n=0}^{\infty} A_n \cos 2\pi n\left(\frac{\Delta v}{\Delta v_{FSR}} - \frac{v_0}{\Delta v_{FSR}}\frac{\theta^2}{2}\right) \quad (21)$$

The broadening functions $G_q$ account for broadening resulting from each of Doppler shift, laser width, scattering broadening, and turbulent motion, respectively, as given hereinbelow, for $N_q=3$ in Equation (18).

Doppler Broadening: The Doppler shift due to the mean air motion is given by:

$$\Delta v = v_1 \frac{2U_h \sin\phi}{c} \quad (22)$$

where $\Delta v$ is the Doppler shift, $v_1$ is the laser wavenumber, $U_h$ is the horizontal wind speed in the direction of viewing, and $\phi$ is the angle from the zenith made by the second laser beams 18.1, 18.2 or 18.3 as it passes through the atmosphere 24, wherein $U_h \sin\phi$ is the line-of-sight relative wind velocity U. Accordingly, Equation (22) provides the relationship between line-of-sight relative wind velocity U and the Doppler shift $\Delta v$.

Laser Spectral Width Broadening: The spectral shape of the laser is assumed to be of Gaussian form, as follows:

$$G_{laser}(\Delta v, \Delta v_1) = \frac{1}{\sqrt{\pi}\, \Delta v_1} e^{-\frac{\Delta v^2}{\Delta v_1^2}} \quad (23)$$

where $\Delta v_1$ is the 1/e width of the laser, wherein the shorter the duration a laser pulse, the broader the associated broadening function, which results in lowered finesse for the Fabry-Pérot etalon 90.

Scattering Broadening: The affect on the transmission T of a Fabry-Pérot interferometer 78 due to broadening induced by molecular scattering is different from that induced by aerosol scattering. Accordingly, different broadening functions $G_q$ are used to account for molecular and aerosol scattering, respectively, in respective corresponding models for the molecular $T_{Mol}$ and aerosol $T_{Aero}$ components of transmission T of the Fabry-Pérot interferometer 78.

The molecular scattering media broadens the signal due to associated random motions. The molecules have a Gaussian broadening function, as follows:

$$G_{molecules}(\Delta v, \Delta v_G) = \frac{1}{\sqrt{\pi}\,\Delta v_G} e^{-\frac{\Delta v^2}{\Delta v_G^2}} \qquad (24)$$

where $\Delta v_G$ is the 1/e width and is given by:

$$\Delta v_G = \frac{v_l}{c}\left(\frac{2k \cdot Temp}{m}\right)^{\frac{1}{2}} \qquad (25)$$

or $$\Delta v_G = 4.30 \times 10^{-7} v_l \left(\frac{Temp}{\overline{M}}\right)^{\frac{1}{2}} \qquad (26)$$

where k is Boltzmann's constant, m is the mean mass of a molecule in the atmosphere, Temp is the static absolute temperature in degrees Kelvin, and $\overline{M}$ is the mean molecular weight ($\overline{M}$=28.964).

The aerosol broadening function has a Lorentzian form as follows, for example, as described in Fiocco, G., and DeWolf, J. B., "Frequency spectrum of laser echoes from atmospheric constituents and determination of aerosol content of air," *Journal of Atmospheric Sciences*, v.25, n3, May 1968, pp. 488-496; and Benedetti-Michelangeli, G., Congeduti, F., and Fiocco, G., "Measurement of aerosol motion and wind velocity in the lower troposphere by Doppler optical radar," *Journal of the Atmospheric Sciences*, v.29, n5, July 1972, pp. 906-910, both of which references are incorporated herein by reference:

$$L_{aerosol}(\Delta v, \alpha_A) = \frac{1}{\pi}\frac{\alpha_A}{\alpha_A^2 + \Delta v^2} \qquad (27)$$

where the half width $\alpha_A$ is given by:

$$\alpha_A = \frac{2\pi v^2 D}{c} \qquad (28)$$

The spectral width of the aerosol-induced broadening component is extremely narrow compared to the molecular-induced broadening component, and in most cases are much narrower than the laser pulse, so that aerosol scattering essentially acts as a delta function and is not dependent on temperature.

Turbulent Motion Broadening: In addition to random motions of molecules and aerosols, the model allows for random motions of bulk parcels, i.e. turbulence, wherein this broadening is represented by a relatively simple Gaussian shape, as follows:

$$G_{turbulence} = (\Delta v, \Delta v_T) = \frac{1}{\sqrt{\pi}\,\Delta v_T} e^{-\frac{\Delta v^2}{\Delta v_T^2}}, \qquad (29)$$

where $$\Delta v_T = \frac{v_l}{c} U_T, \qquad (30)$$

and $U_T$ is a characteristic turbulent velocity, which is a predefined constant that is independent of the line-of-sight relative wind velocity U. In some embodiments, this term is ignored because it is indistinguishable from temperature, so that the affects of Equations (24) and (29) are indistinguishable from one another.

Other broadening functions $G_q$ can also be utilized in addition to those described hereinabove, for example, so as to account for a defocus of the imaging optics 100.

The values of the line of binned pixels 188.1, 188.2, 188.3 and 188.4 for the reference 120 and signal 122.1, 122.2, 122.3 channels, respectively, provide a corresponding transmission measure T' of the Fabry-Pérot interferometer 78 for the corresponding reference 120 and signal 122.1, 122.2, 122.3 channels, respectively. Each transmission measure T' is an N-element vector, wherein each element n of the vector corresponds to a different wavelength or corresponding order of interference. The element values are in units of measurement counts; for example, with one measurement count being equal to one photo-electron captured by the detector 164. The transmission measure T' is a measure of data from the Fabry-Pérot interferometer 78 that can be modeled as described hereinabove in accordance with Equations (6) through (30), as represented by FIGS. 31 and 32, wherein FIG. 31 illustrates a finer scale of detail of each fringe illustrated in FIG. 32. Accordingly, the transmission measure T', in units of total counts of binned values from the detector 164, can be modeled as the sum of associated molecular, aerosol and background counts, as follows:

$$T = T_{Mol}(Temp,U) \cdot MolCounts + T_{Aero}(U) \cdot AeroCounts + T_{Back} \cdot BackCounts \qquad (31)$$

where $T_{Mol}$(Temp,U) MolCounts is the component of transmission T of the Fabry-Pérot interferometer 78 resulting from molecular backscatter, which is a function of temperature and line-of-sight relative wind velocity U; $T_{Aero}$(U)·AeroCounts is the component of transmission T of the Fabry-Pérot interferometer 78 resulting from aerosol backscatter, which is not affected by temperature but is dependent upon the line-of-sight relative wind velocity U; and $T_{Back}$·BackCounts is the component of transmission T of the Fabry-Pérot interferometer 78 resulting from stray light and background wherein $T_{Back}$ is the continuum distribution or illumination profile through the instrument that is measured during calibration of the instrument from the response of the Fabry-Pérot interferometer 78 with the laser seeder 208 turned off, which is representative of the associated spectral distribution from the Fabry-Pérot interferometer 78 that would result from background illumination. During operation of the optical air data system 10, the continuum distribution $T_{Back}$ is obtained from pre-measured values that are stored in memory, and the components $T_{Mol}$ and $T_{Aero}$ are calculated from Equation (21) using the appropriate associated broadening terms. Each of the above-described components of transmission T of the Fabry-Pérot interferometer 78 is in units of counts resulting from the charge collected by the elements of the detector 164.

The distributions $T_{Mol}$(Temp,U), $T_{Aero}$(U) are evaluated with Equation (21) using broadening functions that are appropriate for the molecular and aerosol components of backscatter, respectively. In practice, when evaluating Equation (21), the associated infinite series is truncated to ignore higher-order terms of relatively insignificant value, wherein the level of truncation is either predetermined, or determined during the accumulation of the elements of the series.

Accordingly, the transmission T of the Fabry-Pérot interferometer 78 is modeled with a non-linear model of Equation (31) that is parameterized by a first set (or vector) of parameters P that characterize a particular measurement, i.e. which characterize a particular transmission measure T'; and a second set of parameters Q which are assumed constant during operation of the Fabry-Pérot interferometer 78, the values of which are determined during calibration. Referring to FIG. 30, the first set of parameters P, referred to as observables, include the following elements: line-of-sight relative wind velocity U, static temperature Temp, molecular counts Mol-Counts, aerosol counts AeroCounts, and backscatter counts BackCounts. The second set of parameters Q includes the gap 98, 98.1 (t), index of refraction $\mu$ (1 for an air gap) and reflectivity R of the Fabry-Pérot etalon 90, the nominal wavenumber $\nu$ (or wavelength $\lambda$) of the light 28 from the laser 12, the focal properties of the imaging optics 100 (i.e. $\theta$ in Equation (8)), and the continuum distribution $T_{Back}$.

The observables P can be determined as the values of the parameters P that minimize the following $\chi^2$ merit function:

$$\chi^2(P, Q) = \sum_{n=1}^{N} \frac{[T'(n) - T(M(n); P, Q)]^2}{\sigma^2(n)} \quad (32)$$

using, for example, a Levenberg-Marquardt method of a non-linear least square process which provides for varying smoothly between an inverse-Hessian method and a steepest descent method, as described, along with other suitable non-linear methods, by W.H. Press, S. A. Teukolsky, W. T Veterling, and B. P. Flannery in *Numerical Recipes in C, The Art of Scientific Computing, Second Edition*, Cambridge University Press, 1992, pp. 656-661 and 681-706 which is incorporated herein by reference. In Equation (32), T'(n) is the value of the $n^{th}$ binned pixel 190, and T(M(n),P,Q) is the value of the transmission model T from Equation (31).

Accordingly, for the optical air data system 10, the transmission model T is overdetermined in the sense that the number of elements N of the detector 164, i.e. the number of binned pixels per channel, is of a higher dimension than the number of observables P. For the optical air data system 10 embodiment described herein, there are 5 observables P.

In the inverse Hessian method, the gradient of $\chi^2$ is given by:

$$\beta_k = \frac{\partial \chi^2}{\partial P_k} = -2 \sum_{n=1}^{N} \frac{[T'(n) - T(M(n); P, Q)]}{\sigma^2(n)} \frac{\partial T(M(n); P, Q)}{\partial P_k} \quad (33)$$

and the Hessian is approximated by:

$$\alpha_{kl} = \frac{\partial^2 \chi^2}{\partial P_k \partial P_l} \quad (34)$$

$$= -2 \sum_{n=1}^{N} \frac{\partial T(M(n); P, Q)}{\partial P_k} \frac{\partial T(M(n); P, Q)}{\partial P_l}$$

where k=1 to 5 for the 5 observables.

The observables are then solved by solving the set of linear equations:

$$\sum_{l=1}^{5} \alpha_{kl} \delta P_l = \beta_k \quad (35)$$

where $\delta P_l$ is an vector increment that is to be added to a current approximation for the observable vector $P_l$. This system of equations can be represented as:

$$A \cdot \delta P = B \quad (36)$$

where A is the Hessian matrix, $\delta P$ is a vector of increments to the observables that are to be added to a current approximation for the observable P, and B is the gradient vector. This system of equations can be solved as follows:

$$\delta P = A^{-1} \cdot B \quad (37)$$

where $A^{-1}$ is the inverse Hessian matrix.

The inverse Hessian method is suitable when the $\chi^2$ merit function can be locally approximated by a quadratic form. If a quadratic form is a relatively poor local approximation, then the steepest descent formula can be used to find the increment $\delta P$ of the observable P as follows:

$$\delta P_l = \text{constant} \times \beta_k \quad (38)$$

The Levenberg-Marquardt method provides for a combination of the inverse Hessian and steepest descent methods, wherein the Hessian matrix in Equation (35) is replaced with:

$$\alpha'_{kk} = \alpha_{kk} \cdot (1+\lambda)$$

$$\alpha'_{jk} = \alpha_{jk} \ (j \neq k) \quad (39)$$

and both Equations (35) and (38) are replaced with the following:

$$\sum_{l=1}^{5} \alpha'_{kl} \delta P_l = \beta_k \quad (40)$$

the solution of which is given by:

$$\delta P = A'^{-1} \cdot B \quad (41)$$

where the elements of A' are given by $\alpha'_{jk}$.

The Levenberg-Marquardt method commences with an initial guess for the observable vector P, after which $\chi^2$(P,Q) is calculated, and an initial value of $\lambda$ is chosen (e.g. $\lambda$=0.001). An iterative process then commences with the solution for $\delta P$ of Equation (41), and the evaluation of $\chi^2$(P+$\delta P$,Q). If $\chi^2$(P+$\delta P$,Q)>$\chi^2$(P,Q), then $\lambda$ is increased, e.g. by a factor of 10, and the iteration is repeated. Otherwise, if $\chi^2$(P+$\delta P$,Q)<$\chi^2$(P,Q), then $\lambda$ is decreased, e.g. by a factor of 10, and the iteration is repeated. The iterations on the observable vector P are continued until a stopping criteria is satisfied, for example, on the first or second occasion when $\chi^2$ decreases by a negligible amount, and with the final solution, the method converses towards the inverse Hessian method.

The components of the gradient of the transmission model T used in calculating the gradient of $\chi^2$ and the Hessian matrix are given as follows, and are calculated numerically:

$$\frac{\partial T(U, MolCounts, AeroCounts, Temp, BackCounts)}{\partial U} = \qquad (42)$$
$$\frac{\partial}{\partial U}(T_{Mol}(Temp, U) \cdot MolCounts + T_{Aero}(U) \cdot AeroCounts)$$

$$\frac{\partial T(U, MolCounts, AeroCounts, Temp, BackCounts)}{\partial MolCounts} = \qquad (43)$$
$$T_{Mol}(Temp, U)$$

$$\frac{\partial T(U, MolCounts, AeroCounts, Temp, BackCounts)}{\partial AeroCounts} = T_{Aero}(U) \qquad (44)$$

$$\frac{\partial T(U, MolCounts, AeroCounts, Temp, BackCounts)}{\partial Temp} = \qquad (45)$$
$$\frac{\partial}{\partial Temp} T_{Mol}(Temp, U)$$

$$\frac{\partial T(U, Mol, Aero, Temp, BackCounts)}{\partial BackCounts} = T_{Vack} \qquad (46)$$

When processing the reference channel 120, the observables MolCounts and BackCounts are assumed to be zero valued, and the partial derivatives with respect to MolCounts, BackCounts and Temp of Equations (43), (46) and (45), respectively, are also assumed to be zero.

The $\sigma^2(n)$ weighing term in the $\chi^2$ merit function is the associated variance of the $n^{th}$ measurement channel (i.e. interference order or wavelength), which includes variance of the collected signal in combination with the variance associated with the noise from the detector 164. The collected photons exhibit Poisson noise statistics. Accordingly, for Signal(n) photons/counts/photo-electrons collected on a single channel, the associated variance is equal to the signal level, as follows:

$$\sigma_{Signal}^2(n) = Signal(n) \qquad (47)$$

wherein the Signal(n) is the sum of the molecular, aerosol and background components, i.e.:

$$Signal(n) = Molecular(n) + Aerosol(n) + Background(n) \qquad (48)$$

so that Signal(n) is the predicted value from Equation (31). The total variance is the combination of the signal variance and the variance of the detector, as follows:

$$\sigma^2(n) = Signal(n) + Noise_{Detector}(n)^2 \qquad (49)$$

wherein, for a CCD detector 164.1, the detector noise is the associated read noise on each detector channel.

Alternatively, the observables P could be estimated using other non-linear modeling or non-linear programming techniques, or other techniques such as non-linear estimation or Kalman filtering.

Figure 33:
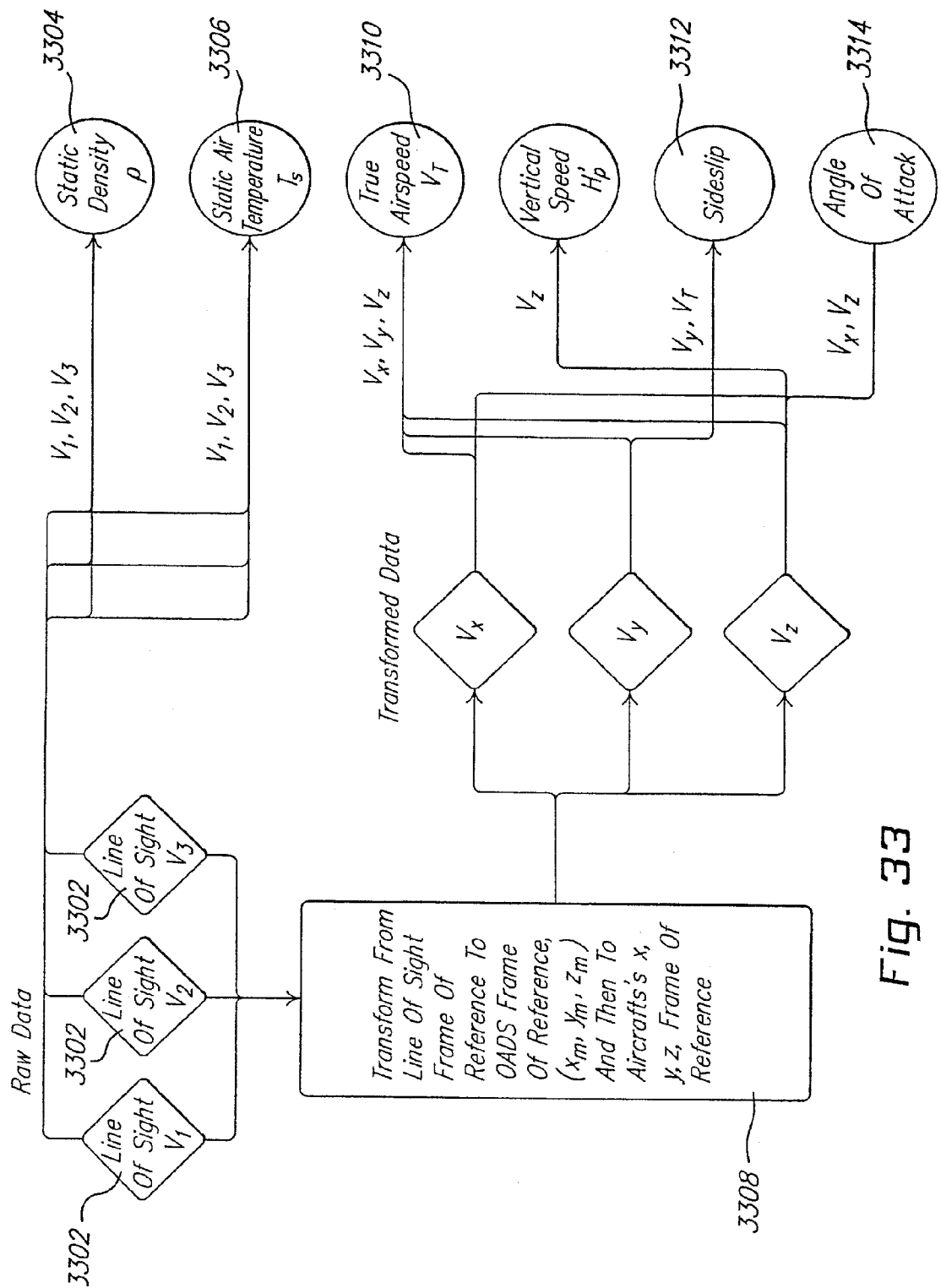
FIG. 33 illustrates a flow chart of a process for determining optical air data system measured air data products.

Referring to FIGS. 29 and 33, in accordance with a first measurement process 3302, the relative wind velocity $V_1$, $V_2$ or $V_3$ is determined along a corresponding line-of-sight direction of the corresponding associated field of view 32 of the associated telescope 26.1, 26.2 and 26.3 for each line of sight 40.1, 40.2 or 40.3 from a difference between the centroids of the associated circular fringe pattern 106.2, 106.3 or 106.4 associated with a corresponding signal channel 122.1, 122.2 or 122.3 in comparison with that of the circular fringe pattern 106.1 associated with the reference channel 120. The fringe position relative to the optic axis 112 directly related to wavelength. Accordingly, a difference in wavelength between the circular fringe patterns 106.2, 106.3 or 106.4 associated with a signal channel 122.1, 122.2 or 122.3 and circular fringe pattern 106.1 associated with the reference channel 120 is a direct measure of the molecular/aerosol Doppler shift in the light 28 that is backscattered from the atmosphere 24 responsive to either molecular or aerosol scattering. The relative wind velocity $V_1$, $V_2$ or $V_3$ for each associated signal channel 122.1, 122.2 or 122.3 is calculated by subtracting the associated line-of-sight velocity U observable solved by Equation (41) from the corresponding "line-of-sight velocity U" observable of the reference channel 120, similarly so solved, so as to provide an associated calibrated relative wind velocity $V_1$, $V_2$ or $V_3$.

Referring to FIGS. 29 and 33, in accordance with a second measurement process 3304, the air density, i.e. static density ρ, is determined from an integral of the molecular signal component 308.2, 310.2 of the circular fringes 108.2, 108.3 or 108.4 associated with a signal channel 122.1, 122.2 or 122.3. The density of the atmosphere 24 is related to molecular density, not aerosol density. Accordingly, the Rayleigh backscatter is separated from the Mie backscatter by spectrally resolving the backscattered light and de-convolving the spectrum into associated molecular and aerosol contributions, which provides for determining the density of the atmosphere 24 from the associated molecular component responsive to the total number of photons therein, i.e. responsive to an integral of the molecular signal component in accordance with Rayleigh scattering theory. The denser the air is, the more molecules are present to scatter light 28 back to the telescope 26 for detection by the associated detector 164. The observables MolCounts and AeroCounts resulting from the solution of the minimization of Equation (32) inherently provides for a deconvolution of the spectrum into the associated molecular and aerosol contributions, i.e. MolCounts is responsive to the integral of the molecular contribution, and AeroCounts is responsive to the integral of the aerosol contribution. Accordingly, static density is given by ρ=C·MolCounts, wherein C is an empirically determined constant that depends upon the parameters that define the optical air data system 10, i.e. the laser power, interaction region, the transmission of the system, the gain of the detectors, the size of the telescope, and the coefficient of backscatter from the atmospheric molecules.

Referring to FIGS. 29 and 33, in accordance with a third measurement process 3306, the absolute temperature, i.e. static temperature $T_S$, of the atmosphere 24 is determined from a width of the molecular signal component 308.2, 310.2 of the circular fringes 108.2, 108.3 or 108.4 associated with a signal channel 122.1, 122.2 or 122.3. The temperature of the atmosphere 24 affects the random thermal motions of the constituent molecules, which causes an associated thermal broadening—referred to as "Doppler broadening" in the field of spectroscopy because of the random velocities in all directions of an ensemble of molecules—of the spectrum of the associated scattered radiation, thereby increasing the associated signal bandwidth which produces correspondingly wider fringes in the associated circular fringe patterns 106.2, 106.3 and 106.4 from the Fabry-Pérot interferometer 78. The absolute temperature of the atmosphere 24 is directly related to this signal bandwidth, and is directly determined as the observable Temp resulting in the solution of the minimization of Equation (32).

Figure 34:
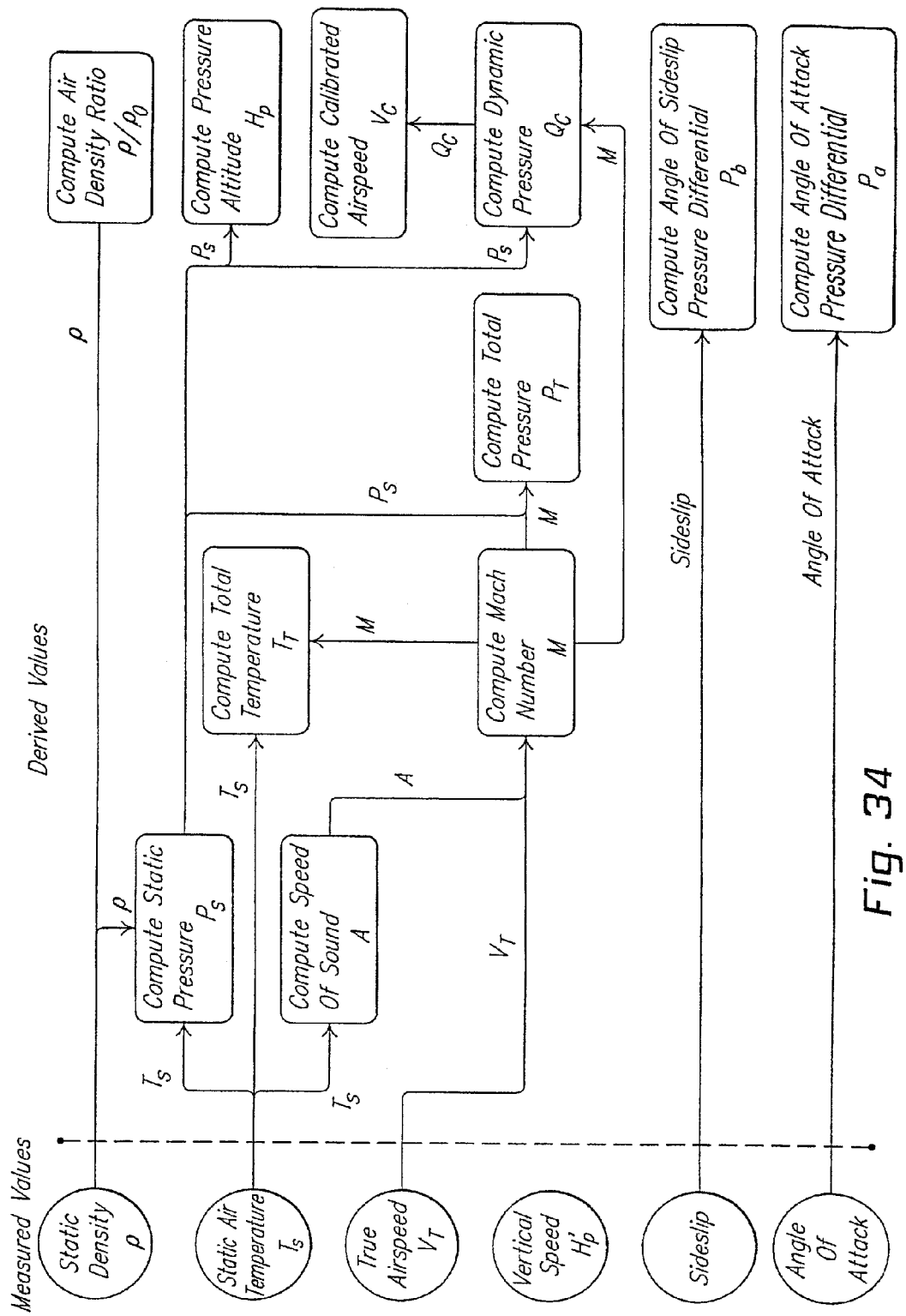
FIG. 34 illustrates a flow chart of a process for determining optical air data system derived air data products.
Figure 35:
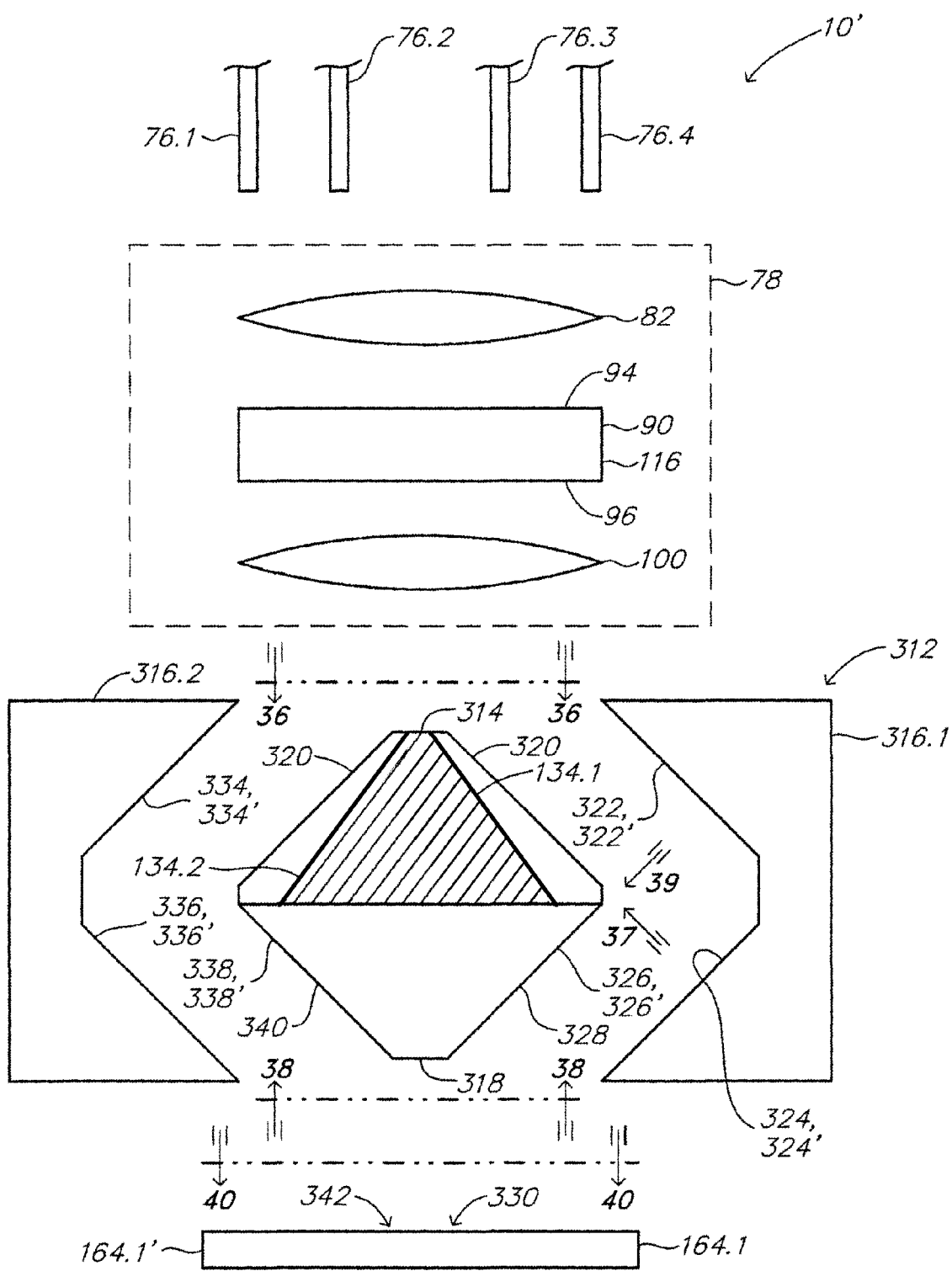
FIG. 35 illustrates a side-view of a signal processor of an optical air data system, including a bi-CLIO element, adapted to provide for measuring wavelength as a function of range.
Figure 36:
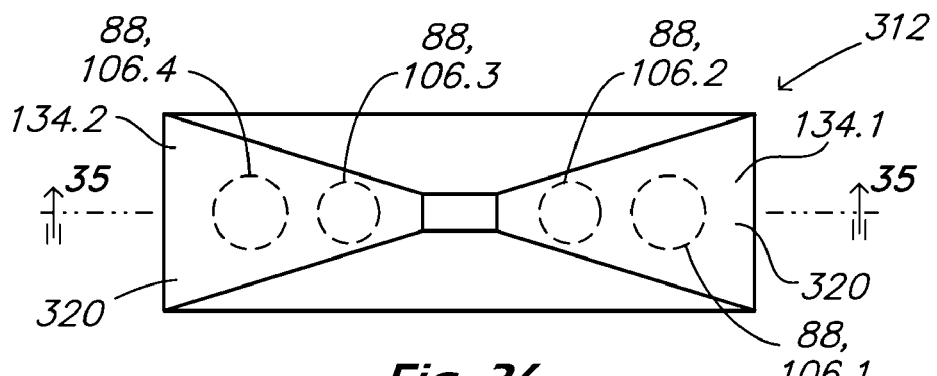
FIG. 36 illustrates a plan view of the bi-CLIO element illustrated in FIG. 35, viewed from the perspective of an associated first pyramidal shaped optic element.
Figure 37:
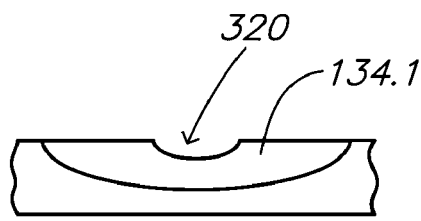
FIG. 37 illustrates a fragmentary end view of a concave conical reflector on a face of the first pyramidal shaped optic element of the bi-CLIO element illustrated in FIGS. 35 and 36, wherein the direction of the end view is substantially parallel to the face of the first pyramidal shaped optic element.
Figure 38:
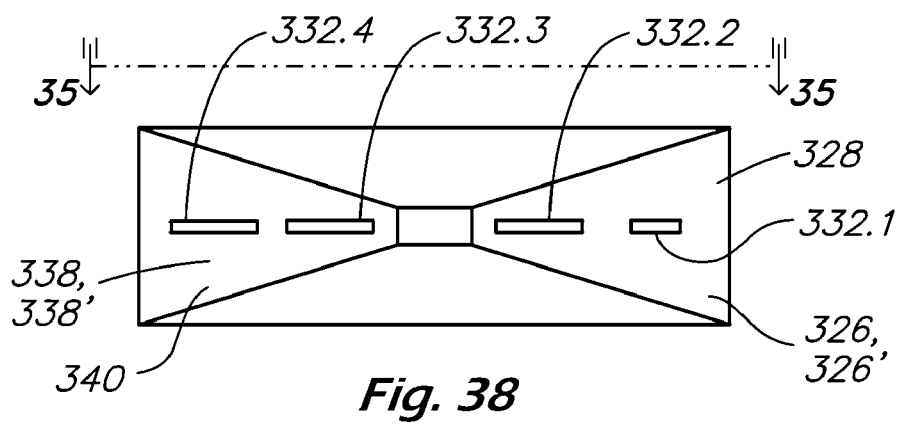
FIG. 38 illustrates a plan view of the bi-CLIO element illustrated in FIG. 35, viewed from the perspective of an associated second pyramidal shaped optic element.
Figure 39:
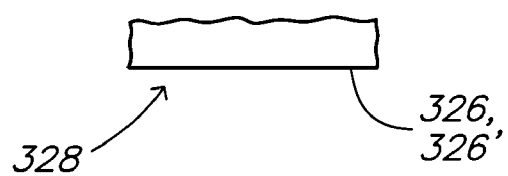
FIG. 39 illustrates a fragmentary end view of a reflective surface on a face of the first second shaped optic element of the bi-CLIO element illustrated in FIGS. 35 and 38, wherein the direction of the end view is substantially parallel to the face of the second pyramidal shaped optic element.

Referring to FIG. 33, various other measured air data products may be calculated as follows: In accordance a fourth measurement process 3308, the relative wind velocities $V_1$, $V_2$ and $V_3$ determined by the first measurement process 3302 along corresponding line-of-sight directions of the corresponding associated field of view 32 of the associated telescope 26.1, 26.2 and 26.3 for each lines of sight 40.1, 40.2 or 40.3 are first transformed from a line-of-sight frame of reference to a frame of reference ($x_m$, $y_m$ and $z_m$) of the optical air data system 10, and then to a frame of reference (x, y, z) of the aircraft 38 using known transformations, so as to provide the relative wind velocities $V_X$, $V_Y$ and $V_Z$ in the frame of reference (x, y, z) of the aircraft 38, from which the true airspeed $V_T$ may be calculated from the relative wind velocities $V_X$, $V_Y$ and $V_Z$ in accordance with a fifth measurement process 3310. The vertical speed $H'_P$ is given by the Z-component of relative wind velocity $V_Z$. The sideslip may be calculated from the Y-component of relative wind velocity $V_Y$ and the true airspeed $V_T$ in accordance with a sixth measurement process 3312. The angle of attack may be calculated from the X and Z-components of relative wind velocity $V_X$ and $V_Z$ in accordance with a seventh measurement process 3314. The Aerosol-to-Total Scattering Ratio (ASR) may also be calculated as the ratio of the observable AeroCounts to the sum of the observables MolCounts, AeroCounts and BackCounts. Referring to FIG. 34, the measured values of static density ρ, static temperature $T_S$, true airspeed $V_T$, sideslip and angle of attack may then be used to compute the following derived values using associated known relations and processes: air density ratio, static pressure, total pressure, pressure altitude, total temperature, speed of sound, Mach number, dynamic pressure, calibrated airspeed, angle of sideslip pressure differential, and angle of attack pressure differential.

Figure 3:
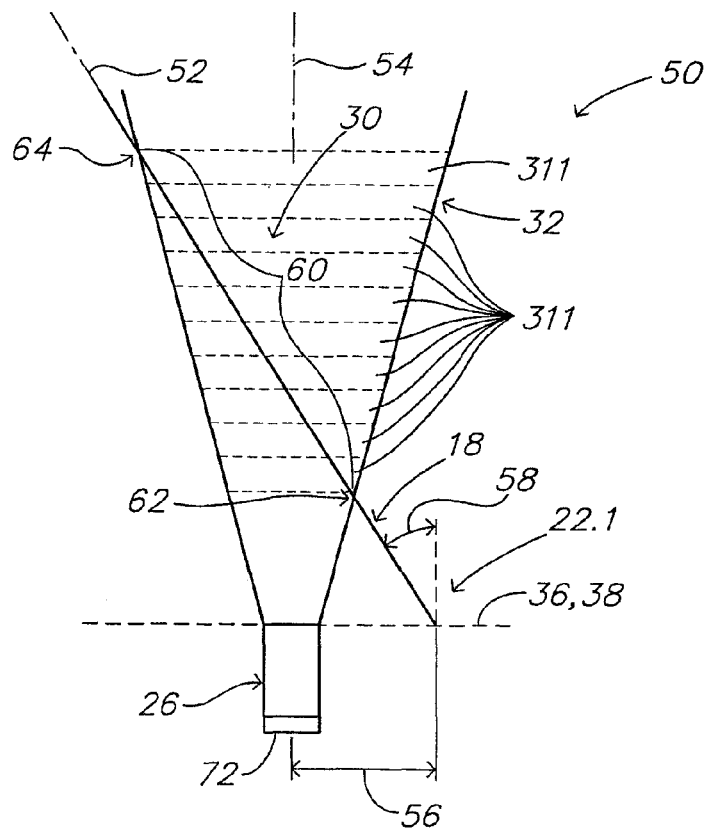
FIG. 3 illustrates an optical head of a biaxial system.

Referring to FIGS. 3 and 4, the optical air data system 10, either with an optical head 22.1 incorporating a biaxial system 50 (also known as a bistatic system) as illustrated in FIG. 3, or with an optical head 22.2 incorporating a coaxial system 66 as illustrated in FIG. 4, may be adapted as either a non-ranging system or a ranging system. In the non-ranging embodiment, the measurement volume consists of one region that spans the entire interaction region between the field of view 32 of the associated telescope 26.1, 26.2, 26.3 and the line of sight 40.1, 40.2, 40.3 of the associated second laser beam 18.1, 18.2 and 18.3.

Accordingly, referring also to FIGS. 35-42, in accordance with another aspect, an optical air data system 10', either with an optical head 22.1 incorporating a biaxial system 50 or with an optical head 22.2 incorporating a coaxial system 66 (also known as a monostatic system), may be adapted so as to provide for air data products as a function of range 46. In the ranging embodiment, a sufficiently fast CCD detector 164.1 is responsive to the time of flight of each laser pulse, thereby providing for multiple range-separated measurement volumes 311 extending out along the line of sight 40.1, 40.2, 40.3 of the associated telescope 26.1, 26.2, 26.3, so as to provide for mapping the air data products as they vary along the line of sight 40.1, 40.2, 40.3 extending out from the optical head 22.1, 22.2, e.g. from an associated aircraft 38 for which the associated range-based air data products can be used by associated flight guidance and planning algorithms.

Referring to FIGS. 35-40, the optical air data system 10' incorporates a bi-CLIO 312, for example, comprising a first pyramidal shaped optic element 314 which cooperates with first 316.1 and second 316.2 corner reflector optic elements, which in turn cooperate with a second pyramidal shaped optic element 318. Two of the opposing side faces 320 of the first pyramidal shaped optic element 314 incorporate associated first 134.1 and second 134.2 concave conical reflectors adapted to receive an associated circular fringe patterns 106.1 and 106.2, and 106.3 and 106.4, respectively, from the Fabry-Pérot interferometer 78, wherein the associated fiber optics 76.1, 76.2, 76.3 and 76.4 inputting to the Fabry-Pérot interferometer 78 are arranged substantially in-line with a center of the first 314 and second 318 pyramidal shaped optic elements. The first concave conical reflector 134.1 is adapted to receive a first two circular fringe patterns 106.1, 106.2, and the second concave conical reflector 134.2 is adapted to receive the remaining two circular fringe patterns 106.3 and 106.4.

Light signals 88 of the first two circular fringe patterns 106.1, 106.2 are reflected from the first concave conical reflector 134.1 onto a first reflective surface 322 of the corresponding first corner reflector optic element 316.1, and then reflected therefrom onto a second reflective surface 324 of the corresponding first corner reflector optic element 316.1, and then reflected therefrom onto a third reflective surface 326 on a first side face 328 of the second pyramidal shaped optic element 318, and finally reflected therefrom onto a first portion 330 an associated CCD detector 164.1 as corresponding first 332.1 and second 332.2 linear fringe patterns. Similarly, light signals 88 of the remaining two circular fringe patterns 106.3 and 106.4 are reflected from the second concave conical reflector 134.2 onto a fourth reflective surface 334 of a corresponding second corner reflector optic element 316.2, and then reflected therefrom onto a fifth reflective surface 336 of the corresponding second corner reflector optic element 316.2, and then reflected therefrom onto a sixth reflective surface 338 on a second side face 340 of the second pyramidal shaped optic element 318, and finally reflected therefrom onto a second portion 342 an associated CCD detector 164.1 as corresponding third 332.3 and fourth 332.4 linear fringe patterns. For example, in one embodiment, the first 322, second 324, third 326, fourth 334, fifth 336 and sixth 338 reflective surfaces comprise corresponding planar reflective surfaces 322', 324', 326', 334', 336', 338'. The first 314 and second 318 pyramidal shaped optic elements and the first 316.1 and second 316.2 corner reflector optic elements can be constructed from a variety of materials—including, but not limited to, aluminum, stainless steel, copper-nickel alloy, glass or fused quartz—that can be adapted to incorporate associated reflective surfaces or coatings. Furthermore, one or both of the first 316.1 and second 316.2 corner reflector optic elements could be replaced with separate elements for each of the associated first 322, second 324, fourth 334 and fifth 336 reflective surfaces.

Figure 40:
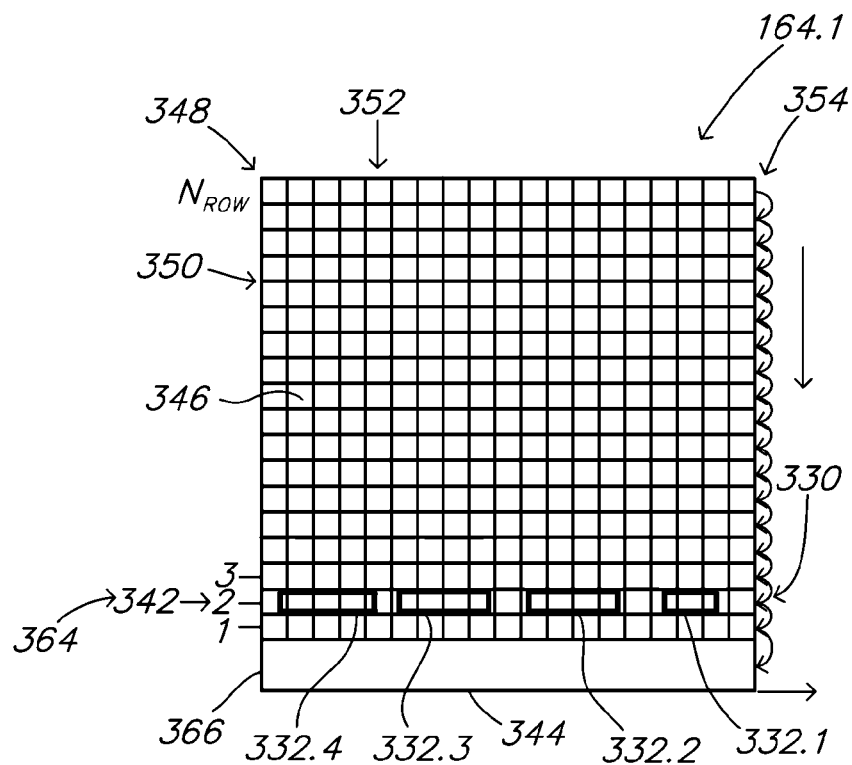
FIG. 40 illustrates a plan view of a CCD detector illustrated in FIG. 35, and an associated imaging process.
Figure 41:
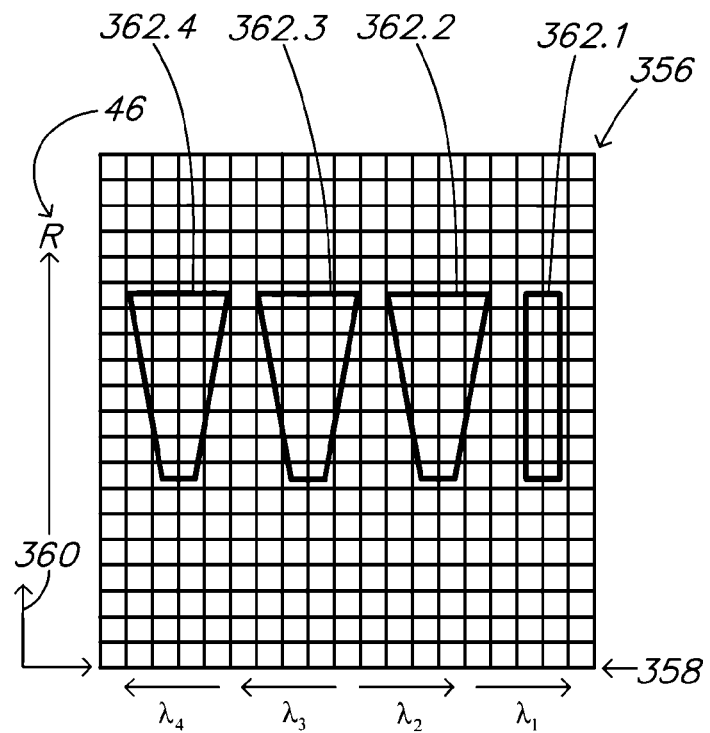
FIG. 41 illustrates an image from the CCD detector illustrated in FIG. 40.

Referring to FIGS. 40 and 41, the first 332.1, second 332.2, third 332.3 and fourth 332.4 linear fringe patterns are projected onto the associated first 330 and second 342 portions of the CCD detector 164.1 located proximate to an associated serial register 344 thereof, and the remaining photosites 346 of the CCD detector 164.1 are masked from receiving light. The CCD detector 164.1 comprises an array 348 of photosites 346 organized as a plurality of rows 350, each row comprising a plurality of columns 352. Upon exposure to light, each of the photosites 346 accumulates charge in proportion to the amount of light impinging thereon. In a normal process of recording a 2-dimensional image, the entire array 348 is simultaneously exposed to an entire image, e.g. by the opening of an associated shutter or by the activation of the laser 12 illumination source. Then, with the shutter closed or the laser 12 off after the light signals 44 have been received, the 2-dimensional image is read from the array 348, one row 350 at a time, by successively shifting the charges from each row 350 successively downwards, for example, by first shifting the charges from row #1 into the serial register 344, then shifting the charges from row #2 into row #1, then row #3 into row #2, and so on until the charges from row #N is shifted into row #N−1. The contents of the serial register 344 are then A/D converted and communicated to an associated processor for subsequent processing. Afterwards, this process repeats on rows #1 to #N−1, and so on until the last row 350 of recorded photosites 346 has been transferred to the serial register 344, and then to the associated processor for subsequent processing.

The optical air data system 10' takes advantage of the normal process by which the CCD detector 164.1 is read to provide for continuously recording the first 332.1, second 332.2, third 332.3 and fourth 332.4 linear fringe patterns over time so that each subsequent row 350 of photosites 346 passing by first 330 and second 342 portions of the CCD detector 164.1 during the process of reading the CCD detector 164.1 captures the associated first 332.1, second 332.2, third 332.3 and fourth 332.4 linear fringe patterns at a corresponding subsequent point in time with data associated with a corresponding range 46 from the optical head 22.1, 22.2. More particularly, the process of reading the CCD detector 164.1 commences simultaneously with the generation of an associated light pulse from the laser 12. Light signals 88 are continuously processed by the Fabry-Pérot interferometer 78 and associated bi-CLIO 312 so as to illuminate the first 330 and second 342 portions of the CCD detector 164.1 with corresponding first 332.1, second 332.2, third 332.3 and fourth 332.4 linear fringe patterns. In the CCD detector 164.1 illustrated in FIG. 40, the first 330 and second 342 portions of the CCD detector 164.1 are aligned with row #2 thereof. After the charges from row #2 are transferred to row #1 during a charge transfer cycle 354, row #2 is replaced with the blank contents of row #3, which then becomes exposed to the light signals 88 from the first 332.1, second 332.2, third 332.3 and fourth 332.4 linear fringe patterns at that time. This process repeats with a fresh row of blank photosites 346 replacing the contents of row #2 with each subsequent charge transfer cycle 354 until all of the rows 350 have been read. During each charge transfer cycle 354, the contents of row #1 are shifted into the serial register 344, and then transferred to the data processor 198 where the corresponding values are stored in memory 202 as pixels 180 of an associated image 356, beginning from the bottom 358 of the image 356, and progressing upwards 360 until the entire image 356 has been recorded, as illustrated in FIG. 41, whereupon the image 356 records each of the first 332.1, second 332.2, third 332.3 and fourth 332.4 linear fringe patterns in corresponding range-resolved fringe patterns 362.1, 362.2, 362.3 and 362.4, with range 46(R) increasing upwards 360 in the associated image 356. The range resolution of the image 356 is dependent upon the time required for each charge transfer cycle 354, i.e. the time required to transfer the associated charges from one row to the next. For example, for a CCD detector 164.1 with 512 rows and a row shift rate of 375 nanoseconds per row, the range resolution would be 56.25 meters (i.e. $3.0 \times 10^8$ m/s*½*375× $10^{-9}$ s) and the maximum range for the CCD detector 164.1 would be 28.8 Kilometers (i.e. 512*56.25). The frame transfer/streaking process/range acquisition takes only a relatively short time, e.g. for 512 rows at a streak rate of 375 ns/row it takes 192 micro-seconds to resolve the full range on the CCD detector 164.1. For a 200 Hz refresh rate a frame is acquired every 5 milliseconds (1/200), so there are 0.00500−0.000192=0.004808 seconds for reading the image out of the readout registers and transferring to disk in accordance with an associated process of acquiring image frames from the CCD detector 164.1 at an associated refresh rate thereof, e.g. in frames per second.

Figure 42:
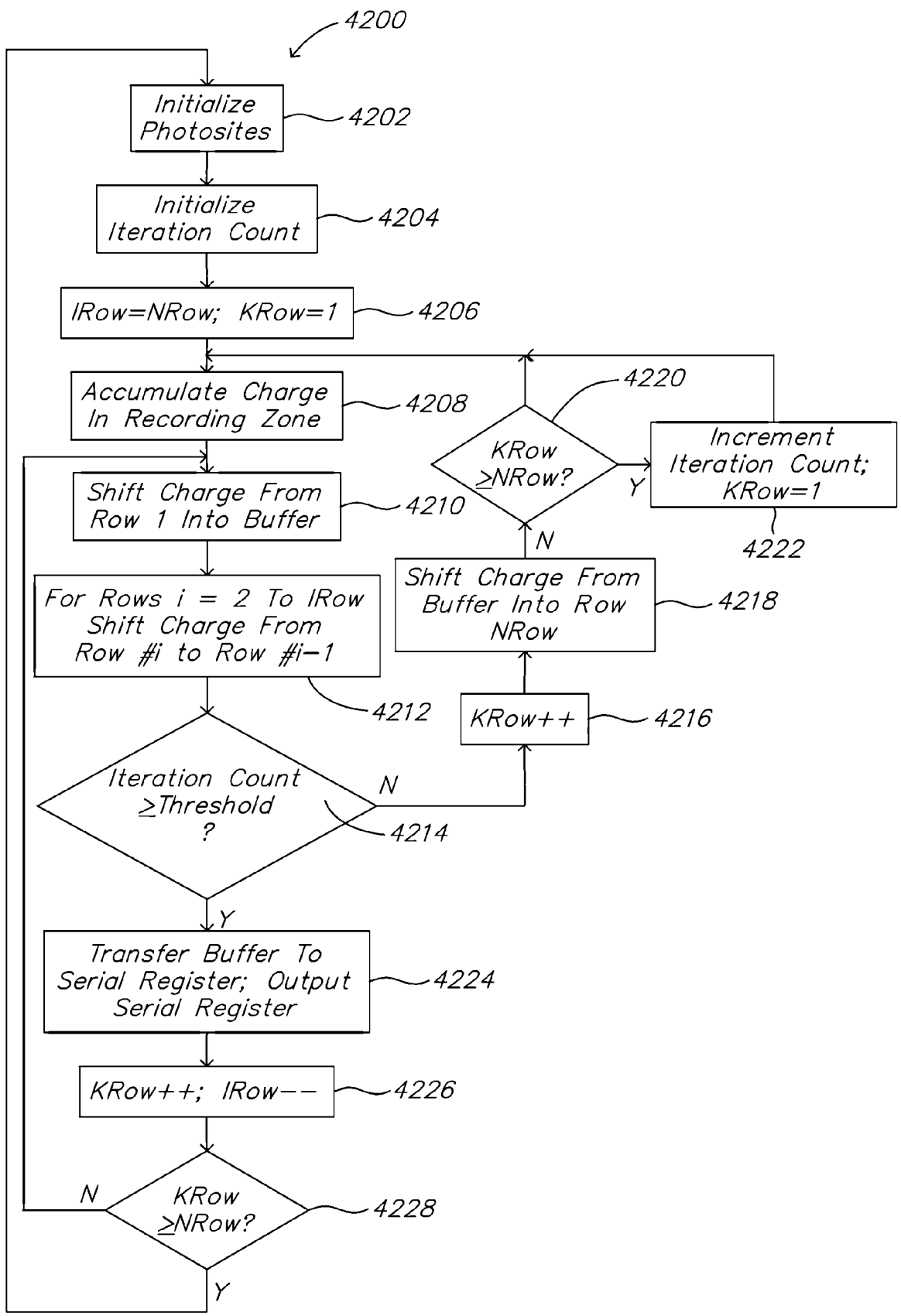
FIG. 42 illustrates a flow chart of a first imaging process for generating range-resolved images.

Referring to FIG. 42, in accordance with a first imaging process 4200 for generating a range-resolved image, for example, operative in cooperation with the CCD detector 164.1 illustrated in FIG. 40 to generate an associated image 356, e.g. as illustrated in FIG. 41, in step (4202), the array 348 of photosites 346 of the CCD detector 164.1 is initialized, e.g. to substantially zero charge. Then, in step (4204), in synchronism with the lasing of the second laser beams 18 from the laser 12, for a pulsed laser 12, an iteration count is initialized, e.g. to a value of zero, wherein the iteration count is used to record the number of times the array 348 of photosites 346 has been processed in subsequent steps. Then, in step (4206), a first row counter IRow is initialized to a value of NRow, where NRow is the number of rows in the array 348 of photosites 346; and a second row counter KRow is initialized to a value of 1. Then, in step (4208), an iterative process commences, wherein charge is accumulated in the photosites 346 in a recording zone 364 comprising the first 330 and second 342 portions of the CCD detector 164.1 that are aligned with a particular row of the array 348 of photosites 346 and which receive light 28 of the first 332.1, second 332.2, third 332.3 and fourth 332.4 linear fringe patterns from the associated fiber optics 76.1, 76.2, 76.3 and 76.4. Then, in step (4210), the charges in the photosites 346 of row #1 are shifted into a buffer row 366, and then, in step (4212), the charges in row ##2 to IRow are shifted into row ##1 to IRow−1, respectively. Then, in step (4214), if the iteration count is less than a threshold, then in step (4216), the second row counter KRow is incremented, and, in step (4218), the charges in the buffer row 366 are shifted into Row #NRow. Then, in step (4220), if the value of the second row counter KRow is greater than or equal to the number of rows NRow, then, in step (4222), the iteration count is incremented and the second row counter KRow is initialized to a value of 1. Then, from step (4222), or otherwise from step (4220), the process of steps (4208) through (4212) is repeated until, in step (4214), the iteration count is greater than or equal to the threshold, in which case, in step (4224), the charges are transferred from the buffer row 366 to the serial register 344 and then output so as to generate the image 356. Then, in step (4226), the second row counter KRow is incremented and the first row counter IRow is decremented. If, in step (4228), the value of the second row counter KRow is less than the number of rows NRow, then the process repeats with step (4210) until the entire image 356 has been transferred from the array 348 of photosites 346; otherwise, the process of recording and outputting an image 356 repeats with step (4202). Accordingly, the second row counter KRow provides for determining whether each row of the array 348 of photosites 346 has been recorded, the iteration count provides for repetitively recording the entire array 348 of photosites 346 so as to accumulate additional charge within each of the photosites 346, thereby improving the associate ratio of charge (signal) to read noise, and the first row counter IRow provides for efficiently reading the array 348 of photosites 346.

Referring to FIGS. 43a-e, a second embodiment of a CCD detector 164.1' comprises an imaging region 368 and a masked, frame-transfer region 370, wherein the frame-transfer region 370 provides for buffering the image 356 so as to facilitate transfer thereof from the CCD detector 164.1' via a relatively slow serial register 344. Both the imaging region 368 and the frame-transfer region 370 contain similar photosites 346 that are adapted to store photo-generated charges, the difference being that the frame-transfer region 370 is masked from light, and thereby unable to generated photo-generated charges. Although the second embodiment of the CCD detector 164.1' is suitable for use in any of the above-described embodiments of the optical air data system 10, 10', it will now be described with particularity in cooperation with the optical air data system 10' illustrated in FIGS. 35-42, for example, in cooperation with a second imaging process 4400 illustrated in FIG. 44.

Figure 44:
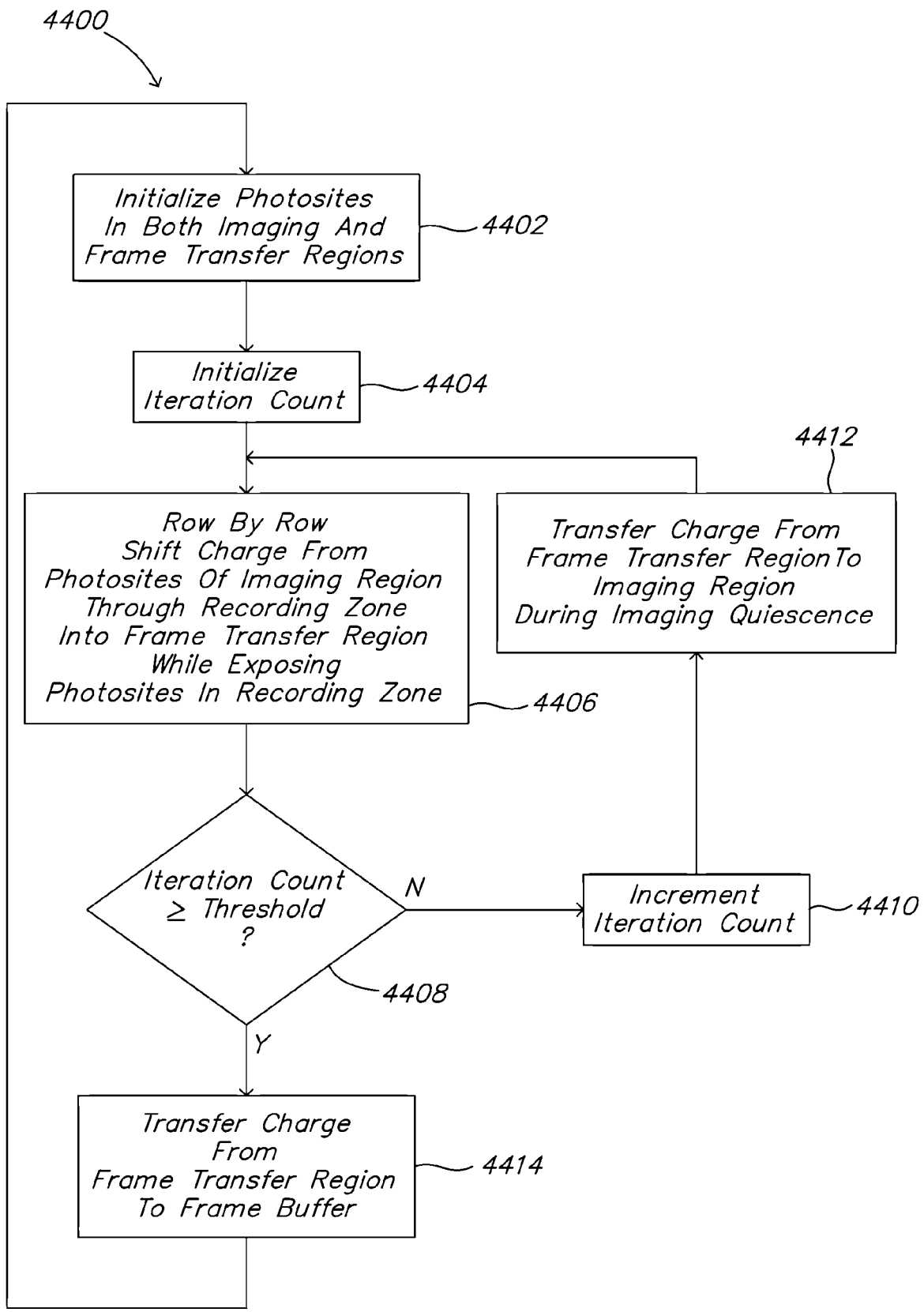
FIG. 44 illustrates a flow chart of a second imaging process for generating range-resolved images.

Referring to FIGS. 43a and 44, in step (4402), the photosites 364 in both the imaging region 368 and the frame-transfer region 370 of the CCD detector 164.1' are initialized, for example, to a condition of substantially zero charge, for example, as may result from an associated read process of the CCD detector 164.1'. Then, in step (4404), in synchronism with the second laser beams 18 from the laser 12, for a pulsed laser 12, an iteration count is initialized, e.g. to a value of zero, wherein the iteration count is used to record the number of times the imaging region 368 has been recorded in subsequent steps. Then, in step (4406), the charges in the array 348 of photosites 346 are shifted downwards, row by row, from the imaging region 368 into the frame-transfer region 370, through the recording zone 364 therebetween, wherein the photosites 346 in the recording zone 364 are exposed to the first 332.1, second 332.2, third 332.3 and fourth 332.4 linear fringe patterns, the light of which causes charges to be generated within the associated photosites 346, which charges are then subsequently shifted downwards. For example, FIG. 43b illustrates a beginning stage of an image recording cycle, at which time the lowest row of photosites 346 of the imaging region 368 are recorded; FIG. 43c illustrates an intermediate stage of the image recording cycle at which time a portion of the photosites 346 of the imaging region 368 have been recorded and the charges therefrom have been shifted into the frame-transfer region 370, and FIG. 43d illustrates a final stage of the image recording cycle at which time all of the photosites 346 of the imaging region 368 have been recorded and the charges therefrom have been shifted into the frame-transfer region 370. Then, in step (4408), if the iteration count is less than a threshold, then, in step (4410), the iteration count is incremented, and, in step (4412), the charges are transferred from the frame-transfer region 370 back to the imaging region 368 of the CCD detector 164.1', after which the process repeats with step (4406) until, in step (4408), the iteration count is greater than or equal to the threshold, after which, in step (4414), the charges are transferred from the frame-transfer region 370 to a frame buffer 372 via a serial register 344 operatively associated with the frame-transfer region 370 of the CCD detector 164.1', as illustrated in FIG. 43e, and then the process repeats with step (4402). Accordingly, the iteration count provides for repetitively recording the imaging region 368 so as to accumulate additional charge within each of the photosites 346 thereof, thereby improving the associate ratio of charge (signal) to read noise. The cumulative recording process is illustrated by the portions of the of the range-resolved fringe patterns 362.1, 362.2, 362.3 and 362.4 in FIGS. 43b and 43c with dashed outlines.

The range-resolved fringe patterns 362.1, 362.2, 362.3 and 362.4 in the images 356 illustrated in FIGS. 41 and 43e are simulations of measurements from a high-altitude or space-based optical air data system 10' looking down on the atmosphere 24, wherein each range-resolved fringe patterns 362.1, 362.2, 362.3 and 362.4 comprises a single fringe 310. For the range-resolved fringe patterns 362.2, 362.3 and 362.4 associated with the signal channels 122.1, 122.2 and 122.3, the width and amplitude of the range-resolved fringe patterns 362.1, 362.2, 362.3 and 362.4, i.e. the molecular signal component 310.2 thereof, increases with increasing range 46 corresponding to an increase in density and temperature with decreasing altitude in the atmosphere 24, whereas the range-resolved fringe patterns 362.1 associated with the reference channel 120 exhibits a substantially constant width.

Figure 45:
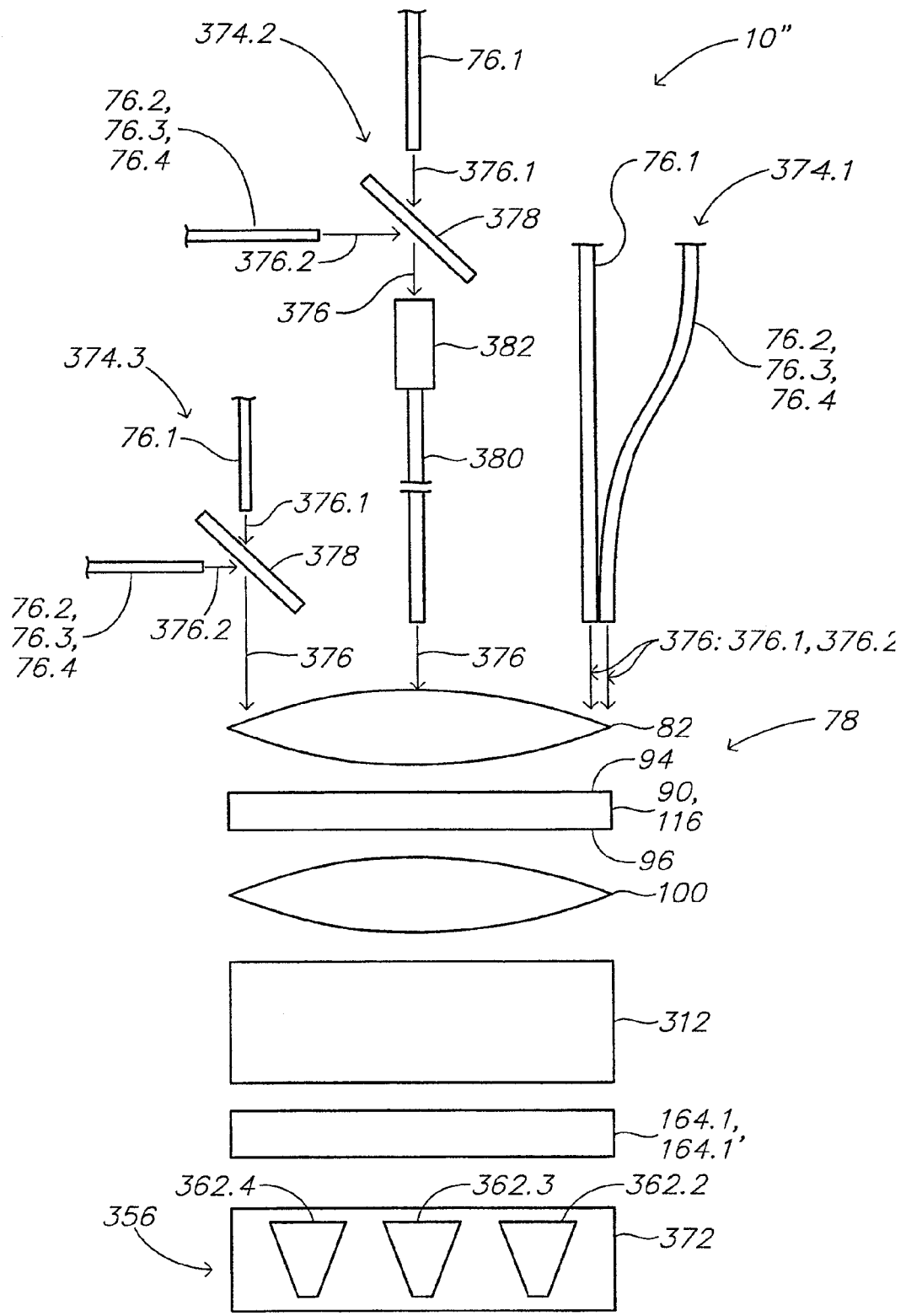
FIG. 45 illustrates various embodiments for multiplexing reference and signal channels for a range-resolved optical air data system.

Referring to FIG. 45, in accordance with an alternative embodiment of an optical air data system 10'', the reference channel 120 can be multiplexed with one or more signal channels 122.1, 122.2 and 122.3 so as to provide for eliminating the separate and distinct processing of the reference channel 120 by the optical air data system 10''. For example, in accordance with a first embodiment of an optical multiplexer 374.1, the fiber optic 76.1 of the reference channel 120 is bunched together with the fiber optic 76.2, 76.3, 76.4 of one of the signal channels 122.1, 122.2 or 122.3 so that the light 376.1, 376.2 from the reference 120 and signal 122.1, 122.2, 122.3 channels illuminates a common region of the Fabry-Pérot interferometer 78 as a multiplexed beam of light 376. As another example, in accordance with a second embodiment of an optical multiplexer 374.2, light 376.1 from the fiber optic 76.1 of the reference channel 120 is combined with light 376.2 from a fiber optic 76.2, 76.3, 76.4 of one of the signal channels 122.1, 122.2 or 122.3 using a beam splitter 378 so as to form a multiplexed beam of light 376, which is then collected into a fiber optic 380 by a light-collecting element 382, for example, a GRIN lens or an aspheric lens, and directed therethrough to the Fabry-Pérot interferometer 78. As yet another example, in accordance with a third embodiment of an optical multiplexer 374.3, light 376.1 from the fiber optic 76.1 of the reference channel 120 is combined with light 376.2 from a fiber optic 76.2, 76.3, 76.4 of one of the signal channels 122.1, 122.2 or 122.3 using a beam splitter 378 so as to form a multiplexed beam of light 376, which is directed via an associated optical path to the Fabry-Pérot interferometer 78, either directly, or indirectly using one or more associated mirrors.

The multiplexed beam of light 376 is processed by the Fabry-Pérot interferometer 78, transformed into an associated linear fringe pattern 332.2, 332.3 or 332.4 by the associated bi-CLIO 312, and imaged onto an associated CCD detector 164.1, 164.1' which provides for generating an associated range-resolved fringe pattern 362.2, 362.3 or 362.4, wherein the information associated with the zero or near-zero range portion thereof corresponds to the reference channel 120, and the remaining information corresponds to the associated signal channel 122.1, 122.2 or 122.3. Although FIG. 45 illustrates three multiplexed channels, so as to illustrate the three different associated optical multiplexers 374.1, 374.2 and 374.3, it should be understood that the optical air data system 10'' can function using only one optical multiplexer 374.1, 374.2 or 374.3 to provide the information from the reference channel 120.

Referring to FIGS. 3 and 4, the optical air data systems 10', 10'' that provide for range-resolved imaging and associated range-resolved air data products can be adapted to incorporate or cooperate with either a biaxial system 50, e.g. as illustrated in FIG. 3, or a coaxial system 66, e.g. as illustrated in FIG. 4, wherein different rows in the image 356 of the range-resolved fringe patterns 362.2, 362.3 and 362.4 are associated with different range-separated measurement volumes 311 within the associated interaction regions 30.

Figure 46:
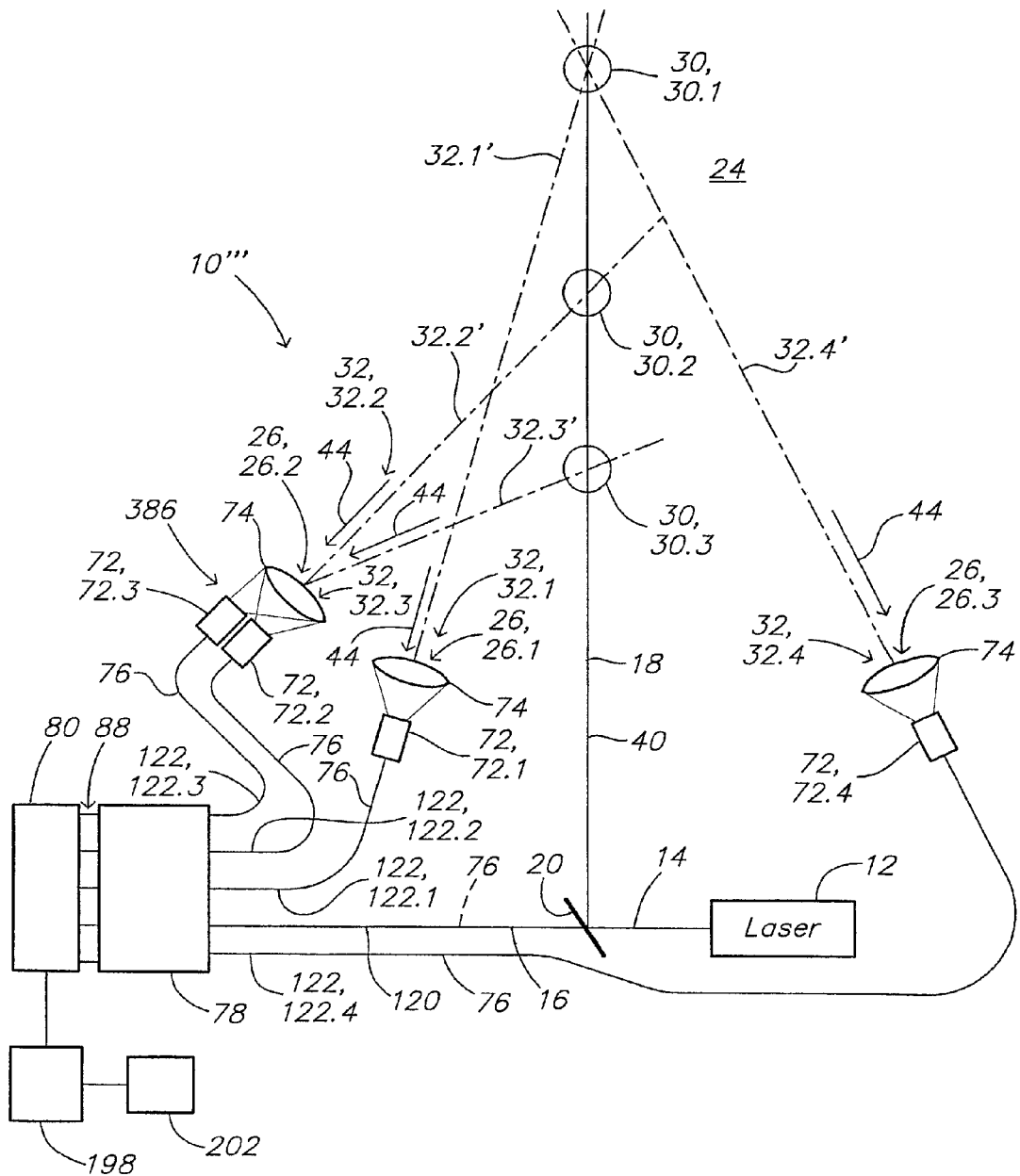
FIG. 46 illustrates various interaction regions associated with a common line of sight of a second laser beam.

Referring to FIG. 46, in accordance with alternative embodiments, an optical air data system 10''' in a biaxial system 50 configuration may be adapted with a plurality of different fields of view 32, each of which cooperates with a common line of sight 40 of an associated second laser beam 18. A telescope 26 and an associated final light-collecting element 72 is adapted for each associated field of view 32 to collect associated light signals 44 backscattered from associated interaction regions 30 defined by the intersection of the associated field of view 32 with the second laser beam 18 along the line of sight 40. Each of the light signals 44 associated with the different fields of view 32 are then processed by an associated Fabry-Pérot interferometer 78, detection system 80, and data processor 198 as separate signal channels 122, together with an associated reference channel 120 of an associated reference beam 16, as described hereinabove for the previously described embodiments.

In accordance with one aspect, the different fields of view 32 may be associated with corresponding different ranges along the line of sight 40. For example, for a line of sight 40 spanning a range of altitudes, each different field of view 32 provides for measuring an associated set of air data products at a corresponding different altitude. In one embodiment, for example, a first final light-collecting element 72.1 in cooperation with a first telescope 26.1 aligned with a first axis 32.1' associated with a first field of view 32.1 provides for collecting backscattered light signals 44 from a first interaction region 30.1 located at a first range from the beam splitter optic 20 from which the second laser beam 18 originates. A second final light-collecting element 72.2 at a first light-collecting location in cooperation with a second telescope 26.2 aligned with a second axis 32.2' associated with a second field of view 32.2 provides for collecting backscattered light signals 44 from a second interaction region 30.2 located at a second range from the beam splitter optic 20. A third final light-collecting element 72.3 at a second light-collecting location in cooperation with the second telescope 26.2 aligned with a third axis 32.3' associated with a third field of view 32.3 provides for collecting backscattered light signals 44 from a third interaction region 30.3 located at a third range from the beam splitter optic 20. For example, in one embodiment, the first and second light-collecting locations associated with the second telescope 26.2 are transversely offset from one another in the focal plane 386 of the associated lens system 74 of the second telescope 26.2, the first and second light-collecting locations thereby defining the corresponding associated second 32.2 and third 32.3 fields of view. It should be understood that the particular plurality of final light-collecting element 72 associated with a particular telescope 26 is not limiting, i.e. the actual number being limited by the physical size of the final light-collecting elements 72 and the size of the associated lens system 74.

In accordance with another aspect, the different fields of view 32 may be associated with a common interaction region 30 along the line of sight 40, for example, so as to provide for measuring different line-of-sight relative wind velocities U in different directions relative to a common region of the atmosphere 24, so that relative to an inertial frame of reference, each measurement is affected by substantially the same wind velocity of the atmosphere relative to the inertial frame of reference, so as to improve the accuracy of an associated relative wind vector calculated from the associated line-of sight-relative wind velocities U. In one embodiment, for example, a first final light-collecting element 72.1 in cooperation with a first telescope 26.1 aligned with a first axis 32.1' associated with a first field of view 32.1 provides for collecting backscattered light signals 44 from a first interaction region 30.1, and a fourth final light-collecting element 72.4 in cooperation with a third telescope 26.3 aligned with a fourth axis 32.4' associated with a fourth field of view 32.4 also provides for collecting backscattered light signals 44 from the first interaction region 30.1, but from a different direction, so that the light signals 44 from the first 72.1 and fourth 72.4 final light-collecting elements provide for measuring line-of-sight relative wind velocities U in different directions so as to provide for measuring an associated relative wind vector. The first 72.1 and fourth 72.4 final light-collecting elements in the embodiment illustrated in FIG. 46 provide for determining an associated 2-D relative wind vector in the plane defined by the first 32.1' and fourth 32.4' axes. An additional out-of-plane final light-collecting element 72 in cooperation with an associated telescope 26 having an associated field of view 32 also aligned with the first interaction region 30.1 may be used to provide for determining an associated 3-D relative wind vector.

Figure 47:
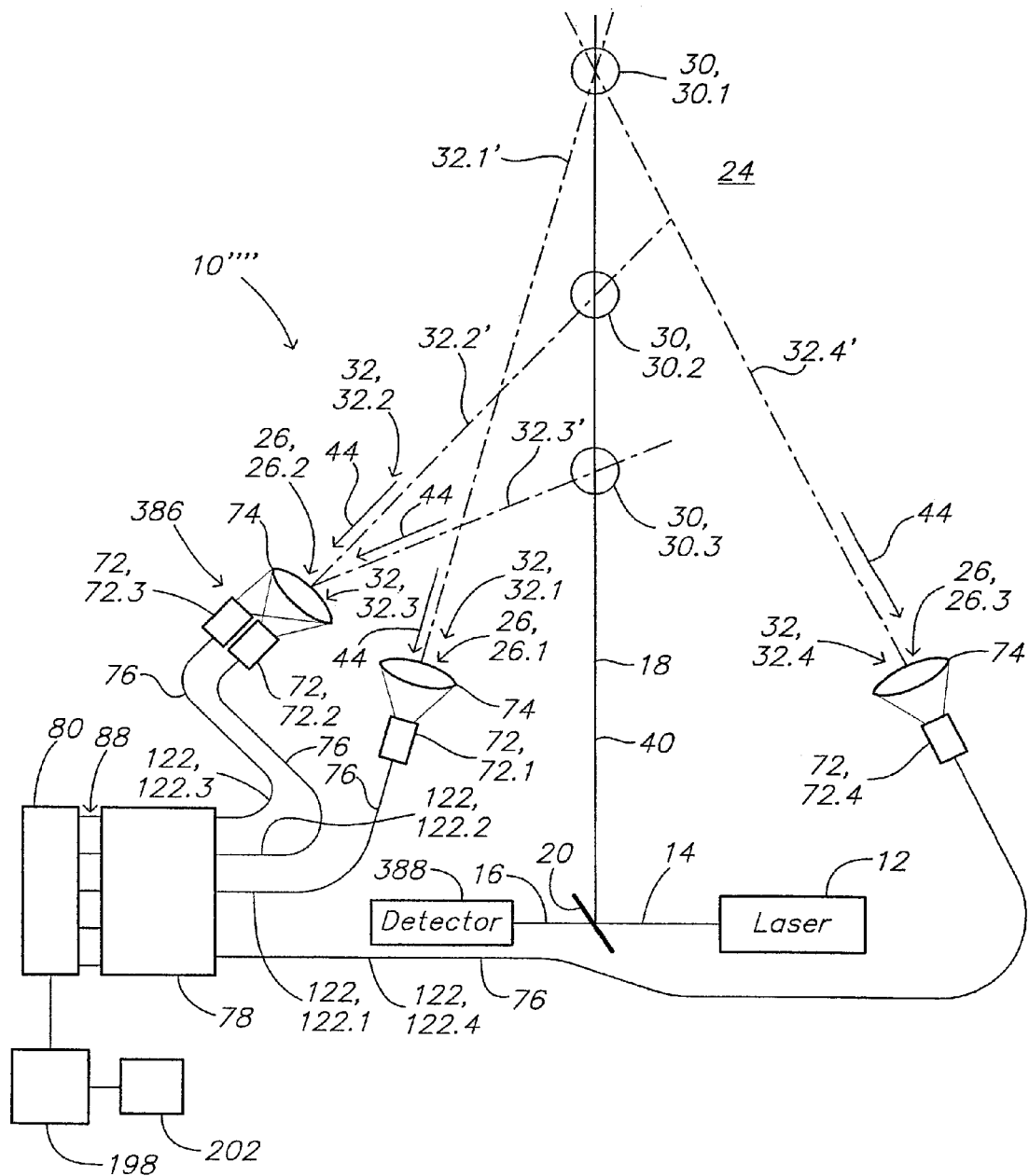
FIG. 47 illustrates an alternative to the various embodiments illustrated in FIG. 46, suitable for determining air data products that are not dependent upon relative wind velocity.

Referring to FIG. 47, an optical air data system 10'''' may be adapted to measure the overall intensity of the reference beam 16 with a detector 388, rather than processing the reference beam through the Fabry-Pérot interferometer 78, so as to provide for either reducing the total number of channels processed with the Fabry-Pérot interferometer 78, or so as to provide for processing an addition signal channel 122 therewith. Such an arrangement would be suitable when the associated air data products being measured therewith are not dependent upon relative wind velocity, the latter of which measure is calibrated responsive to a measure of frequency shift of the reference channel 120 using the Fabry-Pérot interferometer 78. For example, the optical air data system 10'''' illustrated in FIG. 47 would be suitable for measuring either or both of static density $\rho$ and static temperature $T_S$, or to provide for deriving therefrom one or more of static air pressure, total air temperature, speed of sound, air density ratio or pressure altitude.

Heretofore the laser 12 has been assumed to be a generic device capable of providing sufficiently narrow-band photonic radiation at an operative frequency so as to provide for an operative optical air data system 10, 10', 10'', 10''', 10''''. For example, a Nd:YAG laser 12.1 can operate at relatively high power levels so as to provide sufficiently intense illumination so as to provide for relatively long range atmospheric sensing applications. An Nd:YAG laser 12.1 has a fundamental wavelength of 1064 nanometers (nm), from which shorter wavelengths/higher frequencies may be generated using one or more harmonic generators operatively associated with or a part of the Nd:YAG laser 12.1. For example, a second-harmonic generator could be used to convert the fundamental 1064 nm light to second-harmonic 532 nm light which could then be transformed with either a third- or fourth-harmonic generator to generate associated 355 nm or 266 nm light respectively. Heretofore these second-, third- and/or fourth-harmonic generators would be either incorporated in, or free-space coupled to, the laser 12 generally or, more particularly, the Nd:YAG laser 12.1.

As noted hereinabove, ultraviolet light—e.g. 266 nm or 355 nm light that can be generated as described hereinabove—can be suitable for atmospheric sensing applications. One problem associated with ultraviolet light when transmitted or distributed through associated fiber optics 76 of the optical air data system 10, 10', 10'', 10''', 10'''' is the resulting degradation of the associated fiber optics 76, for example, that can occur as a result of a power per unit area therein exceeding a damage threshold, e.g. at a focal point within the fiber optics 76, or a solarization of the fiber optics 76. However, the fiber optics 76 provide for locating relatively sensitive portions of the optical air data system 10, 10', 10'', 10''', 10'''', e.g. the laser 12, Fabry-Pérot interferometer 78, and detection system 80, at a relatively secure location that may be relatively remote from the associated optical head 22 containing the associated beam splitter optics 20, beam steering optics 210, and telescope(s) 26, by providing for efficiently transmitting the associated first 14 and/or second 18 laser beams, and/or the reference beam 16 to the optical head 22, and for transferring the received light signals 44 from the optical head 22 to the Fabry-Pérot interferometer 78.

Figure 48:
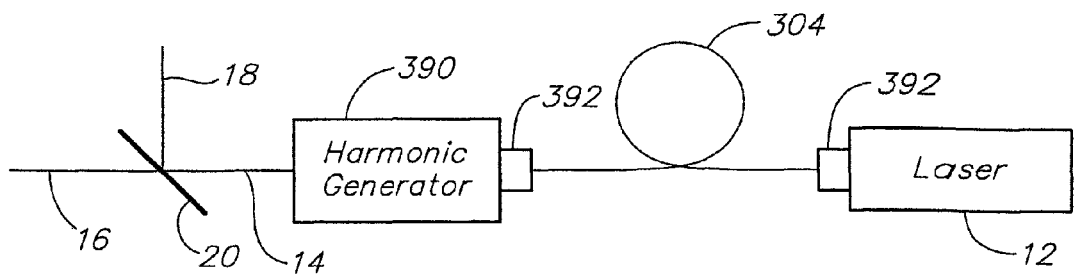
FIG. 48 illustrates a laser coupled with a fiber optic to an associated harmonic generator, the output of which is then propagated in free space.

Referring to FIG. 48, an optical air data system 10, 10', 10", 10''', 10'''' may be adapted to operate at ultraviolet frequencies without the ill affects of associated solarization or power-induced damage of an associated fiber optic 304 coupling the relatively high-power first laser beam 14 operating at a fundamental harmonic to the associated optical head 22 by transmitting relatively long-wavelength laser light from the laser 12 through a fiber optic 304 to an associated harmonic generator 390, generating relatively shorter-wavelength light with the harmonic generator 390, and then transmitting through free space the relatively shorter-wavelength light from the harmonic generator 390 to the beam splitter optic 20 of the optical head 22. The harmonic generator 390 could be incorporated in the optical head 22 so as to provide for optical alignment therewith and ruggedization of the associated harmonic generator 390. Accordingly, this arrangement provides for operation at ultraviolet frequencies and the use of fiber optics 304, 76 to mechanically isolate of the laser 12, Fabry-Pérot interferometer 78, and detection system 80 from the optical head 22, without a substantial prospect of solarization-induced degradation of the fiber optic 304 carrying the relatively high-power laser light from the laser 12 to the optical head 22.

Figure 49A:
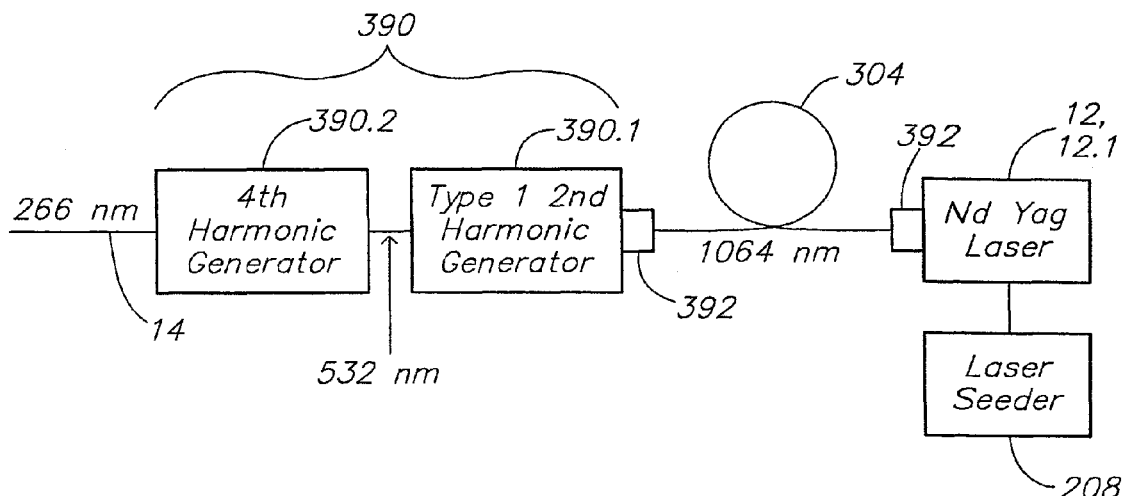
FIG. 49a illustrates a first embodiment of a laser coupled with a fiber optic to a plurality of harmonic generators in series for generating a fourth harmonic.

For example, referring to FIG. 49a, in accordance with a first embodiment, a Nd:YAG laser 12.1 is operatively coupled to a Type 1 second-harmonic generator 390.1 with a fiber optic 304, wherein the Type 1 second-harmonic generator 390.1 provides for converting the 1064 nm laser light from the Nd:YAG laser 12.1 to 532 nm light, which is then operatively coupled over free space to a fourth-harmonic generator 390.2 that provides for converting the 532 nm light from the Type 1 second-harmonic generator 390.1 to 266 nm light of the first laser beam 14. The Type 1 second-harmonic generator 390.1 and the fourth-harmonic generator 390.2 comprise crystals, for example, BBO, KDP and LBO, the selection of which depends upon the manufacturer and various factors, e.g. pulse energy. The crystal used in the Type 1 second-harmonic generator 390.1 is cut in accordance with what is known as a Type 1 cut so as to provide for two photons of 532 nm light to be doubled to 266 nm light by the fourth-harmonic generator 390.2. For example, in one embodiment, the Nd:YAG laser 12.1 can be a model 8030 manufactured by Continuum, which operates in cooperation with a Continuum Part No. 617-8000 Type 1 second-harmonic generator 390.1 and a Continuum Part No. 617-8140 fourth-harmonic generator 390.2. The Nd:YAG laser 12.1 can be either flash-lamp pumped or diode-pumped.

Figure 49B:
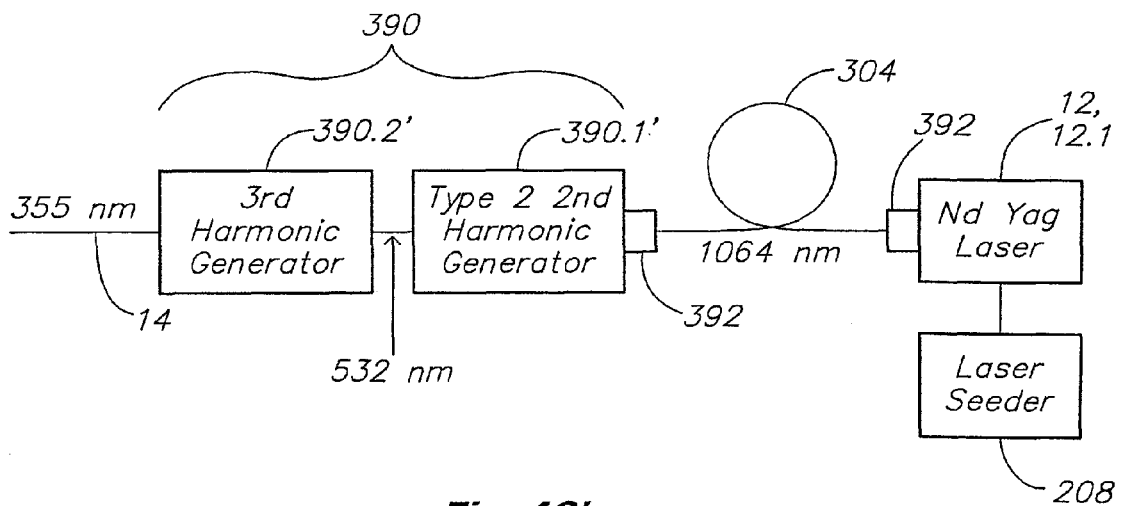
FIG. 49b illustrates a second embodiment of a laser coupled with a fiber optic to a plurality of harmonic generators in series for generating a third harmonic.

As another example, referring to FIG. 49b, in accordance with a second embodiment, a Nd:YAG laser 12.1 is operatively coupled to a Type 2 second-harmonic generator 390.1' with a fiber optic 304, wherein the Type 2 second-harmonic generator 390.1' provides for converting the 1064 nm laser light from the Nd:YAG laser 12.1 to 532 nm light, which is then operatively coupled over free space to a third-harmonic generator 390.2' that provides for converting the 532 nm light from the Type 2 second-harmonic generator 390.1' to 355 nm light of the first laser beam 14. The Type 2 second-harmonic generator 390.1' and the third-harmonic generator 390.2' comprise crystals, for example, BBO, KDP and LBO, the selection of which depends upon the manufacturer and various factors, e.g. pulse energy. The crystal used in the Type 2 second-harmonic generator 390.1' is cut in accordance with what is known as a Type 2 cut so as to provide for one photon of 532 nm light to be mixed with one photon of 1064 nm light by the third-harmonic generator 390.2' so as to generate a corresponding photon of 355 nm light. For example, in one embodiment, the Nd:YAG laser 12.1 can be a model 8030 manufactured by Continuum, which operates in cooperation with a Continuum Part No. 617-9100 Type 2 second-harmonic generator 390.1' and a Continuum Part No. 617-8020 third-harmonic generator 390.2'. The Nd:YAG laser 12.1 can be either flash-lamp pumped or diode-pumped.

Accordingly, in the first and second embodiments illustrated in FIGS. 49a and 49b respectively, the fundamental 1064 nm laser light from the Nd:YAG laser 12.1 is transmitted via a fiber optic 304 to harmonic generators 390.1, 390.2 or 390.1', 390.2' that can be located remotely relative to the Nd:YAG laser 12.1, for example, in the optical head 22, and ultraviolet light generated by the harmonic generators 390.2 or 390.2' is thereafter transmitted through free space. The 1064 nm laser light transmitted through the fiber optic 304 does not result in any substantial degradation thereof.

Figure 49C:
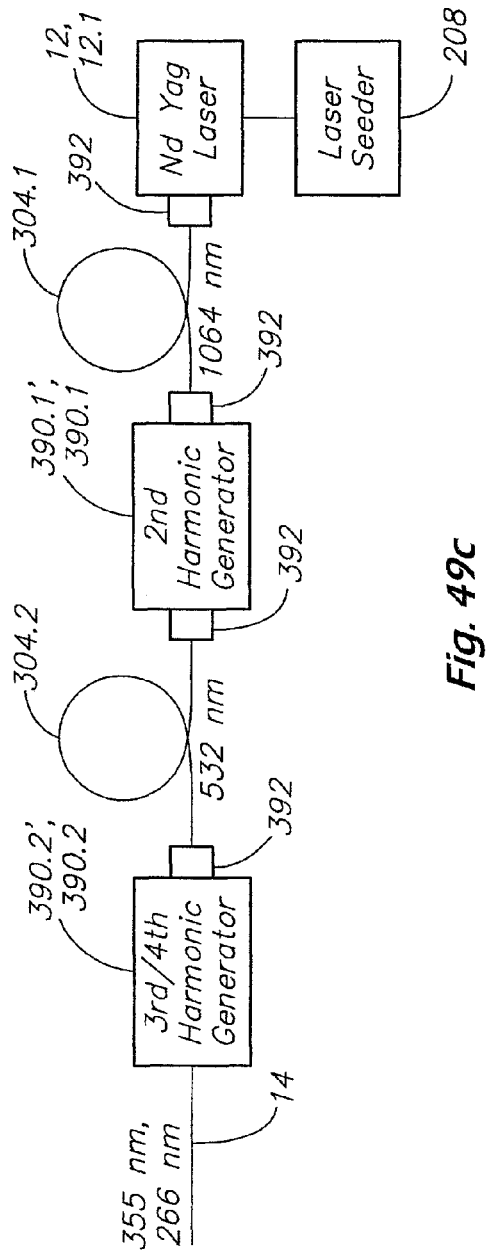
FIG. 49c illustrates a third embodiment of a laser coupled with a first fiber optic to a first harmonic generator, the latter of which is connected to a second harmonic generator with a second fiber optic.

As yet another example, referring to FIG. 49c, in accordance with a third embodiment—a modification of either the first or second embodiments,—the Nd:YAG laser 12.1 is operatively coupled to the associated Type 1 390.1 or Type 2 390.1' second-harmonic generator with a first fiber optic 304.1, and the Type 1 390.1 or Type 2 390.1' second-harmonic generator is operatively coupled to the associated fourth- 390.2 or third-390.2' harmonic generator, respectively, with a second fiber optic 304.2, so that the first fiber optic 304.1 transmits fundamental 1064 nm laser light, and the second fiber optic 304.2 transmits 532 nm laser light, neither of which results in any substantial degradation of the associated first 304.1 or second 304.1 fiber optics.

Figure 49D:
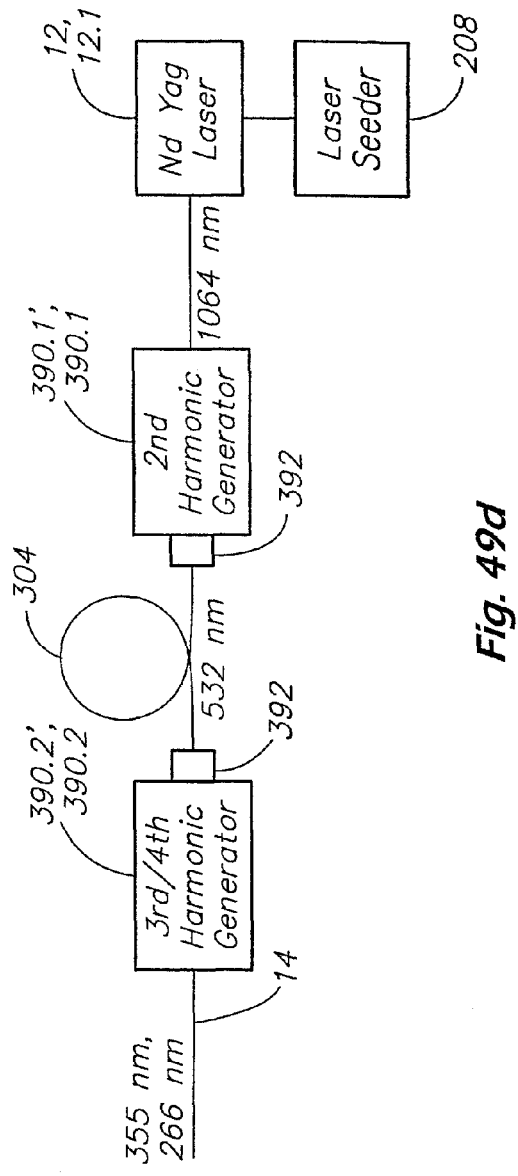
FIG. 49d illustrates a fourth embodiment of a laser coupled to a first harmonic generator, the latter of which is connected to a second harmonic generator with a fiber optic.

As yet another example, referring to FIG. 49d, in accordance with a fourth embodiment—a modification of either the first or second embodiments,—the Nd:YAG laser 12.1 is operatively coupled to the associated Type 1 390.1 or Type 2 390.1' second-harmonic generator via free space, and the Type 1 390.1 or Type 2 390.1' second-harmonic generator is operatively coupled to the associated fourth- 390.2 or third-390.2' harmonic generator, respectively, with a fiber optic 304, so that the fiber optic 304 transmits 532 nm laser light which does not result in any substantial degradation thereof. For example, the Type 1 390.1 or Type 2 390.1' second-harmonic generator could be either attached to, located within, or otherwise a part of the Nd:YAG laser 12.1.

The fiber optics 304, 304.1, 304.2 used in the first through fourth embodiments of FIGS. 49a-d may comprise either single optical fibers or bundles of optical fibers. An optics assembly 392 operatively associated at each end of the associated fiber optics, i.e. at each of the entrance and exit ends, provides for focusing and/or collimating and/or otherwise shaping the associated beam of laser light into or out of the associated fiber optics 304, 304.1, 304.2 so as to provide for efficiently transferring light from the laser 12, 12.1 to the associated first laser beam 14. The optics assembly 392 may or may not be integrated with the associated fiber optics 304, 304.1, 304.2, and may or may not be hermetically sealed at the associated fiber interface.

Figure 50:
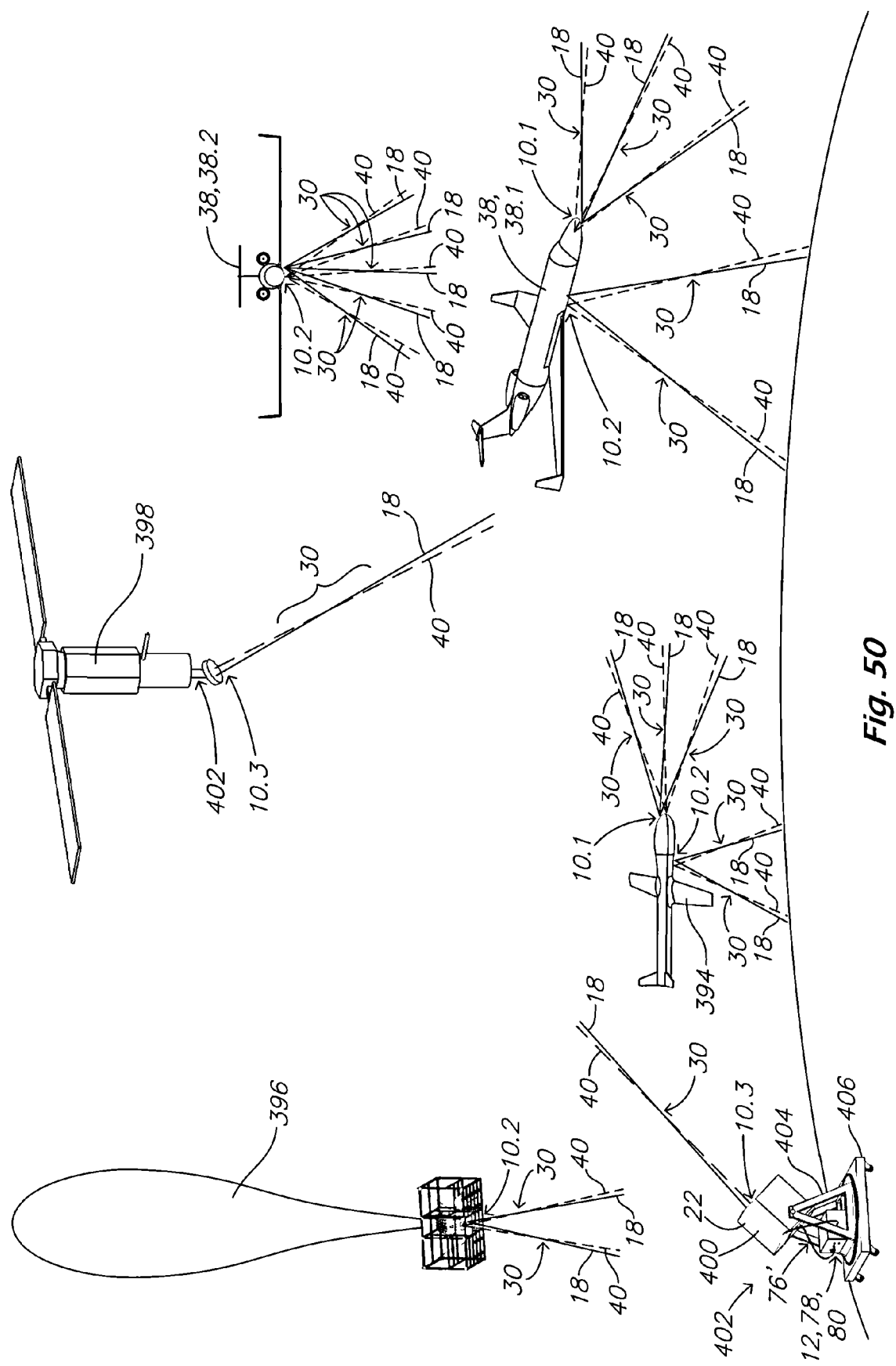
FIG. 50 illustrates various applications of an optical air data system.

Referring to FIG. 50, various optical air data systems 10, 10', 10", 10''', 10'''' can be used in a variety of applications, including flight control or flight data monitoring, for example, for an aircraft 38 or UAV 394; or monitoring atmospheric or weather conditions from an aircraft 38.1, 38.2, UAV 394, balloon 396, satellite 398, or ground-based LIDAR system 400, For example, the aircraft 38, 38.1 and UAV 394 illustrated in FIG. 50 each incorporate a first optical air data system 10.1 that incorporates three lines of sight 40 so as to provide for measuring an associated relative wind vector in addition to other air data products. Generally the optical air data system 10 can be adapted for airframe applications which, for example, might otherwise incorporate a pitot-static tube for measuring air speed. In addition to air speed, the optical air data system 10 provides for optically measuring, or calculating from optical measurements, a substantial quantity of air data products, and can be adapted to detect wind shear, wake vortices, clear air turbulence, and engine stall (unstart) conditions. Common air data products include, but are not limited to, Mach number, true airspeed, calibrated airspeed, vertical speed, static density, static air temperature, sideslip, angle of attack, pressure altitude, and dynamic pressure. The air data products can be used directly by an aircraft flight computer for flight control purposes. The optical air data system 10 provides for an airframe-independent design that can be flush-mounted to the skin of the airframe, e.g. without protrusions that otherwise might increase the airframe's radar cross section and drag, so as to provide for relatively low observability and drag. The optical air data system 10 can operate at substantial angles of attack. For example, a properly-configured optical air data system 10 can operate at a 90 degree angle of attack. The optical air data system 10 can be adapted to a variety of airframes, for example, including highly maneuverable aircraft and hoverable aircraft. The optical air data system 10 provides for an airframe-independent design that can be relatively inexpensive to calibrate, recalibrate or service.

As another example, the aircraft 38, 38.1, 38.2, UAV 394, and balloon 396 illustrated in FIG. 50 each incorporate a second optical air data system 10.2 adapted with a plurality of lines of sight 40, so as to provide for substantially simultaneously measuring air data products from one or more interaction regions 30 along each of the associated lines of sight 40. For example, the first aircraft 38.1 incorporates two lines of sight 40 distributed transversely with respect to the associated direction of travel thereof, and the second aircraft 38.2 incorporates five lines of sight 40 distributed transversely with respect to the associated direction of travel thereof, so as to provide for automatically acquiring a substantial amount of atmospheric data (e.g. density, temperature and wind velocity) that can be used for either monitoring or predicting weather, or for monitoring particular emissions into the atmosphere. In accordance with another embodiment, the UAV 394 is illustrated with lines of sight 40 substantially along the direction of travel thereof, which can provide for automatically acquiring a substantial amount of atmospheric data (e.g. density, temperature and wind velocity) that, for example, can be used for either monitoring or predicting weather dynamics, or for monitoring the dynamics of particulate emissions into the atmosphere. Generally, the orientation of the plurality of lines of sight 40 relative to the associated vehicle or the associated direction of travel thereof is not limiting, i.e. either other orientations or a combination of orientations may be used.

As yet another example, the satellite 398 and the ground-based LIDAR system 400 illustrated in FIG. 50 each incorporate a third optical air data system 10.3 adapted with a line of sight 40 that is directed respectively downwards or upwards into the atmosphere so as to provide for measuring air data products from one or more interaction regions 30 along each of the associated one or more lines of sight 40, for example, so as to provide for automatically acquiring a substantial amount of atmospheric data (e.g. density, temperature and wind velocity) that can be used for either monitoring or predicting weather, or for monitoring particular emissions into the atmosphere.

Figure 51:
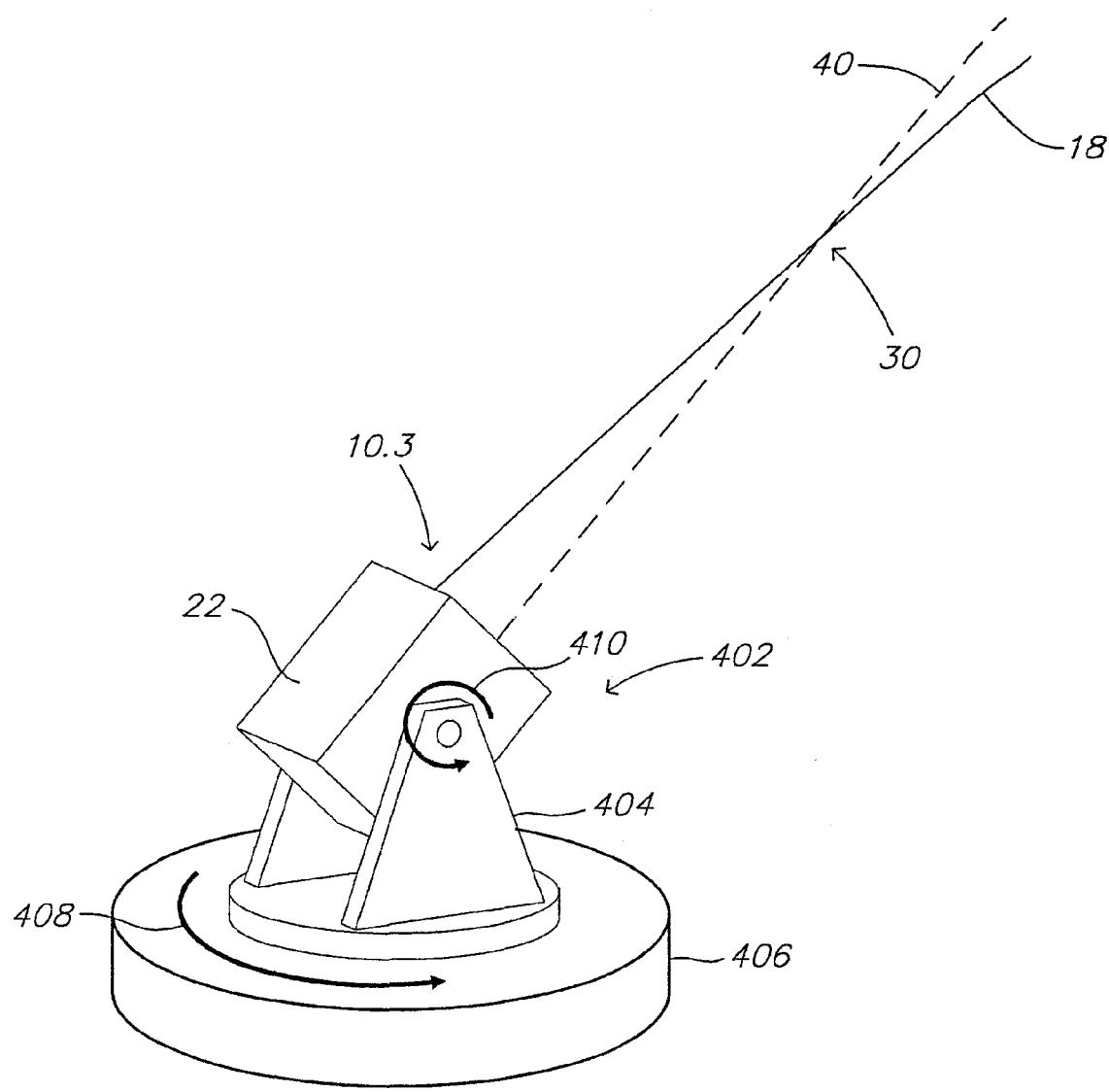
FIG. 51 illustrates a gimbal mechanism operatively associated with an optical air data system.

Referring to FIG. 51, and as illustrated in FIG. 50 for the satellite 398 and the ground-based LIDAR system 400, the third optical air data system 10.3 may be operatively associated with a gimbal mechanism 402 comprising an azimuthally-rotatable platform 404 which is adapted to pivotally support an optical head 22 so as to provide for an elevational rotation thereof relative a base 406 to which the azimuthally-rotatable platform 404 is operatively associated. Accordingly, the azimuthally-rotatable platform 404 is adapted to rotate relative to the base 406, for example, responsive to an associated motor drive system, so as to define an associated azimuth angle 408 of the optical head 22, and the optical head 22 is adapted to rotate relative to the azimuthally-rotatable platform 404, for example, responsive to an associated motor drive system, so as to define an associated elevation angle 410 of the optical head 22. Accordingly, coordinated rotations of the optical head 22 in both azimuth 408 and elevation 410 angle provide for acquiring associated optical air data from associated interaction regions 30 of an associated spherical shell of the atmosphere 24. The optical air data system 10.3 may provide for a plurality or range of interaction regions 30 associated with the associated second laser beam 18 so as to provide for sampling optical air data from a corresponding plurality of spherical shells. Referring to FIG. 50, in one embodiment illustrated in cooperation with the ground-based LIDAR system 400, the laser 12, interferometer 78 and detector system 80 of the optical air data system 10.3 may be mounted on the associated azimuthally-rotatable platform 404 so as to rotate therewith, wherein the laser 12 and interferometer 78 are operatively coupled to the associated optical head 22 with an associated fiber-optic bundle 76'. The base 406 of the gimbal mechanism 402 of the ground-based LIDAR system 400 is adapted to provide for mobile operation thereof. The base 406 of the gimbal mechanism 402 of the satellite 398 is operatively coupled to the satellite 398 so as to provide for scanning the optical head 22, for example, as the satellite 398 travels in its orbit.

It should be understood that any of the optical air data systems 10.2, 10.3 illustrated in FIG. 50 can be operatively associated with any of the associated platforms (i.e. aircraft 38.1, 38.2, UAV 394, balloon 396, satellite 398, or ground-based LIDAR system 400) or other platforms. For example, the satellite 398 could incorporate an optical air data system 10.2 comprising a plurality of lines of sight 40 arranged transverse to the direction of travel. For example, in one embodiment, eight lines of sight 40 are contemplated. As another example, the balloon 396 could incorporate an optical air data system 10.2 with a single line of sight 40, possibly operatively associated with a gimbal system 402. As another example, an optical head 22 operatively associated with a gimbal system 402 could incorporate a plurality of lines of sight 40 and could provide for either range-resolved imaging or a plurality of interaction regions 30 and a plurality of associated light signals 44 associated with a given line of sight 40.

Accordingly, the optical air data system 10, 10', 10", 10''', 10"" can be adapted to measure air data products on a variety of platforms, for example, including, but not limited to, satellites 398, aircraft 38, UAVs 394, glide weapon systems, ground-based platforms (stationary or mobile), and watercraft. The optical air data system 10, 10', 10", 10''', 10"" can be adapted to measure air data products of a variety of atmospheres 24, for example, that of the Earth or other planetary or celestial bodies, or can be adapted to measure or map air data products of fields within a wind tunnel or surrounding an aerodynamic body during the operation thereof. Furthermore, although one embodiment uses ultraviolet (UV) laser light, the optical air data system 10 can operate over a large range of wavelengths spanning from the visible down to the ultraviolet. The ultraviolet light provides additional stealth characteristics for the system because the light is quickly absorbed by the atmosphere 24, and is not otherwise easily detected from relatively long-range distances. However, the optical air data system 10 can also operate in other wavelength regions, such as longer ultraviolet wavelengths or even visible wavelengths. For example, a variety of lasers 12 can be used, including, but not limited to: Ruby (694 nm); Neodymium-based lasers: Nd:YAG, Nd: Glass (1.062 microns, 1.054 microns), Nd:Cr:GSGG, Nd:YLF (1.047 and 1.053 microns), Nd:YVO (orthovanadate, 1.064 microns); Erbium-based lasers: Er:YAG and Er:Glass; Ytterbium-based lasers: Yb:YAG (1.03 microns); Holmium-based lasers: Ho:YAG (2.1 microns); Thulium-based lasers: Tm:YAG (2.0 microns); and tunable lasers: Alexandrite (700-820 nm), Ti:Sapphire (650-1 100 nm), and Cr:LiSAF. The associated laser 12 can be either pulsed—at any Pulse Repetition Frequency (PRF)—or continuous wave (CW).

While specific embodiments have been described in detail in the foregoing detailed description and illustrated in the accompanying drawings, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

What is claimed is:

1. An optical air data system, comprising:
    a. a reference beam from a first beam of light generated by a laser;
    b. at least one second beam of light from said first beam of light, wherein said at least one second beam of light is directed into an atmosphere along an associated axis;
    c. at least one telescope adapted to receive light backscattered by molecules or aerosols of said atmosphere responsive to a corresponding at least one said second beam of light;
    d. an interferometer, wherein a first portion of said interferometer is adapted to receive a light signal from said light backscattered by said molecules or aerosols of said atmosphere, at least one second portion of said interferometer is adapted to receive at least one of said reference beam and at least one other light signal from said light backscattered by said molecules or aerosols of said atmosphere, said interferometer is operative to generate a first fringe pattern associated with said light signal from said light backscattered by said molecules or aerosols of said atmosphere, and said interferometer is operative to generate at least one second fringe pattern associated with said at least one of said reference beam and at least one other light signal from said light backscattered by said molecules or aerosols of said atmosphere;
    e. at least one detector, wherein said at least one detector is adapted to detect said first fringe pattern and said at least one second fringe pattern, and said at least one detector is adapted to output a corresponding resulting at least one signal; and
    f. a data processor, wherein said data processor provides for gating said corresponding resulting at least one signal so as to provide for generating a measurement responsive to a range from the optical air data system.

2. An optical air data system as recited in claim 1, wherein said light received by said at least one telescope is backscattered either by said molecules of said atmosphere or by said aerosols of said atmosphere, or said light received by said at least one telescope is backscattered by both said molecules and said aerosols of said atmosphere.

3. An optical air data system, comprising:
    a. a reference beam from a first beam of light generated by a laser;
    b. at least one second beam of light from said first beam of light, wherein said at least one second beam of light is directed into an atmosphere along an associated axis;
    c. at least one telescope adapted to receive light backscattered by molecules or aerosols of said atmosphere responsive to a corresponding at least one said second beam of light;
    d. an interferometer, wherein a first portion of said interferometer is adapted to receive a light signal from said light backscattered by said molecules or aerosols of said atmosphere, at least one second portion of said interferometer is adapted to receive at least one of said reference beam and at least one other light signal from said light backscattered by said molecules or aerosols of said atmosphere, said interferometer is operative to generate a first fringe pattern associated with said light signal from said light backscattered by said molecules or aerosols of said atmosphere, at least a portion of said reference beam and at least a portion of one of said light signal and said at least one other light signal are multiplexed together so as to form a corresponding multiplexed signal, said interferometer is adapted to receive said corresponding multiplexed signal, and said interferometer is operative to generate at least one second fringe pattern associated with said at least one of said reference beam and at least one other light signal from said light backscattered by said molecules or aerosols of said atmosphere; and
    e. at least one detector, wherein said at least one detector is adapted to detect said first fringe pattern and said at least one second fringe pattern, and said at least one detector is adapted to output a corresponding resulting at least one signal.

4. An optical air data system as recited in claim 3, wherein said at least a portion of said reference beam and said at least a portion of one of said light signal and said at least one other light signal are operatively coupled to said interferometer with separate fiber-optic cables that are bundled to one another at corresponding ends that illuminate said first and one of said at least one second portions of said interferometer.

5. An optical air data system as recited in claim 3, wherein said at least a portion of said reference beam and said at least a portion of one of said light signal and said at least one other light signal are combined as said corresponding multiplexed signal with a beam splitter and then operatively coupled to said interferometer so as to illuminate said first and one of said at least one second portions of said interferometer.

6. An optical air data system as recited in claim 5, wherein said corresponding multiplexed signal is operatively coupled to said interferometer with a fiber-optic cable.

7. An optical air data system as recited in claim 3, further comprising at least one circle-to-line interferometer optic adapted to transform at least one of said first fringe pattern and said at least one second fringe pattern from at least one at least partially circular pattern to a corresponding at least one substantially linear pattern, wherein said at least one circle-to-line interferometer optic is adapted to process a fringe pattern responsive to said corresponding multiplexed signal.

8. An optical air data system as recited in claim 3, wherein said first and said at least one second portions of said interferometer are substantially the same.

9. An optical air data system as recited in claim 3, wherein said light received by said at least one telescope is backscattered either by said molecules of said atmosphere or by said aerosols of said atmosphere, or said light received by said at least one telescope is backscattered by both said molecules and said aerosols of said atmosphere.

10. An optical air data system, comprising:
   a. a reference beam from a first beam of light generated by a laser;
   b. at least one second beam of light from said first beam of light, wherein said at least one second beam of light is directed into an atmosphere along an associated axis;
   c. at least one telescope adapted to receive light backscattered by molecules or aerosols of said atmosphere responsive to a corresponding at least one said second beam of light;
   d. an interferometer, wherein a first portion of said interferometer is adapted to receive a light signal from said light backscattered by said molecules or aerosols of said atmosphere, at least one second portion of said interferometer is adapted to receive at least one of said reference beam and at least one other light signal from said light backscattered by said molecules or aerosols of said atmosphere, said interferometer is operative to generate a first fringe pattern associated with said light signal from said light backscattered by said molecules or aerosols of said atmosphere, and said interferometer is operative to generate at least one second fringe pattern associated with said at least one of said reference beam and at least one other light signal from said light backscattered by said molecules or aerosols of said atmosphere;
   e. at least one circle-to-line interferometer optic adapted to transform at least one of said first fringe pattern and said at least one second fringe pattern from at least one at least partially circular pattern to a corresponding at least one substantially linear pattern; and
   f. at least one detector, wherein said at least one detector is adapted to detect said first fringe pattern and said at least one second fringe pattern, and said at least one detector is adapted to output a corresponding resulting at least one signal.

11. An optical air data system as recited in claim 10, wherein said at least one circle-to-line interferometer optic comprises:
   a. a first circle-to-line interferometer optic adapted to transform said first fringe pattern from a first at least partially circular pattern to a corresponding first substantially linear pattern; and
   b. at least one second circle-to-line interferometer optic adapted to transform a corresponding said at least one second fringe pattern from at least one second at least partially circular pattern to a corresponding at least one second substantially linear pattern.

12. An optical air data system as recited in claim 11, wherein said at least one second fringe pattern comprises a plurality of second fringe patterns, said at least one second circle-to-line interferometer optic comprises a plurality of second circle-to-line interferometer optics, and each of said plurality of second fringe patterns is processed by a different second circle-to-line interferometer optic of said plurality of second circle-to-line interferometer optics.

13. An optical air data system as recited in claim 11, wherein at least one of said first circle-to-line interferometer optic and said at least one second circle-to-line interferometer optics comprises an at least partially conical reflector and said at least one detector is adapted to detect light directed at said at least partially conical reflector, wherein an apex of a cone underlying said at least partially conical reflector is proximate to a focal plane of at least one of said first fringe pattern and said corresponding said at least one second fringe pattern.

14. An optical air data system as recited in claim 10, wherein at least one of said at least one circle-to-line interferometer optic is adapted process a plurality of fringe patterns, wherein said plurality of fringe patterns are selected from said first fringe pattern and said at least one second fringe pattern.

15. An optical air data system as recited in claim 10, wherein said at least one circle-to-line interferometer optic comprises a plurality of circle-to-line interferometer optics each arranged on a separate sloping face of an underlying substrate, further comprising a plurality of reflective surfaces adapted in cooperation with said plurality of circle-to-line interferometer optics to direct each said corresponding at least one substantially linear pattern onto a different portion of said at least one detector.

16. An optical air data system as recited in claim 15, wherein said plurality of circle-to-line interferometer optics comprise two circle-to-line interferometer optics substantially opposed to one another, and said plurality of reflective surfaces are adapted to direct each of said corresponding at least one substantially linear pattern along substantially a common row of photosites of said at least one detector.

17. An optical air data system as recited in claim 15, wherein said plurality of circle-to-line interferometer optics comprise four circle-to-line interferometer optics on a first pyramidal substrate, and said plurality of reflective surfaces comprise four planar reflective surfaces on a second pyramidal substrate, and said plurality of reflective surfaces are adapted to direct each said corresponding at least one substantially linear pattern along a different leg of an associated cross-pattern.

18. An optical air data system as recited in claim 10, wherein said light received by said at least one telescope is backscattered either by said molecules of said atmosphere or by said aerosols of said atmosphere, or said light received by said at least one telescope is backscattered by both said molecules and said aerosols of said atmosphere.

19. An optical air data system, comprising:
   a. a reference beam from a first beam of light generated by a laser;
   b. at least one second beam of light from said first beam of light, wherein said at least one second beam of light is directed into an atmosphere along an associated axis;
   c. at least one telescope adapted to receive light backscattered by molecules or aerosols of said atmosphere responsive to a corresponding at least one said second beam of light;
   d. an interferometer, wherein a first portion of said interferometer is adapted to receive a light signal from said light backscattered by said molecules or aerosols of said atmosphere, at least one second portion of said interferometer is adapted to receive at least one of said reference beam and at least one other light signal from said light backscattered by said molecules or aerosols of said atmosphere, said interferometer is operative to generate a first fringe pattern associated with said light signal from said light backscattered by said molecules or aerosols of said atmosphere, and said interferometer is operative to generate at least one second fringe pattern associated with said at least one of said reference beam and at least one other light signal from said light backscattered by said molecules or aerosols of said atmosphere;

e. at least one circle-to-line interferometer optic adapted to transform at least one of said first fringe pattern and said at least one second fringe pattern from at least one at least partially circular pattern to a corresponding at least one substantially linear pattern; and f. at least one detector, wherein said at least one detector comprises a CCD detector, said corresponding at least one substantially linear pattern is substantially aligned with a row of photosites of a recording zone of said CCD detector, said CCD detector is adapted operate in accordance with a process of successively transferring charges from one adjacent row of photosites to another while said corresponding at least one substantially linear pattern illuminates said recording zone of said CCD detector so as to provide for recording at least one range-resolved image of said corresponding at least one substantially linear pattern, said at least one detector is adapted to detect at least one of said first fringe pattern and said at least one second fringe pattern, and said at least one detector is adapted to output a corresponding resulting at least one signal.

20. An optical air data system as recited in claim 19, wherein said laser is pulsed, and said process of successively transferring said charges is synchronized with a pulsing of said laser so as to commence after said laser is pulsed.

21. An optical air data system as recited in claim 19, wherein said process of successively transferring said charges provides for transferring said charges from an imaging region to a frame-transfer region.

22. An optical air data system as recited in claim 21, wherein said process of successively transferring said charges provides for cumulatively recording said at least one range-resolved image.

23. An optical air data system as recited in claim 22, wherein said laser is pulsed, said process of successively transferring said charges is synchronized with a pulsing of said laser so as to commence after said laser is pulsed, and said at least one range-resolved image is cumulatively recorded by transferring said charges from said frame-transfer region to said imaging region in synchronism with said pulsing of said laser.

24. An optical air data system as recited in claim 19, wherein said light received by said at least one telescope is backscattered either by said molecules of said atmosphere or by said aerosols of said atmosphere, or said light received by said at least one telescope is backscattered by both said molecules and said aerosols of said atmosphere.

* * * * *